(12) United States Patent
Yamamoto et al.

(10) Patent No.: US 12,325,727 B2
(45) Date of Patent: Jun. 10, 2025

(54) METHOD FOR PRODUCING PEPTIDE COMPOUND, PROTECTIVE GROUP-FORMING REAGENT, AND AROMATIC HETEROCYCLIC COMPOUND

(71) Applicant: FUJIFILM CORPORATION, Tokyo (JP)

(72) Inventors: Yosuke Yamamoto, Kanagawa (JP); Kazuhei Kaneko, Kanagawa (JP); Motomasa Takahashi, Kanagawa (JP); Makoto Takahashi, Kanagawa (JP); Mika Imamura, Kanagawa (JP); Hirotaka Satou, Kanagawa (JP); Hirofumi Omura, Kanagawa (JP); Yuji Yoshimitsu, Kanagawa (JP); Keita Tanaka, Kanagawa (JP); Daisuke Nakagawa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 79 days.

(21) Appl. No.: 17/409,692

(22) Filed: Aug. 23, 2021

(65) Prior Publication Data

US 2021/0380633 A1 Dec. 9, 2021

Related U.S. Application Data

(63) Continuation of application No. PCT/JP2020/007478, filed on Feb. 25, 2020.

(30) Foreign Application Priority Data

| Feb. 28, 2019 | (JP) | 2019-035775 |
| Jun. 28, 2019 | (JP) | 2019-122489 |

(51) Int. Cl.
  *C07K 1/06* (2006.01)
  *C07D 209/08* (2006.01)
  *C07K 1/02* (2006.01)

(52) U.S. Cl.
  CPC ............. *C07K 1/06* (2013.01); *C07D 209/08* (2013.01); *C07K 1/02* (2013.01); *C07K 1/062* (2013.01); *C07K 1/066* (2013.01)

(58) Field of Classification Search
  CPC ........................ C07D 209/08; C07K 1/062
  See application file for complete search history.

(56) References Cited

U.S. PATENT DOCUMENTS

| 2,825,734 A | 3/1958 | Speeter et al. |
| 3,957,288 A | 5/1976 | Lemahieu et al. |
| 9,284,344 B2 | 3/2016 | Kim et al. |
| 2009/0299103 A1 | 12/2009 | Chiba et al. |
| 2010/0249374 A1 | 9/2010 | Takahashi |
| 2011/0160433 A1 | 6/2011 | Takahashi |
| 2012/0296074 A1 | 11/2012 | Hirai et al. |
| 2015/0112053 A1 | 4/2015 | Kim et al. |
| 2017/0320904 A1 | 11/2017 | Hirai et al. |

(Continued)

FOREIGN PATENT DOCUMENTS

| CN | 108473526 A | 8/2018 |
| EP | 4006045 A1 | 6/2022 |

(Continued)

OTHER PUBLICATIONS

Office action dated Jun. 15, 2022 from the IPO in a Indian patent application No. 202247000909 corresponding to the instant patent application.
Extended European Search Report dated Jun. 23, 2022, issued in corresponding EP Patent Application No. 20831790.9.
Murayama, K. et al., "Synthesis, structure, and photophysical/chiroptical properties of benzopicene-based p-conjugated molecules", Journal of Organic Chemistry, 2017, vol. 82, No. 2, pp. 1136-1144.
Mamoru Mizuno et al., "Fluorous Glycopeptide Synthesis without Protection of Sugar Hydroxy Groups", Laboratory of Glycoorganic Chemistry, The Noguchi Institute, Chemistry Letters vol. 34, No. 3, pp. 426-427, Feb. 22, 2005, retrieved from https://doi.org/10.1246/cl.2005.426.
Office action dated Oct. 28, 2021 from the IPO in a Indian patent application No. 202147038838 corresponding to the instant patent application.

(Continued)

*Primary Examiner* — Christina Bradley
(74) *Attorney, Agent, or Firm* — SOLARIS Intellectual Property Group, PLLC

(57) ABSTRACT

Provided are a method for producing a peptide compound including a step of using an aromatic heterocyclic compound represented by Formula (1); a protective group-forming reagent including the compound; and the compound. In Formula (1), a ring A represents an aromatic heterocyclic ring, $Y^A$'s each independently represent —OH, —NHR, —SH, or —$X^0$, where $X^0$ represents Cl, Br, or I, $R^A$ and $R^C$ each independently represent an aliphatic hydrocarbon group or an organic group having an aliphatic hydrocarbon group, $R^B$s' each independently represent a monovalent aliphatic hydrocarbon group, a (1+c)-valent aromatic group, or a (1+c)-valent heteroaromatic group, where, in a case where both a and c is 0, $R^B$ is a monovalent aliphatic hydrocarbon group, and the number of carbon atoms in at least one aliphatic hydrocarbon group of $R^A$, $R^B$, or $R^C$ is 12 or more (1)

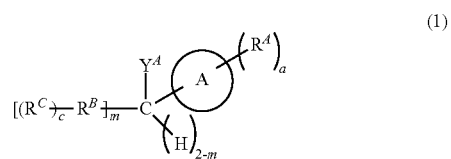

18 Claims, No Drawings

Specification includes a Sequence Listing.

(56) References Cited

U.S. PATENT DOCUMENTS

| | | | |
|---|---|---|---|
| 2018/0282365 | A1 | 10/2018 | Hirai et al. |
| 2019/0023726 | A1 | 1/2019 | Yano et al. |
| 2019/0031702 | A1 | 1/2019 | Rohloff |
| 2021/0380634 | A1 | 12/2021 | Yamamoto et al. |
| 2022/0112233 | A1 | 4/2022 | Yamamoto et al. |

FOREIGN PATENT DOCUMENTS

| | | | |
|---|---|---|---|
| JP | S49-98642 | A | 9/1974 |
| JP | S60-252441 | A | 12/1985 |
| JP | H06-271577 | A | 9/1994 |
| JP | 2000-44493 | A | 2/2000 |
| JP | 2009-185063 | A | 8/2009 |
| JP | 5979139 | B2 | 8/2016 |
| JP | 2019-035775 | A | 3/2019 |
| JP | 2019-0122489 | A | 7/2019 |
| TW | 201734030 | A | 10/2017 |
| WO | 9732837 | A1 | 9/1997 |
| WO | 2004/067522 | A1 | 8/2004 |
| WO | 2010/113939 | A1 | 10/2010 |
| WO | 2011/078295 | A1 | 6/2011 |
| WO | 2012157723 | A1 | 11/2012 |
| WO | 2013/159863 | A1 | 10/2013 |
| WO | 2013179412 | A1 | 12/2013 |
| WO | 2015/168461 | A2 | 11/2015 |
| WO | 2016117663 | A1 | 7/2016 |
| WO | 2017/038650 | A1 | 3/2017 |
| WO | 2017104836 | A1 | 6/2017 |
| WO | 2018203574 | A1 | 11/2018 |
| WO | 2018212236 | A1 | 11/2018 |
| WO | 2020175472 | A1 | 9/2020 |
| WO | 2020262258 | A1 | 12/2020 |
| WO | 2021039935 | A1 | 3/2021 |

OTHER PUBLICATIONS

English language translation of the following: Office action dated Feb. 28, 2023 from the JPO in a Japanese patent application No. 2021-543021 corresponding to the instant patent application. This office action translation is submitted now in order to supplement the understanding of the cited references which are being disclosed in the instant Information Disclosure Statement.
Rasale, D. B. et al., "Lipase catalyzed inclusion of gastrodigenin for the evolution of blue light emitting peptide nanofibers", Chemical Communications, 2014, vol. 50, No. 63, p. 8685-8688.
Ishigaki, Y. et al., "Three-way output molecular response system based on tetrakis(3,4-dialkoxphenyl)-3,4-dihydro[5]Helicenes: Perturbation of Properties by Long Alkyl Chains", Heterocycles, vol. 90, No. 1, p. 126-135, 2015, The Japan Institute of Heterocycles Chemistry.
Extended European Search Report dated Sep. 15, 2022, issued in corresponding EP Patent Application No. 20858185.0.
English language translation of the following: Office action dated Sep. 27, 2022 from the JPO in a Japanese patent application No. 2021-526941 corresponding to the instant patent application.
Notice regarding a non-compliant or non-responsive amendment issued by USPTO on May 15, 2023, in related U.S. Appl. No. 17/408,474.
Office Action dated Mar. 26, 2024, issued by the EPO in corresponding EP Patent Application No. 20763894.1.
English language translation of the following: Office action dated Apr. 18, 2024 from the TIPO in a Taiwan patent application No. 109129448 corresponding to the instant patent application.
English language translation of the following: Office action dated Apr. 22, 2024 from the TIPO in a Taiwan patent application No. 109121462 corresponding to the instant patent application.
English language translation of the following: Office action dated Aug. 25, 2023 from the KIPO in a Korean patent application No. 10-2021-7027562 corresponding to the instant patent.

English language translation of the following: Office action dated Aug. 25, 2023 from the KIPO in a Korean patent application No. 10-2021-7028084 corresponding to the instant patent.
English language translation of the following: Office action dated Feb. 23, 2024 from the KIPO in a Korean patent application No. 10-2021-7027562 corresponding to the instant patent application.
Bolsinger et al., "Poly (3,6-carbazolylmethylene)s with fluorinated and nonflourinated tapered building side groups", Polymer Bulletin, 38, pp. 117-124, 1997, Germany.
English language translation of the following: Office action dated Feb. 15, 2024 from the TIPO in a Taiwan patent application No. 109106449 corresponding to the instant patent application.
Kaucher M. S. et al., Selective Transport of Water Mediated by Porous Dendritic Dipeptides, Journal of the American Chemical Society, 2007, vol. 129, p. 11698-11699.
Registry(STN) [online], Jan. 27, 1993, [Search date May 7, 2020], CAS: 145543-42-6.
Registry(STN) [online], Jan. 27, 1993, [Search date May 7, 2020], CAS: 145543-43-7.
Registry(STN) [online], Sep. 18, 2013, [Search date May 7, 2020], CAS: 1452164-35-0.
English language translation of the following: Office action dated May 10, 2022 from the JPO in a Japanese patent application No. 2021-502269 corresponding to the instant patent application. This office action translation is submitted now in order to supplement the understanding of the cited references which are being disclosed in the instant Information Disclosure Statement.
Extended European Search Report dated Mar. 17, 2022, issued in corresponding EP Patent Application No. 20763669.7.
English language translation of the following: Office action dated May 24, 2022 from the JPO in a Japanese patent application No. 2021-502270 corresponding to the instant patent application.
English language translation of the following: Decision of Refusal dated Aug. 8, 2023 from the JPO in a Japanese patent application No. 2021-543021 corresponding to the instant patent application.
Office Action dated Oct. 12, 2022, issued by the CIPO in corresponding Canadian Patent Application No. 3,131,774.
Office Action dated Oct. 21, 2022, issued by the CIPO in corresponding Canadian Patent Application No. 3,131,772.
English language translation of the following: Decision of Refusal dated Nov. 22, 2022 from the JPO in a Japanese patent application No. 2021-502270 corresponding to the instant patent application.
International Search Report issued in International Application No. PCT/JP2020/007478 on Jun. 2, 2020.
Written Opinion of the ISA issued in International Application No. PCT/JP2020/007478 on Jun. 2, 2020.
Office action dated Jul. 11, 2022 from the IPO in a Indian patent application No. 202147038861 corresponding to the Instant patent application.
English language translation of the following: Office action dated Dec. 19, 2023 from the JPO in a Japanese patent application No. 2023-026563 corresponding to the instant patent application.
English language translation of the following: Notice of Termination of Reconsideration by Examiners before Appeal Proceedings dated May 9, 2023 from the JPO in a Japanese patent application No. 2021-502270 corresponding to the instant patent application.
Yen-Ju Cheng et al., "Carbazole-Based Ladder-Type Heptacylic Arene with Aliphatic Side Chains Leading to Enhanced Efficiency of Organic Photovoltaics", Chemistry of Materials, 23(9), 2011, pp. 2361-2369, XP055121925, Department of Applied Chemistry, National Chiao Tung University, Taiwan.
Ravi Kumar Cheedarala et al., "Ladder-type heteroacene polymers bearing carbazole and thiophene ring units and their use in field-effect transistors and photovoltaic cells", Journal of Materials Chemistry, 21(3), 2011, pp. 843-850, XP093048796.
Chia Juan Lim et al., "Synthesis and characterization of three thienopyridazine-based copolymers and their application in OFET", Tetrahedron Letters. 57(14), 2016, pp. 1523-1527, XP029442306, published by Elsevier Ltd.
Office Action dated May 30, 2023, issued by the EPO in corresponding EP Patent Application No. 20763894.1.
Christiansen, Jan et al., "Amino-acids and peptides. Part 46. Synthesis of Bradykinin Analogues Modified in the Vicinity of the

(56) References Cited

OTHER PUBLICATIONS

Carboxy-group", Journal of the Chemical Society, Perkin Transactions 1, Jan. 1, 1982, p. 1229, Cambridge, UK.
Mironov, A. F. et al., "Synthesis and some transformations of pyrroles with aliphatic acyl substituents", Chemistry of Heterocyclic Compounds, vol. 9, No. Jan. 1, 1973, pp. 22-25. Retrieved from URL:https://link.springer.com/content/pdf/10.1007/BF00476141.pdf>.
Treibs, Alfred et al., "Synthese von tert.-Butyl-und Octadecylatioporphyrin", Justus Liebigs Ann. Chem., Jan. 1, 1971, pp. 127-134, Retrieved from URL:https//chemistry-europe.onlinelibrary.wiley.com/doi/10.1002/lac.19717510115.
Greenhouse, Robert et al., "Synthesis of Alkylpyrroles by the Sodium Borohydride Reduction of Acylpyrroles", Journal of Organic Chemistry, vol. 50, No. 16, Jan. 1, 1985, pp. 2961-2965, Retrieved from URL:https://pubs.acs.org/doi/pdf/10.1021/jo00216a030>.
Gypser, Andreas et al., "The solvent dependence of the diastereoselective hydrogenation of 2- and 2,5-substituted furylcarbinols on a Raney nickel contact", Synthesis, No. 3, Jan. 1, 1996, pp. 349-352.
Murali, Maluvadi G. et al., "Thiophene-based donor-acceptor conjugated polymer as potential optoelectronic and photonic material", Journal of Chemistry Science, Indian Academy of Sciences, Springer New Delhi, India, vol. 125, No. 2, Apr. 16, 2013, pp. 247-257.
Murashima, T. et al., "Highly Soluble Poly (1,3, 4-trisubstituted-2,5-pyrrolenevinylenes)", Tetrahedron Letters, Elsevier, Amsterdam, NL, vol. 39, No. 30, Jul. 23, 1998, pp. 5397-5400.
Niebel, Claude et al., "Bridged 3,3"-didodecylquaterthiophene-based dimers: design, synthesis, and optoelectronic properties", Tetrahedron, Elsevier, Science Publishers, Amsterdam, NL, vol. 68, No. 27, Apr. 19, 2012, pp. 5599-5605.
Extended European Search Report dated Feb. 18, 2022, issued in corresponding EP Patent Application No. 20763894.1.
Office action dated Nov. 15, 2023 from the IPO in a Indian patent application No. 202247000909 corresponding to the instant patent application.
Murayama et al., "Enantioselective Synthesis, Crystal Structure, and Photophysical Properties of a 1, 1 '-Bitriphenylene-Based Sila[7] helicene", Eur. J. Org. Chem., 2015, pp. 1409-1414.
Takahashi et al., "Evaluation of energy transfer in perylene-cored anthracene dendrimers", Chem. Commun., 2006, pp. 3084-3086.
Non-Final Office Action issued by USPTO on Sep. 14, 2023, in related U.S. Appl. No. 17/408,474.
English language translation of the following: Decision of Refusal dated Jun. 4, 2024 from the JPO in a Japanese patent application No. 2023-026563 corresponding to the instant patent application.
Office Action dated Jun. 27, 2024, issued by the EPO in corresponding EP Patent Application No. 20763669.7.
English language translation of the following: Office action dated Nov. 19, 2024 from the TIPO in a Taiwan patent application No. 109106390 corresponding to the instant patent application.
English language translation of the following: Office action dated Jan. 7, 2025 from the JPO in a Japanese patent application No. 2023-191159 corresponding to the instant patent application.
Non-Final Office Action issued by USPTO on Jan. 28, 2025, in related U.S. Appl. No. 17/408,474.
Non-Final Office Action issued by USPTO on Feb. 14, 2025, in related U.S. Appl. No. 17/558,540.
Non-Final Office Action issued by USPTO on Mar. 13, 2025, in related U.S. Appl. No. 17/679,104.
Machine translation of WO1997/032837A1, Sep. 12, 1997, pp. 1-59.
Ryall, R. P. et al. "Substituted Vitamin K Epoxide Analogues. New Competitive Inhibitors and Substrates of Vitamin K1 Epoxide Reductase" J. Med. Chem 1990, 33, 1790-1797 (Yer: 1990).
Non-Final Office Action issued by USPTO on Apr. 15, 2025, in related U.S. Appl. No. 17/558,540.

```
SEQUENCE LISTING

<160> NUMBER OF SEQ ID NOS: 8

<210> SEQ ID NO 1
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (3)..(3)
<223> OTHER INFORMATION: protected with triphenylmethyl
<220> FEATURE:
<221> NAME/KEY: MISC_FEATURE
<222> LOCATION: (5)..(5)
<223> OTHER INFORMATION: protected with t-butyl
<220> FEATURE:
<221> NAME/KEY: BINDING
<222> LOCATION: (7)..(7)
<223> OTHER INFORMATION: protective group is bound to C-terminal
<220> FEATURE:
<221> NAME/KEY: MISC_FEATURE
<222> LOCATION: (7)..(7)
<223> OTHER INFORMATION: protected with t-butyl

<400> SEQUENCE: 1

Gly Gly Asn Gly Asp Phe Glu
1               5

<210> SEQ ID NO 2
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (2)..(2)
<223> OTHER INFORMATION: protected with t-butyl
<220> FEATURE:
<221> NAME/KEY: BINDING
```

```
<222> LOCATION: (4)..(4)
<223> OTHER INFORMATION: IndoTAG is bound to C-terminal
<220> FEATURE:
<221> NAME/KEY: MISC_FEATURE
<222> LOCATION: (4)..(4)
<223> OTHER INFORMATION: protected with t-butyl

<400> SEQUENCE: 2

Gly Asp Phe Glu
1

<210> SEQ ID NO 3
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (1)..(1)
<223> OTHER INFORMATION: protected with triphenylmethyl
<220> FEATURE:
<221> NAME/KEY: MISC_FEATURE
<222> LOCATION: (3)..(3)
<223> OTHER INFORMATION: protected with t-butyl
<220> FEATURE:
<221> NAME/KEY: MISC_FEATURE
<222> LOCATION: (5)..(5)
<223> OTHER INFORMATION: protected with t-butyl
<220> FEATURE:
<221> NAME/KEY: BINDING
<222> LOCATION: (5)..(5)
<223> OTHER INFORMATION: IndoTAG is bound to C-terminal

<400> SEQUENCE: 3

Asn Gly Asp Phe Glu
1               5

<210> SEQ ID NO 4
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (3)..(3)
<223> OTHER INFORMATION: protected with triphenylmethyl
<220> FEATURE:
<221> NAME/KEY: MISC_FEATURE
<222> LOCATION: (5)..(5)
<223> OTHER INFORMATION: protected with t-butyl
<220> FEATURE:
<221> NAME/KEY: BINDING
<222> LOCATION: (7)..(7)
<223> OTHER INFORMATION: IndoTAG is bound to C-terminal
<220> FEATURE:
<221> NAME/KEY: MISC_FEATURE
<222> LOCATION: (7)..(7)
<223> OTHER INFORMATION: protected with t-butyl

<400> SEQUENCE: 4

Gly Gly Asn Gly Asp Phe Glu
1               5
```

-continued

```
<210> SEQ ID NO 5
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (3)..(3)
<223> OTHER INFORMATION: protected with triphenylmethyl
<220> FEATURE:
<221> NAME/KEY: MISC_FEATURE
<222> LOCATION: (5)..(5)
<223> OTHER INFORMATION: protected with t-butyl
<220> FEATURE:
<221> NAME/KEY: BINDING
<222> LOCATION: (7)..(7)
<223> OTHER INFORMATION: -OH is bound to C-terminal
<220> FEATURE:
<221> NAME/KEY: MISC_FEATURE
<222> LOCATION: (7)..(7)
<223> OTHER INFORMATION: protected with t-butyl

<400> SEQUENCE: 5

Gly Gly Asn Gly Asp Phe Glu
1               5

<210> SEQ ID NO 6
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (3)..(3)
<223> OTHER INFORMATION: protected with triphenylmethyl
<220> FEATURE:
<221> NAME/KEY: MISC_FEATURE
<222> LOCATION: (5)..(5)
<223> OTHER INFORMATION: protected with t-butyl
<220> FEATURE:
<221> NAME/KEY: BINDING
<222> LOCATION: (7)..(7)
<223> OTHER INFORMATION: BfTAG is bound to C-terminal
<220> FEATURE:
<221> NAME/KEY: MISC_FEATURE
<222> LOCATION: (7)..(7)
<223> OTHER INFORMATION: protected with t-butyl

<400> SEQUENCE: 6

Gly Gly Asn Gly Asp Phe Glu
1               5

<210> SEQ ID NO 7
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (1)..(2)
```

```
<223> OTHER INFORMATION: Xaa represents MeNle
<220> FEATURE:
<221> NAME/KEY: MISC_FEATURE
<222> LOCATION: (3)..(3)
<223> OTHER INFORMATION: protected with Pbf
<220> FEATURE:
<221> NAME/KEY: MISC_FEATURE
<222> LOCATION: (4)..(4)
<223> OTHER INFORMATION: protected with triphenylmethyl
<220> FEATURE:
<221> NAME/KEY: BINDING
<222> LOCATION: (5)..(5)
<223> OTHER INFORMATION: Amino group is bound to C-terminal

<400> SEQUENCE: 7

Xaa Xaa Arg Cys Gly
1               5

<210> SEQ ID NO 8
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: BINDING
<222> LOCATION: (1)..(1)
<223> OTHER INFORMATION: Fmoc is bound to N-terminal
<220> FEATURE:
<221> NAME/KEY: MISC_FEATURE
<222> LOCATION: (1)..(2)
<223> OTHER INFORMATION: Xaa represents MeNle
<220> FEATURE:
<221> NAME/KEY: MISC_FEATURE
<222> LOCATION: (3)..(3)
<223> OTHER INFORMATION: protected with Pbf
<220> FEATURE:
<221> NAME/KEY: MISC_FEATURE
<222> LOCATION: (4)..(4)
<223> OTHER INFORMATION: protected with triphenylmethyl
<220> FEATURE:
<221> NAME/KEY: BINDING
<222> LOCATION: (5)..(5)
<223> OTHER INFORMATION: -NH2-DMPIndoTAG is bound to C-terminal

<400> SEQUENCE: 8

Xaa Xaa Arg Cys Gly
1               5
```

METHOD FOR PRODUCING PEPTIDE COMPOUND, PROTECTIVE GROUP-FORMING REAGENT, AND AROMATIC HETEROCYCLIC COMPOUND

CROSS-REFERENCE TO RELATED APPLICATIONS

This application is a Continuation of International Application No. PCT/JP2020/007478, filed on Feb. 25, 2020, which claims priority to Japanese Patent Application No. 2019-035775, filed on Feb. 28, 2019, and Japanese Patent Application No. 2019-122489, filed on Jun. 28, 2019. The entire contents of these applications are incorporated herein by reference.

INCORPORATION OF SEQUENCE LISTING

The Sequence Listing associated with this application is provided in text format as a file entitled "FS-F08405-02_Seq_ST25.TXT", created on Aug. 25, 2023. The text file has a size of 5 kb and was filed via EFS-Web. The information in electronic format of the Sequence Listing is incorporated herein by reference in its entirety.

BACKGROUND OF THE INVENTION

1. Field of the Invention

The present disclosure relates to a method for producing a peptide compound, a protective group-forming reagent, and an aromatic heterocyclic compound.

2. Description of the Related Art

A method for producing peptide has been roughly divided into a solid phase method and a liquid phase method.

The solid phase method is advantageous in that isolation and purification after reaction can be performed by only washing resin. However, the solid phase method is associated with problems in that the reaction is essentially a heterogeneous phase reaction, a reaction agent or a reagent need to be used in excess to compensate for the low reactivity. In addition, tracing of the reaction and analysis of a reaction product supported by a carrier are difficult.

On the other hand, the liquid phase method is advantageous in that good reactivity is exhibited, and intermediate peptide can be purified by extraction and washing, isolation, and the like after a condensation reaction. However, the liquid phase method is associated with problems in that the production step is complicated because, in each step of coupling reaction and deprotection, an extraction and washing step with a nonpolar organic solvent and an acidic or basic aqueous solution, or an isolation and purification step such as crystallization is needed to remove a residual reagent or a by-product.

In addition, as a protective group-forming reagent in the related art, a di or trialkoxybenzyl alcohol compound disclosed in JP2000-44493A or JP2009-185063A is known.

SUMMARY OF THE INVENTION

An object to be achieved by an embodiment of the present invention is to provide a method for producing a peptide compound having an excellent deprotection rate.

An object to be achieved by another embodiment of the present invention is to provide a protective group-forming reagent having an excellent deprotection rate.

An object to be achieved by still another embodiment of the present invention is to provide a novel aromatic heterocyclic compound.

The methods for achieving the above-described objects include the following aspects.

<1> A method for producing a peptide compound, comprising:
   a step of using an aromatic heterocyclic compound represented by Formula (1).

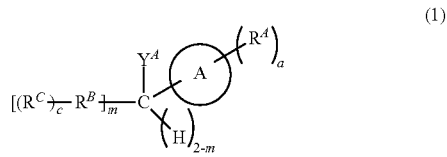

In Formula (1),
a ring A represents an aromatic heterocyclic ring,
$Y^A$ represents —OH, —NHR, SH, or —$X^0$, where R represents a hydrogen atom, an alkyl group, an aromatic group-substituted alkyl group, a heteroaromatic group-substituted alkyl group, or a 9-fluorenylmethoxycarbonyl group, and $X^0$ represents Cl, Br, or I,
$R^A$'s each independently represent an aliphatic hydrocarbon group or an organic group having an aliphatic hydrocarbon group, and the ring A may further have a substituent in addition to $R^A$,
$R^B$'s each independently represent a monovalent aliphatic hydrocarbon group, a (1+c)-valent aromatic group, or a (1+c)-valent heteroaromatic group,
$R^C$'s each independently represent an aliphatic hydrocarbon group or an organic group having an aliphatic hydrocarbon group,
m represents an integer of 0 to 2, a represents an integer of 0 to 5, and c represents an integer of 0 to 5,
in a case where both a and c are 0, $R^B$ is a monovalent aliphatic hydrocarbon group, and
the number of carbon atoms in at least one aliphatic hydrocarbon group of $R^A$, $R^B$, or $R^C$ is 12 or more.

<2> The method for producing a peptide compound according to <1>,
   in which the step of using the aromatic heterocyclic compound represented by Formula (1) is a C-terminal protecting step of protecting a carboxy group or an amide group of an amino acid compound or a peptide compound with the aromatic heterocyclic compound represented by Formula (1).

<3> The method for producing a peptide compound according to <2>,
   in which the amino acid compound or the peptide compound in the C-terminal protecting step is an N-terminal protected amino acid compound or an N-terminal protected peptide compound.

<4> The method for producing a peptide compound according to <3>, further comprising:
   an N-terminal deprotecting step of deprotecting an N-terminal end of an N-terminal and C-terminal protected amino acid compound or an N-terminal and C-terminal protected peptide compound, which is obtained in the C-terminal protecting step; and a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound.

<5> The method for producing a peptide compound according to <4>, further comprising:
a precipitating step of precipitating an N-terminal and C-terminal protected peptide compound obtained in the peptide chain extending step.

<6> The method for producing a peptide compound according to <5>, further comprising, one or more times in the following order after the precipitating step:
a step of deprotecting an N-terminal end of the obtained N-terminal and C-terminal protected peptide compound;
a step of condensing the N-terminal end of the obtained C-terminal protected peptide compound with an N-terminal protected amino acid compound or an N-terminal protected peptide compound; and
a step of precipitating the obtained N-terminal and C-terminal protected peptide compound.

<7> The method for producing a peptide compound according to any one of <1> to <6>, further comprising:
a C-terminal deprotecting step of deprotecting a C-terminal protective group.

<8> The method for producing a peptide compound according to any one of <1> to <7>,
in which the ring A is a pyrrole ring, an indole ring, a carbazole ring, a pyrazole ring, an indazole ring, a furan ring, a thiophene ring, a benzofuran ring, or a benzothiophene ring.

<9> The method for producing a peptide compound according to any one of <1> to <8>,
in which the ring A is represented by any of Formula (10), Formula (20), or Formula (30).

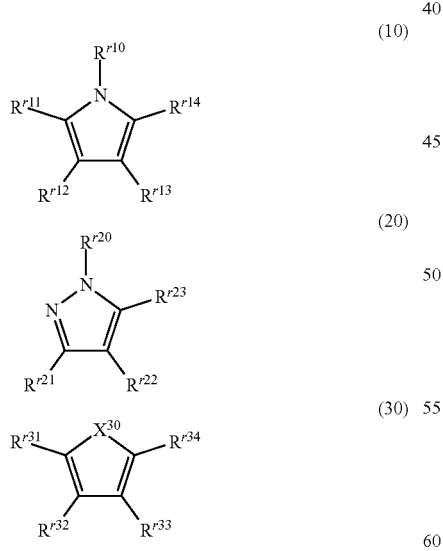

In Formula (10), any one of $R^{r10}$, $R^{r11}$, $R^{r12}$, $R^{r13}$, or $R^{r14}$ is linked to a group which includes a carbon atom having $Y^A$ in Formula (1), $R^{r10}$ represents a substituent or $R^A$, $R^{r11}$ to $R^{r14}$ each independently represent a hydrogen atom, a substituent, or $R^A$, and at least one of $R^{r10}$, $R^{r11}$, $R^{r12}$, $R^{r13}$, or $R^{r14}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r11}$ and $R^{r12}$, or $R^{r13}$ and $R^{r14}$ may be each independently linked to each other to form a ring.

In Formula (20), any one of $R^{r20}$, $R^{r21}$, $R^{r22}$, or $R^{r23}$ is linked to a group which includes a carbon atom having $Y^A$ in Formula (1), $R^{r20}$ represents a substituent or $R^A$, $R^{r21}$ to $R^{r23}$ each independently represent a hydrogen atom, a substituent, or $R^A$, and at least one of $R^{r20}$, $R^{r21}$, $R^{r22}$, or $R^{r23}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r22}$ and $R^{r23}$ may be linked to each other to form a ring.

In Formula (30), any one of $R^{r31}$, $R^{r32}$, $R^{r33}$, or $R^{r34}$ is linked to a group which includes a carbon atom having $Y^A$ in Formula (1), $X^{30}$ represents an oxygen atom or a sulfur atom, $R^{r31}$ to $R^{r34}$ each independently represent a hydrogen atom, a substituent, or $R^A$, and at least one of $R^{r31}$, $R^{r32}$, $R^{r33}$, or $R^{r34}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r31}$ and $R^{r32}$, or $R^{r33}$ and $R^{r34}$ may be each independently linked to each other to form a ring.

<10> The method for producing a peptide compound according to any one of <1> to <9>,
in which the number of carbon atoms in at least one aliphatic hydrocarbon group in at least one $R^A$ is 14 or more.

<11> The method for producing a peptide compound according to <9>,
in which the ring A represented by Formula (10) is represented by Formula (11),
a compound represented by Formula (20) is represented by Formula (21), and
a compound represented by Formula (30) is represented by Formula (31).

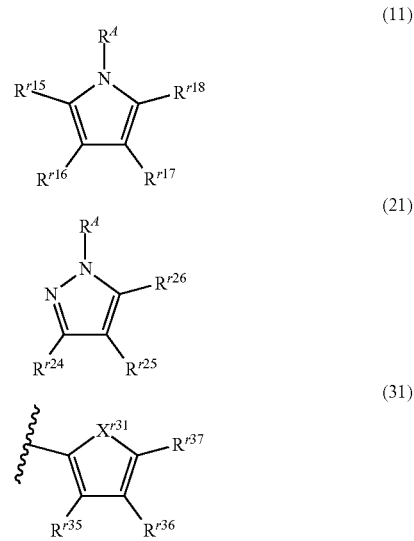

In Formula (11), any one of $R^{r15}$, $R^{r16}$, $R^{r17}$, or $R^{r18}$ is linked to the group which includes the carbon atom having $Y^A$ in Formula (1), $R^{r15}$ to $R^{r18}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r15}$ and $R^{r16}$, or $R^{r17}$ and $R^{r18}$ may be each independently linked to each other to form a ring.

In Formula (21), any one of $R^{r24}$, $R^{r25}$, or $R^{r26}$ is linked to the group which includes the carbon atom having $Y^A$ in Formula (1), $R^{r24}$ to $R^{r26}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r25}$ and $R^{r26}$ may be linked to each other to form a ring.

In Formula (31), a wavy line portion represents a position linked to the group which includes the carbon atom having $Y^A$ in Formula (1), $X^{r31}$ represents an oxygen atom or a sulfur atom, $R^{r35}$ to $R^{r37}$ each independently represent a hydrogen atom, a substituent, or $R^A$, $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, at least one of $R^{r35}$, $R^{r36}$ or $R^{r37}$ is $R^A$, and $R^{r36}$ and $R^{r37}$ may be linked to each other to form a ring.

<12> The method for producing a peptide compound according to any one of <1> to <11>,
in which a total number of carbon atoms in all aliphatic hydrocarbon groups included in all $R^A$'s is 40 or more.

<13> The method for producing a peptide compound according to any one of <1> to <12>,
in which $R^A$ is a group represented by Formula (f1) or a group represented by Formula (a1).

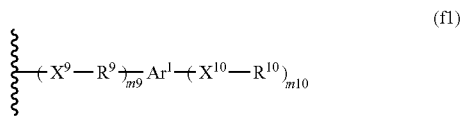

In Formula (f1), a wavy line portion represents a bonding position to an aromatic heterocyclic ring, m9 represents an integer of 0 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms.

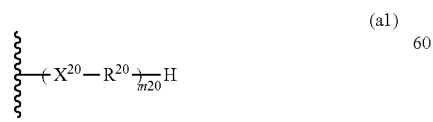

In Formula (a1), a wavy line portion represents a bonding position to an aromatic heterocyclic ring, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

<14> The method for producing a peptide compound according to <13>,
in which the group represented by Formula (f1) is a group represented by Formula (f2).

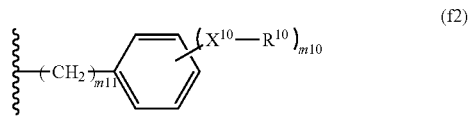

In Formula (f2), a wavy line portion represents a bonding position to an aromatic heterocyclic ring, m10 represents an integer of 1 to 3, m11 represents an integer of 0 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

<15> A protective group-forming reagent comprising:
an aromatic heterocyclic compound represented by Formula (1).

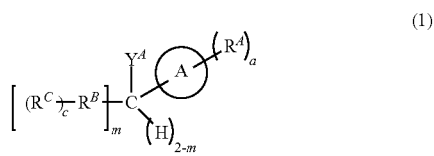

In Formula (1),
a ring A represents an aromatic heterocyclic ring,
$Y^A$ represents —OH, —NHR, SH, or —$X^0$, where R represents a hydrogen atom, an alkyl group, an aromatic group-substituted alkyl group, a heteroaromatic group-substituted alkyl group, or a 9-fluorenylmethoxycarbonyl group, and $X^0$ represents Cl, Br, or I,
$R^A$'s each independently represent an aliphatic hydrocarbon group or an organic group having an aliphatic hydrocarbon group, and the ring A may further have a substituent in addition to $R^A$,
$R^B$'s each independently represent a monovalent aliphatic hydrocarbon, a (1+c)-valent aromatic group, or a (1+c)-valent heteroaromatic group,
$R^C$'s each independently represent an aliphatic hydrocarbon group or an organic group having an aliphatic hydrocarbon group,
m represents an integer of 0 to 2, a represents an integer of 0 to 5, and c represents an integer of 0 to 5,
in a case where both a and c are 0, $R^B$ is a monovalent aliphatic hydrocarbon group, and
the number of carbon atoms in at least one aliphatic hydrocarbon group of $R^A$, $R^B$, or $R^C$ is 12 or more.

<16> The protective group-forming reagent according to <15>,
in which the protective group-forming reagent is a protective group-forming reagent of a carboxy group or an amide group.

<17> The protective group-forming reagent according to <15> or <16>, in which the protective group-forming reagent is a C-terminal protective group-forming reagent of an amino acid compound or a peptide compound.

<18> An aromatic heterocyclic compound represented by Formula (1a).

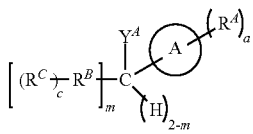
(1a)

In Formula (1a), a ring A represents an aromatic heterocyclic ring, $Y^A$ represents —OH, —NHR, SH, or —$X^O$, where R represents a hydrogen atom, an alkyl group, an aromatic group-substituted alkyl group, a heteroaromatic group-substituted alkyl group, or a 9-fluorenylmethoxycarbonyl group, and $X^O$ represents Cl, Br, or I, $R^A$'s each independently represent an aliphatic hydrocarbon group or an organic group having an aliphatic hydrocarbon group, and the ring A may further have a substituent in addition to $R^A$, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, the number of carbon atoms in at least one aliphatic hydrocarbon group included in at least one of $R^A$, $R^B$, or $R^C$ is 12 or more, and a total number of carbon atoms in all aliphatic hydrocarbon groups included in all $R^A$, $R^B$, and $R^C$ is 40 or more.

<19> The aromatic heterocyclic compound according to <18>, in which the ring A is represented by any of Formula (10a), Formula (20a), or Formula (30a).

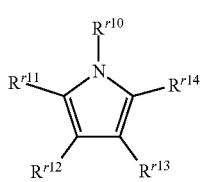
(10a)

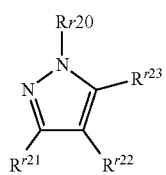
(20a)

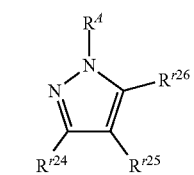
(30a)

In Formula (10a), any one of $R^{r10}$, $R^{r11}$, $R^{r12}$, $R^{r13}$, or $R^{r14}$ is linked to a group which includes a carbon atom having $Y^A$ in Formula (1a), $R^{r10}$ represents a substituent or $R^A$, $R^{r11}$ to $R^{r14}$ each independently represent a hydrogen atom, a substituent, or $R^A$, and at least one of $R^{r10}$, $R^{r11}$, $R^{r12}$, $R^{r13}$, or $R^{r14}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and $R^{r11}$ and $R^{r12}$, or $R^{r13}$ and $R^{r14}$ may be each independently linked to each other to form a ring.

In Formula (20a), any one of $R^{r20}$, $R^{r21}$, $R^{r22}$, or $R^{r23}$ is linked to a group which includes a carbon atom having $Y^A$ in Formula (1a), $R^{r20}$ represents a substituent or $R^A$, $R^{r21}$ to $R^{r23}$ each independently represent a hydrogen atom, a substituent, or $R^A$, and at least one of $R^{r20}$, $R^{r21}$, $R^{r22}$, or $R^{r23}$ is $R^A$, where $R^A$'s each independently represent an aliphatic hydrocarbon group or an organic group having an aliphatic hydrocarbon group, the number of carbon atoms in each aliphatic hydrocarbon group included in all $R^A$'s is 14 or more, and $R^{r22}$ and $R^{r23}$ may be linked to each other to form a ring.

In Formula (30a), any one of $R^{r31}$, $R^{r32}$, $R^{r33}$, or $R^{r34}$ is linked to a group which includes a carbon atom having $Y^A$ in Formula (1a), $X^{r30}$ represents an oxygen atom or a sulfur atom, $R^{r31}$ to $R^{r34}$ each independently represent a hydrogen atom, a substituent, or $R^A$, and at least one of $R^{r31}$, $R^{r32}$, $R^{r33}$, or $R^{r34}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and $R^{r31}$ and $R^{r32}$, or $R^{r33}$ and $R^{r34}$ may be each independently linked to each other to form a ring.

<20> The aromatic heterocyclic compound according to <18> or <19>, in which Formula (10a) is represented by Formula (11a), Formula (20a) is represented by Formula (21a), and Formula (30a) is represented by Formula (31a).

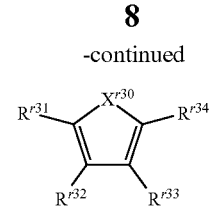
(11a)

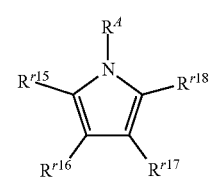
(21a)

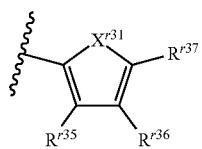
(31a)

In Formula (11a), any one of $R^{r15}$, $R^{r16}$, $R^{r17}$, or $R^{r18}$ is linked to the group which includes the carbon atom having $Y^A$ in Formula (1a), $R^{r15}$ to $R^{r18}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r15}$ and $R^{r16}$, or $R^{r17}$ and $R^{r18}$ may be each independently linked to each other to form a ring.

In Formula (21a), any one of $R^{r24}$, $R^{r25}$, or $R^{r26}$ is linked to the group which includes the carbon atom having $Y^A$ in Formula (1a), $R^{r24}$ to $R^{r26}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r25}$ and $R^{r26}$ may be linked to each other to form a ring.

In Formula (31a), a wavy line portion represents a position linked to the group which includes the carbon atom having $Y^A$ in Formula (1a), $X^{r31}$ represents an oxygen atom or a sulfur atom, $R^{r35}$ to $R^{r37}$ each independently represent a hydrogen atom, a substituent, or $R^A$, $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and at least one of $R^{r35}$, $R^{r36}$, or $R^{r37}$ is $R^A$ and may be linked to $R^{r36}$ to form a ring.

<21> The aromatic heterocyclic compound according to any one of <18> to <20>,
  in which a total number of carbon atoms in all aliphatic hydrocarbon groups included in all $R^A$, $R^B$, and $R^C$ is 40 to 80.

<22> The aromatic heterocyclic compound according to any one of <18> to <21>,
  in which $R^A$ is a group represented by Formula (f1) or a group represented by Formula (a1).

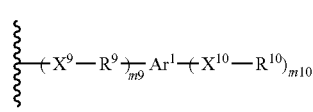
(f1)

In Formula (f1), a wavy line portion represents a bonding position to an aromatic heterocyclic ring, m9 represents an integer of 0 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms.

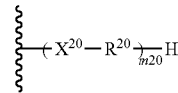
(a1)

In Formula (a1), a wavy line portion represents a bonding position to an aromatic heterocyclic ring, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

<23> The aromatic heterocyclic compound according to <22>,
  in which the group represented by Formula (f1) is a group represented by Formula (f2).

$$\{-(CH_2)_{m11}-\underset{\phantom{X}}{\bigcirc}-(X^{10}-R^{10})_{m10}\quad (f2)$$

In Formula (f2), a wavy line portion represents a bonding position to an aromatic heterocyclic ring, m10 represents an integer of 1 to 3, m11 represents an integer of 0 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

According to an embodiment of the present invention, it is possible to provide a method for producing a peptide compound having an excellent deprotection rate.

In addition, according to another embodiment of the present invention, it is possible to provide a protective group-forming reagent having an excellent deprotection rate.

In addition, according to still another embodiment of the present invention, it is possible to provide a novel aromatic heterocyclic compound.

DESCRIPTION OF THE PREFERRED EMBODIMENTS

Hereinafter, the contents of the present disclosure will be described in detail. The description of constituent elements below is made based on representative embodiments of the present disclosure in some cases, but the present disclosure is not limited to such embodiments.

In addition, in the present specification, a numerical range represented using "to" means a range including numerical values described before and after the preposition "to" as a lower limit value and an upper limit value.

In numerical ranges described in stages in the present specification, an upper limit value or a lower limit value described in one numerical range may be replaced with an upper limit value or a lower limit value of a numerical range described in another stage. In addition, in the numerical ranges described in the present specification, the upper limit value or the lower limit value of the numerical ranges may be replaced with the values shown in examples.

In the present specification, the term "step" includes not only the independent step but also a step in which intended purposes are achieved even in a case where the step cannot be precisely distinguished from other steps.

In a case where substitution or unsubstitution is not noted in regard to the notation of a "group" (atomic group) in the present specification, the "group" includes not only a group not having a substituent but also a group having a substituent. For example, the concept of an "alkyl group" includes not only an alkyl group not having a substituent (unsubstituted alkyl group) but also an alkyl group having a substituent (substituted alkyl group).

In addition, a chemical structural formula in the present specification may be described by a simplified structural formula in which hydrogen atoms are omitted.

In the present disclosure, "% by mass" has the same definition as that for "% by weight", and "part by mass" has the same definition as that for "part by weight".

In addition, in the present disclosure, a combination of two or more preferred aspects is a more preferred aspect.

In the present specification, an aromatic group and an aryl group are synonymous, and a heteroaromatic group and a heteroaryl group are synonymous. That is, an aromatic group-substituted alkyl group and an aryl group-substituted alkyl group are synonymous, and a heteroaromatic group-substituted alkyl group and a heteroaryl group-substituted alkyl group are synonymous.

(Method for Producing Peptide Compound)

The method for producing a peptide compound according to the embodiment of the present disclosure includes a step of using an aromatic heterocyclic compound represented by Formula (1) (hereinafter, also referred to as a compound represented by Formula (1)).

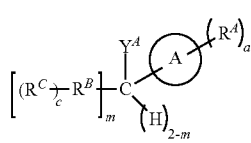

(1)

In Formula (1), a ring A represents an aromatic heterocyclic ring, $Y^A$ represents —OH, —NHR, SH, or —$X^O$, where R represents a hydrogen atom, an alkyl group, an aromatic group-substituted alkyl group, a heteroaromatic group-substituted alkyl group, or a 9-fluorenylmethoxycarbonyl group (hereinafter, also referred to as an Fmoc group), and $X^O$ represents Cl, Br, or I, $R^A$'s each independently represent an aliphatic hydrocarbon group or an organic group having an aliphatic hydrocarbon group, and the ring A may further have a substituent in addition to $R^A$, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, and the number of carbon atoms in at least one aliphatic hydrocarbon group of $R^A$, $R^B$, or $R^C$ is 12 or more.

The detailed mechanism by which a peptide compound having an excellent yield can be obtained with the method for producing a peptide compound according to the embodiment of the present disclosure, which includes the step of using the compound represented by Formula (1) is not clear, but it is presumed as follows.

Since the compound represented by Formula (1) according to the present disclosure has a faster deprotection rate than a benzyl alcohol-type protective group-forming reagent in the related art, it is presumed that the yield of the peptide compound to be obtained, or the like is excellent. It is considered that the reason why the deprotection rate is excellent is that the aromatic heterocyclic ring is superior in electron donating property to benzyl alcohol. In the present specification, it can be said that, as the deprotection rate is high, the deprotection rate is excellent.

In addition, in a case where the compound represented by Formula (1) is used as a C-terminal protective group of peptide, the deprotection rate is superior to that in a case where a benzyl alcohol-type protective group-forming reagent in the related art is used. For example, it is possible to selectively deprotect only the C-terminal protective group while leaving a protective group of an amino acid side chain, that is, to distinguish the side chain protective group from each amino acid. It can also be used for subsequent reactions such as a condensation reaction of a fragment of a long-chain peptide with the deprotected C-terminal end. In addition, in a case of peptide which is unstable to a strong acid, decomposition of a peptide chain can be suppressed, which leads to an improvement in yield. In addition, it is suitable for the synthesis of peptide which is unstable to acid because of its excellent deprotection rate with acid.

Since, in the compound represented by Formula (1), the number of carbon atoms in at least one aliphatic hydrocarbon group included in at least one of $R^A$, $R^B$, or $R^C$ is 12 or more, a compound protected by the compound represented by Formula (1) has excellent solubility in a hydrophobic solvent. Further, with regard to a hydrophilic solvent, since the aliphatic hydrocarbon groups in each $R^A$, $R^B$, and $R^C$ aggregate with each other intramolecularly and intermolecularly and the compound represented by Formula (1) has an aromatic heterocyclic ring, due to the π-π interaction (π-π stacking) between the aromatic heterocyclic rings, crystallization property is excellent, and purification and separability are also excellent. In other words, since a compound protected by the compound represented by Formula (1) has excellent solubility in a hydrophobic solvent as a reaction solvent, it is presumed that the reaction proceeds rapidly, and since a target product is efficiently crystallized and purified by adding a polar solvent which is a poor solvent during purification, it is presumed that yield of the obtained compound (peptide compound and the like) is excellent.

The above-described effects are more excellent in a case where the number of carbon atoms in at least one aliphatic hydrocarbon group included in at least one of $R^A$, $R^B$, or $R^C$ is preferably 14 or more. The reason is not clear, but is presumed that, as the number of carbon atoms in any of $R^A$, $R^B$, or $R^C$ increases, the contribution ratio of hydrophobicity in the entire molecule represented by Formula (1) increases, which makes it easier to dissolve in a hydrophobic solvent, and with regard to a hydrophilic solvent, presumed that, as the number of carbon atoms increases, the cohesive force increases, which makes it easier to be crystallized.

Further, since the aromatic heterocyclic compound represented by Formula (1) according to the present disclosure has the above-described structure, the aromatic heterocyclic compound represented by Formula (1) is stable during a peptide synthesis reaction, but deprotection (removal) is easy.

Furthermore, by using the aromatic heterocyclic compound represented by Formula (1) according to the present disclosure, even poorly synthesized peptides such as unnatural peptide including unnatural amino acid, in which a side reaction is likely to occur, the peptide can be synthesized with high purity due to suppression of the side reaction.

In the present disclosure, the C-terminal protective group can be deprotected even under weak acid conditions, and a side reaction of the obtained peptide can be suppressed.

Examples of peptide which is suitable for deprotection of the C-terminal protective group under weak acid conditions (that is, peptide which is sensitive to acid) include peptides having an N-alkylamide structure.

From the viewpoint of suppressing side reactions of the obtained peptide and of temporal stability, the method for producing a peptide compound according to the embodiment of the present disclosure is preferably used for a method for producing a peptide compound which is sensitive to acid, more preferably used for a method for producing a peptide compound having an N-alkylamide structure.

Hereinafter, the aromatic heterocyclic compound represented by Formula (1), which is used in the method for producing a peptide compound according to the embodiment of the present disclosure will be described in detail.

In the method for producing a peptide compound according to the embodiment of the present disclosure, the aromatic heterocyclic compound represented by Formula (1) can be used not only for formation of a protective group, but also for denaturation of a peptide compound, adjustment of solubility in water or an organic solvent, improvement of crystallinity, multimerization, and the like.

Among these, the aromatic heterocyclic compound represented by Formula (1) is preferably used for formation of a protective group, and more preferably used for forming a C-terminal protective group in an amino acid compound or a peptide compound.

<Aromatic Heterocyclic Compound Represented by Formula (1)>

The aromatic heterocyclic compound represented by Formula (1) according to the present disclosure is shown below.

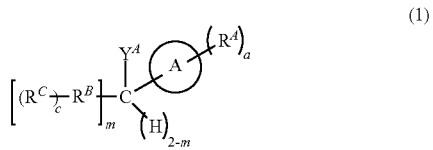

(1)

In Formula (1), the ring A, $Y^A$, $R^A$, $R^B$, $R^C$, m, a, and c have the same meanings as described above.

The ring A in Formula (1) represents an aromatic heterocyclic ring, and the ring A may further have a substituent in addition to the methylene group in which $Y^A$ and $R^B$ are linked and $R^A$.

From the viewpoint of deprotection rate, crystallization property, and yield, the aromatic heterocyclic compound is preferably an aromatic heterocyclic compound which does not have an SH group, an amino group, an OH group, or a COOH group, other than $Y^A$.

The ring A may be either a monocyclic or polycyclic heterocyclic ring.

In a case where the ring A is polycyclic, it is preferable to be a condensed polycyclic aromatic heterocyclic ring having 2 or more rings in which aromatic heterocyclic rings are condensed, it is more preferable to be a condensed polycyclic aromatic heterocyclic ring having 2 to 4 rings, and it is still more preferable to be a condensed polycyclic aromatic heterocyclic ring having 2 or 3 rings.

In addition, it is preferable that the ring A is a heterocyclic ring having at least one hetero atom selected from the group consisting of a nitrogen atom, an oxygen atom, or a sulfur atom, it is more preferable that the ring A has at least one hetero atom selected from the group consisting of a nitrogen atom and a sulfur atom, it is still more preferable that the ring A includes a nitrogen atom or a sulfur atom, and it is particularly preferable that the ring A includes a nitrogen atom.

In the ring A, from the viewpoint of deprotection rate, crystallization property, and yield, in a case where the above-described hetero atom is a nitrogen atom, it is preferable that the nitrogen atom further has a substituent. Suitable examples of the substituent include $R^A$ in Formula (1) described above, and the preferred aspect is also the same.

The number of ring members in the ring A is not particularly limited, but is preferably 5 to 8 and more preferably 5 or 6.

From the viewpoint of deprotection rate, crystallization property, and yield, the ring A is preferably a 5-membered to 8-membered aromatic heterocyclic ring, more preferably a 5-membered or 6-membered aromatic heterocyclic ring, still more preferably a two- or three-ring condensed polycyclic aromatic heterocyclic ring which includes a 5-membered or 6-membered ring having at least one hetero atom selected from the group consisting of a nitrogen atom and a sulfur atom, and particularly preferably a two- or three-ring condensed polycyclic aromatic heterocyclic ring which includes a 5-membered or 6-membered ring having a nitrogen atom or a sulfur atom.

Among these, from the viewpoint of deprotection rate, crystallization property, and yield, the ring A is preferably a benzothiophene ring, a furan ring, a benzofuran ring, a pyrrole ring, an indole ring, a carbazole ring, a pyrazole ring, an indazole ring, or a thiophene ring, more preferably a benzothiophene ring, a furan ring, a benzofuran ring, an indole ring, a carbazole ring, an indazole ring, or a thiophene ring, still more preferably a benzofuran ring, an indole ring, a carbazole ring, or a thiophene ring, and particularly preferably a benzofuran ring, an indole ring, or a carbazole ring.

In a case where a C-terminal end of peptide to be protected is an amide, an indole ring is preferable, and in a case where a C-terminal end of peptide to be protected is a carboxylic acid, a benzofuran ring is preferable.

From the viewpoint of deprotection rate, crystallization property, and yield, it is preferable that a nitrogen atom at the 1-position on the pyrrole ring, indole ring, carbazole ring, pyrazole ring, of indazole ring has a substituent. Suitable examples of the substituent include $R^A$ in Formula (1) described above, and the preferred aspect is also the same.

In addition, from the viewpoint of yield, the ring A is preferably a two- or three-ring condensed polycyclic aromatic heterocyclic ring which includes a 5-membered ring having a nitrogen atom, and more preferably an indole ring or a carbazole ring.

Furthermore, the ring A may have a substituent, and as described later, may form a ring structure in which two or more substituents are bonded to each other, and the ring A may have a structure in which an aliphatic hydrocarbon ring, a polycyclic aromatic hydrocarbon ring, an aliphatic heterocyclic ring, or the like is further fused.

[$Y^A$]

From the viewpoint of deprotection rate, solubility in a solvent, and yield, $Y^A$ in Formula (1) is preferably —OH, —NHR, or —SH, and more preferably —OH or —NHR.

Examples of the alkyl group in R include an alkyl group having 1 to 30 carbon atoms (also referred to as "the number of carbon atoms"), and an alkyl group having 1 to 10 carbon atoms is preferable and an alkyl group having 1 to 6 carbon atoms is more preferable. Suitable specific examples thereof include a methyl group, an ethyl group, a propyl group, an isopropyl group, an n-butyl group, an isobutyl group, a sec-butyl group, a tert-butyl group, a pentyl group, and a hexyl group, and a methyl group or an ethyl group is more preferable.

Examples of the aromatic group-substituted alkyl group in R include an aromatic group-substituted alkyl group having 7 to 30 carbon atoms, and an aromatic group-substituted alkyl group having 7 to 20 carbon atoms is preferable and an aralkyl group having 7 to 16 carbon atoms (for example, a group in which an alkylene group having 1 to 6 carbon atoms is bonded to an aromatic group having 6 to 10 carbon atoms) is more preferable. Suitable specific examples thereof include a benzyl group, a 1-phenylethyl group, a 2-phenylethyl group, a 1-phenylpropyl group, a naphthylmethyl group, a 1-naphthylethyl group, and a 1-naphthylpropyl group, and a benzyl group is more preferable.

Examples of the heteroaromatic group-substituted alkyl group in R include a heteroaromatic group-substituted alkyl group having 5 to 30 carbon atoms, and a heteroaromatic group-substituted alkyl group having 5 to 20 carbon atoms is preferable and a heteroaromatic group-substituted alkyl group having 5 to 16 carbon atoms (for example, a group in which an alkylene group having 1 to 6 carbon atoms is bonded to a heteroaromatic group having 4 to 10 carbon atoms) is more preferable. Suitable specific examples thereof include an indolylmethyl group, a furfuryl group, a benzofuranylmethyl group, a thiophenylmethyl group, and a benzothiophenylmethyl group.

Among these, R is preferably a hydrogen atom, an alkyl group having 1 to 6 carbon atoms, an aromatic group-substituted alkyl group having 7 to 16 carbon atoms, or an Fmoc group, more preferably a hydrogen atom, a methyl group, an ethyl group, a benzyl group, or a Fmoc group, and still more preferably a hydrogen atom or an Fmoc group.

In a case where R is an Fmoc group, since $Y^A$ becomes —NH$_2$ by deprotecting the Fmoc group with a base such as 1,8-diazabicyclo[5.4.0]-7-undecene (DBU) described later, it can be considered that the case where R is an Fmoc group and the case where R is a hydrogen atom are equivalent.

In addition, as the above-described substituent on the ring A, the substituent on $R^B$, or $R^A$, the compound represented by Formula (1) may have a group which has the ring A having the methylene group in which $Y^A$ and $R^B$ are linked, or a group which has the ring A having the methylene group in which $Y^A$ and $R^B$ are linked, and $Y^A$. That is, the compound represented by Formula (1) may be a multimer such as a dimer. From the viewpoint of ease of synthesis, the multimer is preferably a dimer to a hexamer, more preferably a dimer to a tetramer, and particularly preferably a dimer.

From the viewpoint of deprotection rate, solubility in a solvent, and yield, a, which is the number of substitutions of $R^A$ on the ring A in Formula (1), is preferably an integer of 1 to 4, more preferably an integer of 1 to 3, and particularly preferably 1 or 2.

In addition, from the viewpoint of deprotection rate, solubility in a solvent, and yield, c, which is the number of substitutions of $R^C$ on $R^B$ in Formula (1), is preferably an integer of 0 to 4, more preferably an integer of 0 to 2, still more preferably 0 or 1, and particularly preferably 0.

Furthermore, from the viewpoint of deprotection rate, solubility in a solvent, and yield, the value of a+c in Formula (1) is preferably 0 or more, more preferably an integer of 1 to 6, still more preferably an integer of 1 to 4, particularly preferably 1 to 3, and most preferably 1.

[$R^A$ and $R^C$]

$R^A$'s each independently represent an aliphatic hydrocarbon group or an organic group having an aliphatic hydrocarbon group.

In addition, $R^C$'s each independently represent an aliphatic hydrocarbon group or an organic group having an aliphatic hydrocarbon group.

The "aliphatic hydrocarbon group" is a linear, branched, or cyclic saturated or unsaturated aliphatic hydrocarbon group, and an aliphatic hydrocarbon group having 5 or more carbon atoms is preferable, an aliphatic hydrocarbon group having 5 to 60 carbon atoms is more preferable, an aliphatic hydrocarbon group having 5 to 30 carbon atoms is still more preferable, and an aliphatic hydrocarbon group having 10 to 30 carbon atoms is particularly preferable.

In addition, from the viewpoint of solubility in a solvent, crystallization property, and yield, the number of carbon atoms in the "aliphatic hydrocarbon group" is preferably 12 or more, more preferably 14 or more, still more preferably 16 or more, and particularly preferably 18 or more.

The moiety of the "aliphatic hydrocarbon group" in the "organic group having an aliphatic hydrocarbon group" is not particularly limited, and may be present at the terminal (a monovalent group) or may be present at any other site (for example, a divalent group).

In the present specification, the "organic group having an aliphatic hydrocarbon group" is a monovalent (one bonding site bonded to the ring A) organic group having an aliphatic hydrocarbon group in its molecular structure.

The moiety of the "aliphatic hydrocarbon group" in the "organic group having an aliphatic hydrocarbon group" is not particularly limited, and may be present at the terminal (a monovalent group) or may be present at any other site (for example, a divalent group).

Examples of the "aliphatic hydrocarbon group" include an alkyl group, a cycloalkyl group, an alkenyl group, and an alkynyl group.

Specific examples thereof include monovalent groups such as a pentyl group, a hexyl group, an octyl group, a decyl group, a hexadecyl group, an octadecyl group, an icosyl group, a docosyl group, a tetracosyl group, a lauryl group, a tridecyl group, a myristyl group, an oleyl group, and an isostearyl group; divalent groups derived from these (divalent groups obtained by removing one hydrogen atom from the monovalent groups); and groups removing a hydroxy group or the like from various steroid groups.

As the "alkyl group", an alkyl group having 5 to 30 carbon atoms is preferable, and examples thereof include a pentyl group, a hexyl group, an octyl group, a 2-ethylhexyl group, a decyl group, a hexadecyl group, an octadecyl group, an icosyl group, a docosyl group, a tetracosyl group, a lauryl group, a tridecyl group, a myristyl group, and an isostearyl group. Among these, an octadecyl group, an icosyl group, a docosyl group, or a tetracosyl group is preferable, and an icosyl group, a docosyl group, or a tetracosyl group is more preferable.

As the "cycloalkyl group", a cycloalkyl group having 5 to 30 carbon atoms is preferable, and examples thereof include a cyclopentyl group, a cyclohexyl group, an isobornyl group, and a tricyclodecanyl group. In addition, these may be linked repeatedly, or may be a fused-ring structure of two or more rings.

As the "alkenyl group", an alkenyl group having 5 to 30 carbon atoms is preferable, and examples thereof include a pentenyl group, a hexenyl group, and an oleyl group.

As the "alkynyl group", an alkynyl group having 5 to 30 carbon atoms is preferable, and examples thereof include a 4-pentynyl group and a 5-hexenyl group.

As the "steroid group", for example, a group having a cholesterol structure, a group having an estradiol structure, or the like is preferable.

The above-described organic group may be further substituted with a silyl group, a hydrocarbon group having a silyloxy structure, or an organic group having a perfluoroalkyl structure.

As the above-described silyl group, a trialkylsilyl group is preferable, and a silyl group having three alkyl groups having 1 to 3 carbon atoms is more preferable.

As the silyloxy structure in the above-described hydrocarbon group having a silyloxy structure, a trialkylsilyloxy structure is preferable, and a silyloxy structure having three alkyl groups having 1 to 3 carbon atoms is more preferable.

In addition, the above-described hydrocarbon group having a silyloxy structure preferably has 1 to 3 silyloxy structures.

Furthermore, the number of carbon atoms in the above-described hydrocarbon group having a silyloxy structure is preferably 10 or more, more preferably 10 to 100, and particularly preferably 16 to 50.

Preferred examples of the above-described hydrocarbon group having a silyloxy structure include a group represented by Formula (Si).

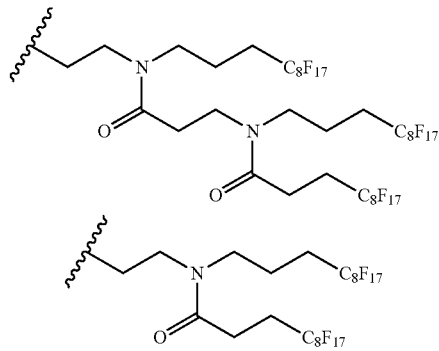

In Formula (Si), $R^{si1}$ represents a single bond or an alkylene group having 1 to 3 carbon atoms, $R^{si2}$ represents an alkylene group having 1 to 3 carbon atoms, $R^{si3}$ and $R^{si4}$ each independently represent a hydrogen atom, an alkyl group having 1 to 6 carbon atoms, or —$OSiR^{si5}R^{si6}R^{si7}$, and $R^{si5}$ to $R^{si7}$ each independently represent an alkyl group having 1 to 6 carbon atoms or an aryl group.

$R^{si5}$ to $R^{si7}$ in Formula (Si) are each independently preferably an alkyl group having 1 to 6 carbon atoms or a phenyl group, more preferably an alkyl group having 1 to 6 carbon atoms, and particularly preferably a linear or branched alkyl group having 1 to 4 carbon atoms.

As the perfluoroalkyl structure in the above-described organic group having a perfluoroalkyl structure, a perfluoroalkyl structure having 1 to 20 carbon atoms is preferable, a perfluoroalkyl structure having 5 to 20 carbon atoms is more preferable, and a perfluoroalkyl structure having 7 to 16 carbon atoms is particularly preferable. In addition, the above-described perfluoroalkyl structure may be linear, may have a branch, or may have a ring structure.

The above-described organic group having a perfluoroalkyl structure is preferably a perfluoroalkyl group, an alkyl group having a perfluoroalkyl structure, or an alkyl group having a perfluoroalkyl structure and an amide bond in the alkyl chain.

The number of carbon atoms in the above-described organic group having a perfluoroalkyl structure is preferably 5 or more, more preferably 10 or more, still more preferably 10 to 100, and particularly preferably 16 to 50.

Preferred examples of the above-described organic group having a perfluoroalkyl structure include groups shown below.

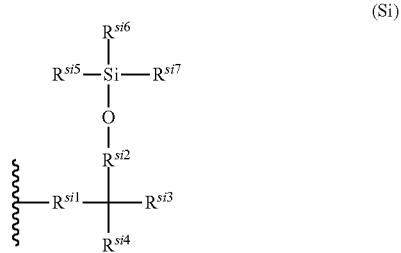

A moiety other than the "aliphatic hydrocarbon group" in the "organic group having an aliphatic hydrocarbon group" can be optionally set. For example, the "organic group having an aliphatic hydrocarbon group" may have a moiety such as —O—, —S—, —COO—, —OCONH—, —CONH—, and a hydrocarbon group (monovalent group or divalent group) other than the "aliphatic hydrocarbon group".

Examples of the "hydrocarbon group" other than the "aliphatic hydrocarbon group" include an aromatic hydrocarbon group, and specifically, for example, a monovalent group such as an aryl group or a divalent group derived from the monovalent group is used.

As the "aryl group", an aryl group having 6 to 14 carbon atoms is preferable, and examples thereof include a phenyl group, a 1-naphthyl group, a 2-naphthyl group, a biphenylyl group, and a 2-anthryl group. Among these, an aryl group having 6 to 10 carbon atoms is more preferable, and a phenyl group is particularly preferable.

In addition, the above-described aliphatic hydrocarbon group and the hydrocarbon group other than the above-described aliphatic hydrocarbon group may be substituted with a substituent selected from a halogen atom (chlorine atom, bromine atom, fluorine atom, or iodine atom), an oxo group, and the like.

In $R^A$ described above, the bond (substitution) of the organic group having an aliphatic hydrocarbon group to the ring A may be through the above-described aliphatic hydrocarbon group or the above-described hydrocarbon group existing in $R^A$, that is, may be directly bonded by a carbon-carbon bond or may be bonded by a carbon-nitrogen bond, or may be through a moiety such as —O—, —S—, —COO—, —OCONH—, and —CONH—, which exists in $R^A$.

From the viewpoint of ease of synthesizing the compound, it is preferable to be through a carbon-carbon bond, a carbon-nitrogen bond, —O—, —S—, —COO—, or —CONH—, and it is more preferable to be through a carbon-carbon bond, a carbon-nitrogen bond, or —O—.

In a case where the ring A is a ring having an oxygen atom or a sulfur atom, it is preferable that the bond (substitution) of the organic group having an aliphatic hydrocarbon group to the ring A is through —O—.

In a case where the ring A is a ring having a nitrogen atom, it is preferable that the bond (substitution) of the organic group having an aliphatic hydrocarbon group to the ring A is through a direct carbon-nitrogen bond.

In the compound represented by Formula (1) according to the present disclosure, from the viewpoint of solubility in a solvent, crystallization property, and yield, the total number of carbon atoms in all aliphatic hydrocarbon groups included in all $R^A$, $R^B$, and $R^C$ is preferably 24 or more, more preferably 24 to 200, still more preferably 32 to 100, particularly preferably 34 to 80, and most preferably 36 to 80.

In addition, in the compound represented by Formula (1) according to the present disclosure, from the viewpoint of solubility in a solvent, crystallization property, and yield, the total number of carbon atoms in all aliphatic hydrocarbon groups included in all $R^A$'s is preferably 24 or more, more preferably 24 to 200, still more preferably 32 to 100, particularly preferably 34 to 80, and most preferably 36 to 80.

In addition, the compound represented by Formula (1) according to the present disclosure is a compound in which the number of carbon atoms in at least one aliphatic hydrocarbon group included in at least one of $R^A$, $R^B$, or $R^C$ is 12 or more, and from the viewpoint of solubility in a solvent, crystallization property, and yield, it is preferable to be a compound having at least one aliphatic hydrocarbon group having 12 or more carbon atoms in at least one $R^A$ or $R^C$, more preferable to be a compound having at least one aliphatic hydrocarbon group having 12 to 100 carbon atoms in at least one $R^A$, still more preferable to be a compound having at least one aliphatic hydrocarbon group having 18 to 40 carbon atoms in at least one $R^A$, and particularly preferable to be a compound having at least one aliphatic hydrocarbon group having 20 to 36 carbon atoms in at least one $R^A$.

In the compound represented by Formula (1) according to the present disclosure, the above-described effects are more excellent in a case where the number of carbon atoms in at least one aliphatic hydrocarbon group in $R^A$, $R^B$, or $R^C$ is preferably 14 or more, more preferably 16 or more, still more preferably 18 or more, and particularly preferably 20 or more. The reason is considered that, as the number of carbon atoms increases, the contribution ratio of hydrophobicity in the entire molecule increases, which makes it easier to dissolve in a hydrophobic solvent, and with regard to a hydrophilic solvent, presumed that, as the number of carbon atoms increases, the cohesive force increases, which makes it easier to be crystallized.

Furthermore, from the viewpoint of crystallization property and yield, the above-described aliphatic hydrocarbon group is preferably an alkyl group and more preferably a linear alkyl group.

In addition, from the viewpoint of solubility in a solvent, crystallization property, and yield, the number of carbon atoms in one $R^A$, $R^B$, or $R^C$ is preferably 12 to 200, more preferably 18 to 150, still more preferably 18 to 100, and particularly preferably 20 to 80, respectively.

In the compound represented by Formula (1) according to the present disclosure, from the viewpoint of solubility in a solvent, crystallization property, and yield, the total number of carbon atoms in all aliphatic hydrocarbon groups included in $R^A$, $R^B$, or $R^C$ is preferably 24 or more, more preferably 32 to 200, still more preferably 38 to 100, and particularly preferably 40 to 80.

Furthermore, the aliphatic hydrocarbon group having 12 or more carbon atoms included in the compound represented by Formula (1) according to the present disclosure is included in at least one of $R^A$, $R^B$, or $R^C$, and from the viewpoint of solubility in a solvent, crystallization property, and yield, it is preferable to be included in at least one of $R^A$ or $R^C$ and it is more preferable to be included in at least one of $R^A$'s.

m in Formula (1) represents an integer of 0 to 2. From the viewpoint of yield and compound stability of peptide condensate, m is preferably 0 or 1. In addition, from the viewpoint of deprotection rate, m in Formula (1) is preferably 1 or 2.

In addition, in a case where $Y^A$ in Formula (1) is —NHR and R is a hydrogen atom, from the viewpoint of deprotection rate, m in Formula (1) is preferably 1 or 2 and more preferably 1.

In addition, in a case where $Y^A$ in Formula (1) is —NHR and R is a substituent other than a hydrogen atom, from the viewpoint of deprotection rate, m in Formula (1) is preferably 0 or 1 and more preferably 0.

In addition, in a case where $Y^A$ in Formula (1) is —OH, from the viewpoint of deprotection rate, m in Formula (1) is preferably 0 or 1 and more preferably 0.

[$R^B$]

From the viewpoint of solubility in a solvent, crystallization property, and yield, $R^B$'s in Formula (1) are each independently preferably a monovalent aliphatic hydrocarbon group or a (1+c)-valent aromatic group, more preferably a monovalent alkyl group having 1 to 30 carbon atoms or a (1+c)-valent aromatic group having 6 to 30 carbon atoms, still more preferably a monovalent alkyl group having 1 to 26 carbon atoms or a (1+c)-valent aromatic group having 6 to 20 carbon atoms, and particularly preferably a monovalent alkyl group having 1 to 22 carbon atoms or a (1+c)-valent aromatic group having 6 to 10 carbon atoms.

The monovalent alkyl group, (1+c)-valent aromatic group, and (1+c)-valent heteroaromatic group in $R^B$ may have a substituent. The above-described substituent is not particularly limited, and examples thereof include an alkoxy group, an aryloxy group, a halogen atom, an alkyl group, a halogenated alkyl group, an aryl group, an acyl group, an acyloxy group, an alkoxycarbonyl group, an aryloxycarbonyl group, an alkylthio group, an arylthio group, $R^{st}$—CO—NR$^{st}$—, —CON($R^{st}$)$_2$, a dialkylamino group, an alkylarylamino group, a diarylamino group, and a group obtained by combining two or more of these groups. $R^{st}$ represents a hydrogen atom, an alkyl group, or an aryl group.

Examples of the monovalent aliphatic hydrocarbon group in $R^B$ include a methyl group, a trifluoromethyl group, an ethyl group, a propyl group, an isopropyl group, a butyl group, an isobutyl group, a sec-butyl group, a tert-butyl group, a pentyl group, a hexyl group, an octyl group, a 2-ethylhexyl group, a decyl group, a hexadecyl group, an octadecyl group, an icosyl group, a docosyl group, a tetracosyl group, a lauryl group, a tridecyl group, a myristyl group, and an isostearyl group.

Examples of the (1+c)-valent aromatic group in $R^B$ include a phenyl group, a fluorophenyl group, a difluorophenyl group, a chlorophenyl group, a dichlorophenyl group, a trichlorophenyl group, a methylphenyl group (tolyl group), a dimethylphenyl group (xylyl group), a methoxyphenyl group, a dimethoxyphenyl group, a trimethoxyphenyl group, a phenylene group, a benzenetriyl group, a 1-naphthyl group, a 2-naphthyl group, a naphthylene group, a naphthalenetriyl group.

Among these, in a case where m is 1 or 2 and $Y^A$ is —OH, from the viewpoint of compound stability of peptide condensate, a phenyl group, a fluorophenyl group, a difluorophenyl group, a chlorophenyl group, a dichlorophenyl group, or a trichlorophenyl group is preferable, and a fluorophenyl group, a difluorophenyl group, a chlorophenyl group, a dichlorophenyl group, or a trichlorophenyl group is more preferable.

In a case where m is 1 and $Y^A$ is —NHR, from the viewpoint of deprotection rate, a phenyl group, a methylphenyl group (tolyl group), a dimethylphenyl group (xylyl group), a methoxyphenyl group, a dimethoxyphenyl group, or a trimethoxyphenyl group is preferable, and a methylphenyl group (tolyl group), a dimethylphenyl group (xylyl group), a methoxyphenyl group, a dimethoxyphenyl group, or a trimethoxyphenyl group is more preferable.

In a case where m is 2 and $Y^A$ is —NHR, from the viewpoint of compound stability of peptide condensate, a phenyl group, a fluorophenyl group, a difluorophenyl group, a chlorophenyl group, a dichlorophenyl group, or a trichlorophenyl group is preferable, and a fluorophenyl group, a difluorophenyl group, a chlorophenyl group, a dichlorophenyl group, or a trichlorophenyl group is more preferable.

Examples of the (1+c)-valent heteroaromatic group in $R^B$ include a monocyclic nitrogen-containing heteroaromatic group, a monocyclic oxygen-containing heteroaromatic group, a monocyclic sulfur-containing heteroaromatic group, a monocyclic nitrogen and oxygen-containing heteroaromatic group, a monocyclic nitrogen and sulfur-containing heteroaromatic group, a bicyclic nitrogen-containing heteroaromatic group, a bicyclic oxygen-containing heteroaromatic group, a bicyclic sulfur-containing heteroaromatic group, a bicyclic nitrogen-containing heteroaromatic group, a bicyclic nitrogen and oxygen-containing heteroaromatic group, and a bicyclic nitrogen and sulfur-containing heteroaromatic group, which are (1+c)-valent. Specific examples thereof include a pyridyl group, a furanyl group, a thienyl group, a pyrrolyl group, an oxazolyl group, an imidazolyl group, a pyrazolyl group, a triazolyl group, a tetrazolyl group, a pyridinediyl group, a pyridinetriyl group, a furandiyl group, a thiophendiyl group, a pyrroldiyl group, a benzofrangyl group, a benzothipheneyl group, and an indoldiyl group.

In Formula (1), from the viewpoint of solubility in a solvent, crystallization property, and yield, it is preferable that at least one $R^A$ or $R^C$ is a group represented by any of Formula (f1), Formula (a1), Formula (b1), or Formula (e1), it is more preferable to be a group represented by any of Formula (f1) or Formula (a1), and it is particularly preferable to be a group represented by Formula (f1).

(f1)

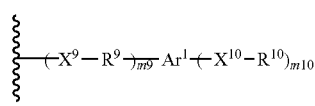

In Formula (f1), a wavy line portion represents a bonding position to the ring A, m9 represents an integer of 0 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms.

(a1)

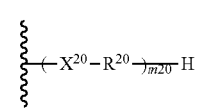

In Formula (a1), a wavy line portion represents a bonding position to the ring A, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

(b1)

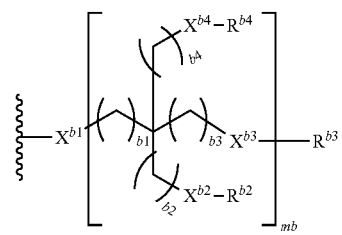

In Formula (b1), a wavy line portion represents a bonding position to the ring A, mb represents 1 or 2, b1 to b4 each independently represent an integer of 0 to 2, $X^{b1}$ to $X^{b4}$ each independently represent a single bond, —O—, —S—, —COO—, —OCONH—, or —CONH—, $R^{b2}$ and $R^{b4}$ each independently represent a hydrogen atom, a methyl group, or an aliphatic hydrocarbon group having 5 or more carbon atoms, and $R^{b3}$ represents an aliphatic hydrocarbon group having 5 or more carbon atoms.

(e1)

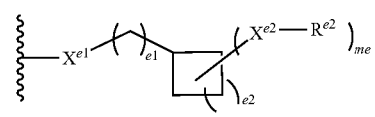

In Formula (e1), a wavy line portion represents a bonding position to the ring A, $X^{e1}$ represents a single bond, —O—, —S—, —NHCO—, or —CONH—, me represents an integer of 0 to 15, e1 represents an integer of 0 to 11, e2 represents an integer of 0 to 5, $X^{e2}$'s each independently represent a single bond, —O—, —S—, —COO—, —OCONH—, —NHCO—, or —CONH—, and $R^{e2}$'s each independently represent a hydrogen atom, a methyl group, or an organic group having an aliphatic hydrocarbon group having 5 or more carbon atoms.

m9 in Formula (f1) is preferably 0 or 1 and more preferably 1.

$X^9$ and $X^{10}$ in Formula (f1) are each independently preferably a single bond, —O—, —S—, —COO—, —OCONH—, or —CONH—, and more preferably a single bond.

$R^9$'s in Formula (f1) are each independently preferably an alkylene group having 1 to 10 carbon atoms, more preferably an alkylene group having 1 to 4 carbon atoms, and particularly preferably a methylene group.

$R^{10}$'s in Formula (f1) are each independently preferably a monovalent aliphatic hydrocarbon group having 5 to 60 carbon atoms, more preferably a monovalent aliphatic hydrocarbon group having 12 to 50 carbon atoms, still more preferably a monovalent aliphatic hydrocarbon group having 18 to 40 carbon atoms, and particularly preferably a monovalent aliphatic hydrocarbon group having 20 to 32 carbon atoms. In addition, $R^{10}$'s are each independently preferably a linear alkyl group or a branched alkyl group and more preferably a linear alkyl group.

m10 in Formula (f1) is preferably 2 or 3 and more preferably 2.

$Ar^1$ in Formula (f1) is preferably an (m10+1)-valent aromatic group, and more preferably a group obtained by removing (m10+1) pieces of hydrogen atoms from benzene.

In addition, from the viewpoint of solubility in a solvent, crystallization property, and yield, the group represented by Formula (f1) is preferably a group represented by Formula (f2).

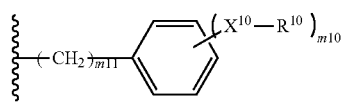

(f2)

In Formula (f2), a wavy line portion represents a bonding position to the ring A, m10 represents an integer of 1 to 3, m11 represents an integer of 0 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

m10, $X^{10}$, and $R^{10}$ in Formula (f2) have the same meanings as m10, $X^{10}$, and $R^{10}$ in Formula (f1), respectively, and the preferred aspects thereof are also the same.

m11 in Formula (f2) is preferably 0 or 1 and more preferably 1.

m20 in Formula (a1) is preferably 1 or 2 and more preferably 1.

$X^{20}$'s in Formula (a1) are each independently preferably —O—, —S—, —COO—, —OCONH—, or —CONH—, and more preferably —O—.

$R^{20}$ in Formula (a1) is preferably a divalent aliphatic hydrocarbon group having 5 or more carbon atoms, more preferably a divalent aliphatic hydrocarbon group having 5 to 60 carbon atoms, still more preferably a divalent aliphatic hydrocarbon group having 8 to 40 carbon atoms, and particularly preferably a divalent aliphatic hydrocarbon group having 12 to 32 carbon atoms. In addition, $R^{20}$ is preferably a linear alkylene group.

mb in Formula (b1) is preferably 1.

b1 to b4 in Formula (b1) are each independently preferably 1 or 2 and more preferably 1.

$X^{b1}$ to $X^{b4}$ in Formula (b1) are each independently preferably —O—, —S—, —COO—, —OCONH—, or —CONH—, and more preferably —O—.

$R^{b2}$ and $R^{b4}$ in Formula (b1) are each independently preferably a hydrogen atom, a methyl group, or an aliphatic hydrocarbon group having 5 to 60 carbon atoms, more preferably a hydrogen atom, a methyl group, or an alkyl group having 8 to 40 carbon atoms, and particularly preferably a hydrogen atom, a methyl group, or an alkyl group having 12 to 32 carbon atoms.

$R^{b3}$ in Formula (b1) is preferably a monovalent aliphatic hydrocarbon group having 5 to 60 carbon atoms, more preferably a monovalent aliphatic hydrocarbon group having 8 to 40 carbon atoms, and particularly preferably a monovalent aliphatic hydrocarbon group having 12 to 32 carbon atoms. In addition, $R^{b3}$ is preferably a linear alkyl group.

In addition, in the compound represented by Formula (1) according to the present disclosure, from the viewpoint of solubility in a solvent, preferred examples of the aliphatic hydrocarbon group in $R^A$ include an aliphatic hydrocarbon group having a branch, and more preferred examples thereof include groups shown below. A wavy line portion represents a bonding position to another structure, nt2 represents an integer of 3 or more, and nt3 represents an integer set such that the total number of carbon atoms in the following group is 14 to 300.

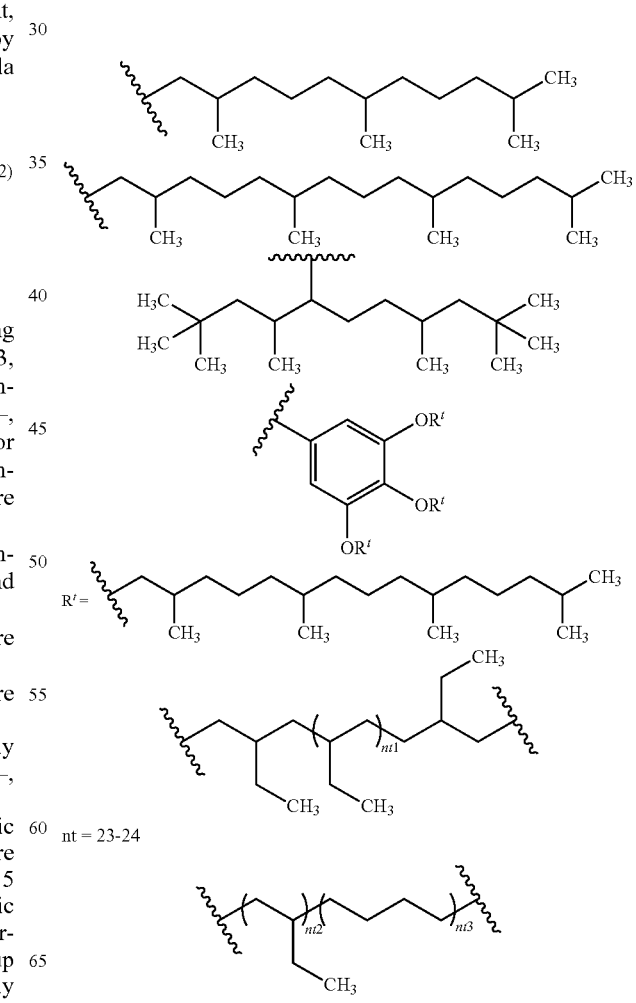

nt = 23-24

The substituent which may be included in the compound represented by Formula (1) on the ring A is not particularly limited, and examples thereof include an alkoxy group, an aryloxy group, a halogen atom, an alkyl group, a halogenated alkyl group, an aryl group, an acyl group, an acyloxy group, an alkoxycarbonyl group, an aryloxycarbonyl group, an alkylthio group, an arylthio group, $R^{st}$—CO—$NR^{st}$—, —CON($R^{st}$)$_2$, a dialkylamino group, an alkylarylamino group, a diarylamino group, and a group obtained by combining two or more of these groups. $R^{st}$ represents a hydrogen atom, an alkyl group, or an aryl group.

In addition, in a case where the compound represented by Formula (1) is a multimer, preferred examples of the substituent which may be included on the ring A include a group represented by Formula (M).

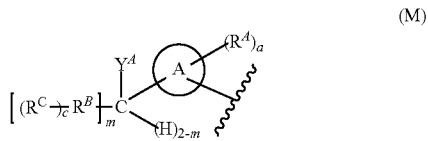

The ring A, $Y^A$, $X^0$, $R^A$, $R^B$, $R^C$, m, a, and c in Formula (M) have the same meanings as the ring A, $Y^A$, $X^0$, $R^A$, $R^B$, $R^C$, m, a, and c in Formula (1), respectively, and the preferred aspects thereof are also the same.

In addition, in a case of having the group represented by Formula (M) as a substituent, the compound represented by Formula (1) is preferably a compound represented by Formula (20) described later.

From the viewpoint of deprotection rate, crystallization property, solubility in a solvent, and yield, the ring A in Formula (1) is preferably a structure represented by any of Formula (10), Formula (20), or Formula (30), more preferably a structure represented by Formula (10) or Formula (20), and still more preferably a structure represented by Formula (10).

$R^{r10}$ represents a substituent or $R^A$, $R^{r11}$ to $R^{r14}$ each independently represent a hydrogen atom, a substituent, or $R^A$, and at least one of $R^{r10}$, $R^{r11}$, $R^{r12}$, $R^{r13}$, or $R^{r14}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r11}$ and $R^{r12}$, or $R^{r13}$ and $R^{r14}$ may be each independently linked to each other to form a ring or may be each independently linked to each other through a substituent to form a ring.

In Formula (20), any one of $R^{r20}$, $R^{r21}$, $R^{r22}$, or $R^{r23}$ is linked to a group which includes a carbon atom having $Y^A$ in Formula (1) (preferably, to a carbon atom linked to $Y^A$), $R^{r20}$ represents a substituent or $R^A$, $R^{r21}$ to $R^{r23}$ each independently represent a hydrogen atom, a substituent, or $R^A$, and at least one of $R^{r20}$, $R^{r21}$, $R^{r22}$, or $R^{r23}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r22}$ and $R^{r23}$ may be linked to each other to form a ring or may be linked to each other through a substituent to form a ring.

In Formula (30), any one of $R^{r31}$, $R^{r32}$, $R^{r33}$, or $R^{r34}$ is linked to a group which includes a carbon atom having $Y^A$ in Formula (1) (preferably, to a carbon atom linked to $Y^A$) $X^{30}$ represents an oxygen atom or a sulfur atom, $R^{r31}$ to $R^{r34}$ each independently represent a hydrogen atom, a substituent, or $R^A$, and at least one of $R^{r31}$, $R^{r32}$, $R^{r33}$, or $R^{r34}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r31}$ and $R^{r32}$, or $R^{r33}$ and $R^{r34}$ may be each independently linked to each other to form a ring or may be each independently linked to each other through a substituent to form a ring.

It is preferable that Formula (10) is a structure represented by Formula (11). It is preferable that Formula (20) is a structure represented by Formula (21). It is preferable that Formula (30) is a structure represented by Formula (31).

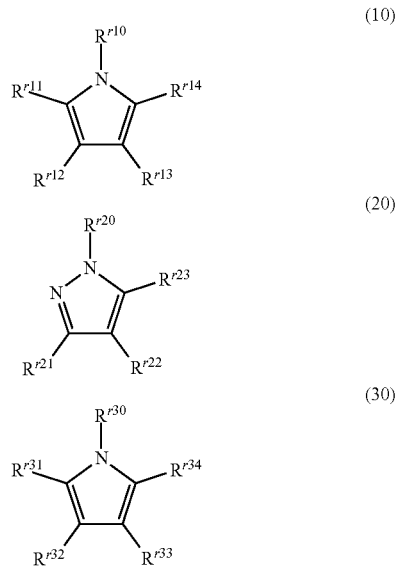

In Formula (10), any one of $R^{r10}$, $R^{r11}$, $R^{r12}$, $R^{r13}$, or $R^{r14}$ is linked to a group which includes a carbon atom having $Y^A$ in Formula (1) (preferably, to a carbon atom linked to $Y^A$), In Formula (11), any one of $R^{r15}$, $R^{r16}$, $R^{r17}$, or $R^{r18}$ is linked to the group which includes the carbon atom having $Y^A$ in Formula (1) (preferably, to the carbon atom linked to $Y^A$), $R^{r15}$ to $R^{r18}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r15}$ and $R^{r16}$, or $R^{r17}$ and $R^{r18}$ may be each independently linked to each other to form a ring or may be each independently linked to each other through a substituent to form a ring.

In Formula (11), from the viewpoint of crystallization property and yield, it is preferable that $R^{r15}$ and $R^{r16}$, or $R^{r17}$ and $R^{r18}$ are each independently linked to each other to form a ring. In a case where $R^{r15}$ and $R^{r16}$, or $R^{r17}$ and $R^{r18}$ are each independently linked to each other to form a ring, Formula (11) has an indole ring, and in a case where $R^{r15}$ and $R^{r16}$, and $R^{r17}$ and $R^{r18}$ are each independently linked to each other to form a ring, Formula (11) has a carbazole ring.

In Formula (21), any one of $R^{r24}$, $R^{r25}$, or $R^{r26}$ is linked to the group which includes the carbon atom having $Y^A$ in Formula (1) (preferably, to the carbon atom linked to $Y^A$), $R^{r24}$ to $R^{r26}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more (preferably, 16 or more), and $R^{r25}$ and $R^{r26}$ may be linked to each other to form a ring or may be linked to each other through a substituent to form a ring.

In Formula (21), in a case where $R^{r25}$ and $R^{r26}$ are linked to each other to form a ring, Formula (21) has an indazole ring.

In Formula (31), a wavy line portion represents a position linked to the group which includes the carbon atom having $Y^A$ in Formula (1) (preferably, to the carbon atom linked to $Y^A$), $X^{r31}$ represents an oxygen atom or a sulfur atom, $R^{r35}$ to $R^{r37}$ each independently represent a hydrogen atom, a substituent, or $R^A$, $R^A$'s each independently represent an aliphatic hydrocarbon group or an organic group having an aliphatic hydrocarbon group, the number of carbon atoms in at least one aliphatic hydrocarbon group in at least one $R^A$ is 14 or more (preferably, 16 or more), at least one of $R^{r35}$, $R^{r36}$, or $R^{r37}$ is $R^A$, and $R^{r36}$ and $R^{r37}$ may be linked to each other to form a ring or may be linked to each other through a substituent to form a ring.

In Formula (31), in a case where $R^{r36}$ and $R^{r37}$ are linked to each other to form a ring and $X^{r31}$ is a sulfur atom, Formula (31) has a benzothiophene ring; and in Formula (31), in a case where $R^{r36}$ and $R^{r37}$ are linked to each other to form a ring and $X^{r31}$ is an oxygen atom, Formula (31) has a benzofuran ring.

In Formula (31), from the viewpoint of yield, it is preferable that $R^{r36}$ and $R^{r37}$ are not linked to each other through a substituent to form a ring.

$R^A$'s in Formula (10), Formula (20), Formula (30), Formula (11), Formula (21), or Formula (31) have the same meanings as $R^A$ in Formula (1), respectively, and the preferred aspects thereof are also the same.

The substituents in Formula (10), Formula (20), Formula (30), Formula (11), Formula (21), or Formula (31) are each independently preferably a bonding site, an alkoxy group, an aryloxy group, a halogen atom, an alkyl group, a halogenated alkyl group, an aryl group, an acyl group, an acyloxy group, an alkoxycarbonyl group, an aryloxycarbonyl group, an alkylthio group, an arylthio group, $R^{st}$—CO—$NR^{st}$—, —CON($R^{st}$)$_2$, a dialkylamino group, an alkylarylamino group, a diarylamino group, or a group obtained by combining two or more of these groups, more preferably a bonding site, an alkoxy group, an aryloxy group, a halogen atom, an alkyl group, a halogenated alkyl group, or an aryl group, and still more preferably a bonding site, an alkoxy group, or an alkyl group.

From the viewpoint of solubility in a solvent, crystallization property, and yield, it is preferable that $R^A$ in Formula (10), Formula (20), Formula (30), Formula (11), Formula (21), or Formula (31) is a group represented by any of Formula (f1), Formula (a1), Formula (b1), or Formula (e1) described above, it is more preferable to be a group represented by any of Formula (f1) or Formula (a1) described above, it is still more preferable to be a group represented by Formula (f1) described above, and it is particularly preferable to be a group represented by Formula (f2).

As the ring A in Formula (1), from the viewpoint of solubility in a solvent, crystallization property, and yield, the structure represented by Formula (11) or Formula (31) is preferable, and the structure represented by Formula (11) is more preferable.

From the viewpoint of solubility in a solvent, crystallization property, and yield, it is preferable that the structure represented by Formula (11) is a carbazole ring or an indole ring, and it is more preferable that the compound represented by Formula (10) is a compound represented by any of Formula (111), Formula (112), Formula (113), or Formula (114).

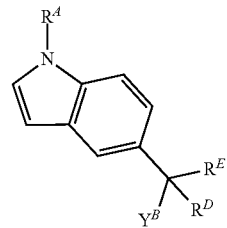

(111)

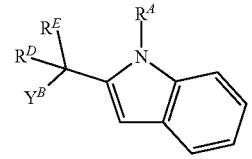

(112)

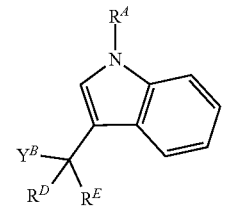

(113)

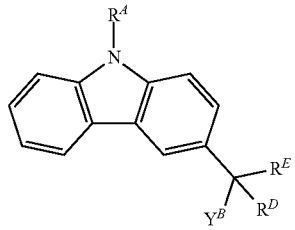

(114)

In Formulae (111) to (114), $R^A$ represents an aliphatic hydrocarbon group having 12 or more carbon atoms or an organic group having an aliphatic hydrocarbon group having 12 or more carbon atoms, $Y^B$ represents —OH, —NHR, —SH, or —$X^O$, where R represents a hydrogen atom, an alkyl group, an aromatic group-substituted alkyl group, a heteroaromatic group-substituted alkyl group, or an Fmoc group, and $X^O$ represents Cl, Br, or I, and $R^D$ represents a hydrogen atom, an alkyl group, an aryl group, or a heteroaryl group, and $R^E$ represents a hydrogen atom, an alkyl group, an aryl group, or a heteroaryl group.

$Y^B$, $R^A$, R, and $X^O$ in Formulae (111) to (114) have the same meanings as $Y^A$, $R^A$, R, and $X^O$ in Formula (1), and the preferred aspects thereof are also the same.

From the viewpoint of deprotection rate, crystallization property, solubility in a solvent, and yield, $R^D$ in Formulae (111) to (114) is preferably a hydrogen atom, an aryl group, or a heteroaryl group, and more preferably a hydrogen atom or an aryl group.

In particular, in a case where $R^E$ is a hydrogen atom and $Y^B$ is —OH, $R^D$ is preferably a hydrogen atom, a phenyl group, or a phenyl group substituted with a halogen atom, and more preferably a hydrogen atom. In a case where $R^E$ is a hydrogen atom and $Y^B$ is —NHR, $R^D$ is preferably a hydrogen atom, a phenyl group, an alkoxyphenyl group, a dialkoxyphenyl group, or a trialkoxyphenyl group, and more preferably a hydrogen atom, a phenyl group, or a dialkoxyphenyl group.

In addition, the number of carbon atoms in $R^D$ is preferably 1 to 30, more preferably 5 to 30, and particularly preferably 6 to 24.

The molecular weight of the compound represented by Formula (1) is not particularly limited, but from the viewpoint of deprotection rate, crystallization property, solubility in a solvent, and yield, it is preferably 340 to 3,000, more preferably 400 to 2,000, still more preferably 500 to 1,500, and particularly preferably 800 to 1,300. In addition, in a case where the molecular weight is 3,000 or less, the proportion of Formula (1) in the target product is appropriate and the proportion of a compound obtained by deprotecting Formula (1) is not reduced, so that productivity is excellent.

Preferred specific examples of the compound represented by Formula (1) include compounds shown below, but the compound represented by Formula (1) is not limited thereto.

$R^g$ represents an aliphatic hydrocarbon group having 12 or more carbon atoms, and an aliphatic hydrocarbon group having 12 to 100 carbon atoms is preferable, an aliphatic hydrocarbon group having 18 to 40 carbon atoms is more preferable, and an aliphatic hydrocarbon group having 20 to 32 carbon atoms is particularly preferable. In addition, the above-described aliphatic hydrocarbon group is preferably a linear alkyl group, a branched alkyl group, or a cyclic alkyl group, and more preferably a linear alkyl group.

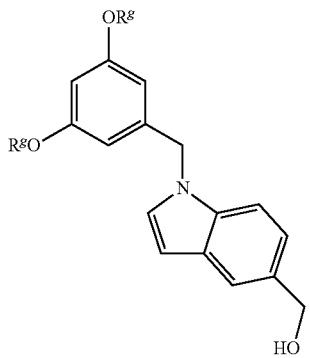

-continued

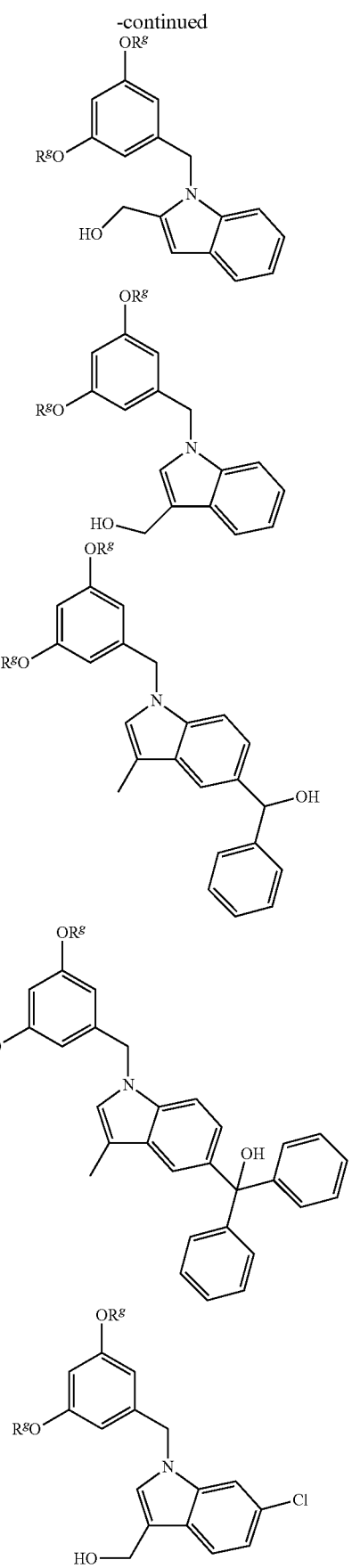

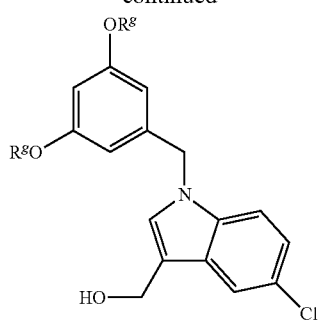
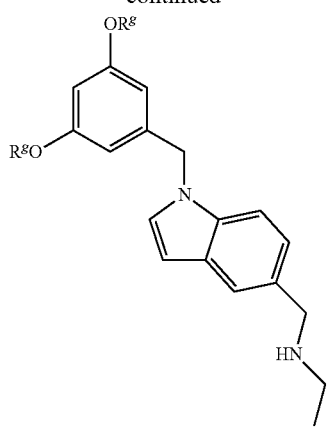

33
-continued
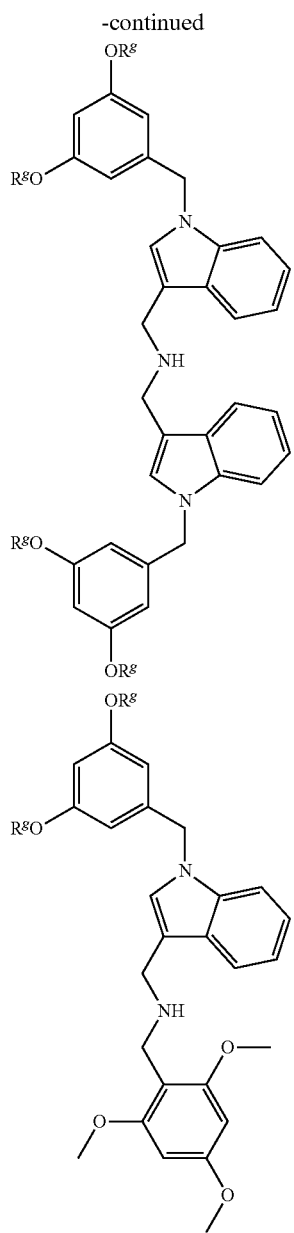
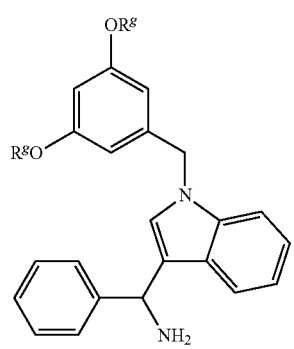
34
-continued
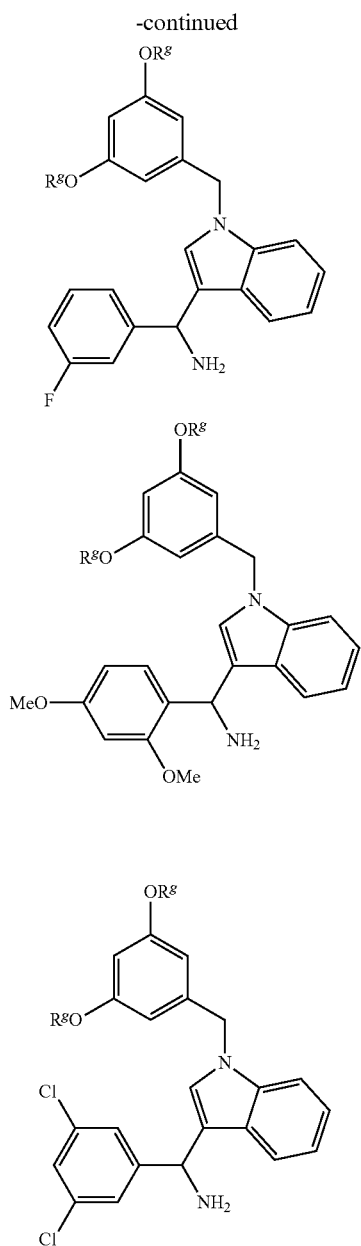
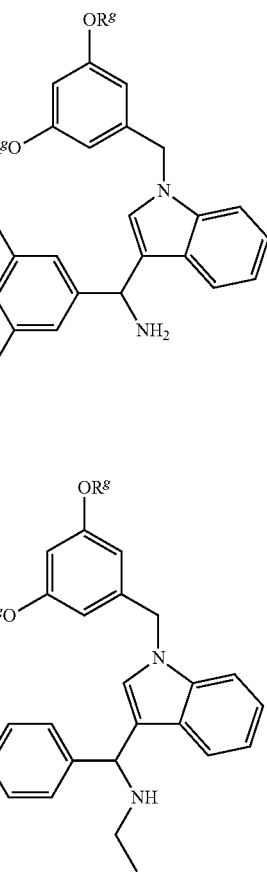

35
-continued
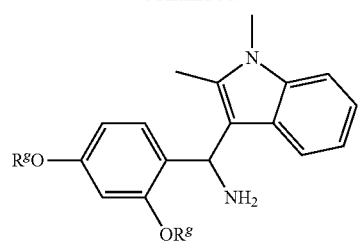
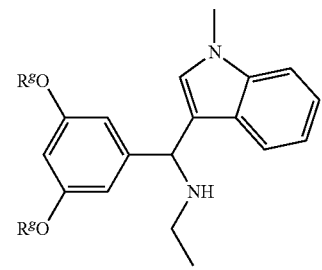
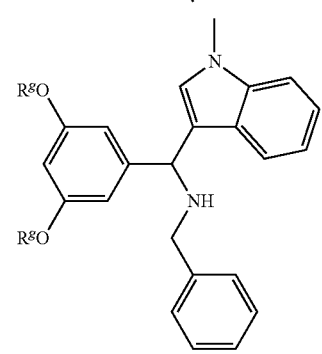
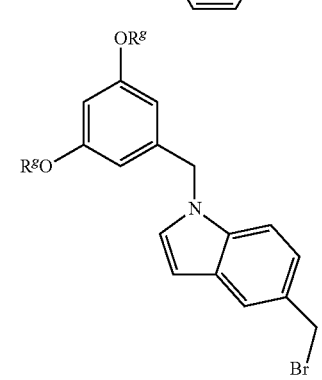
36
-continued

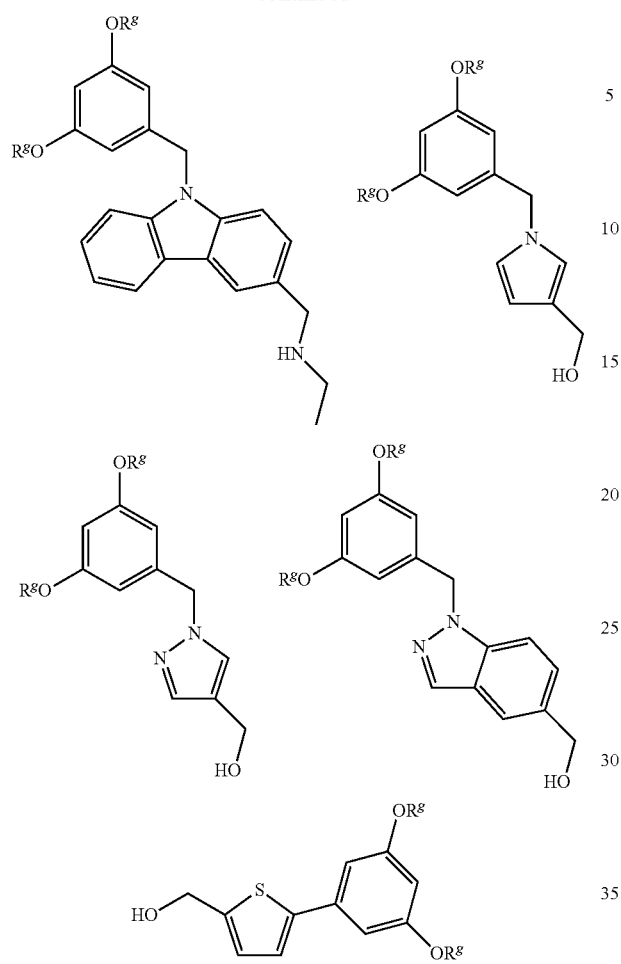

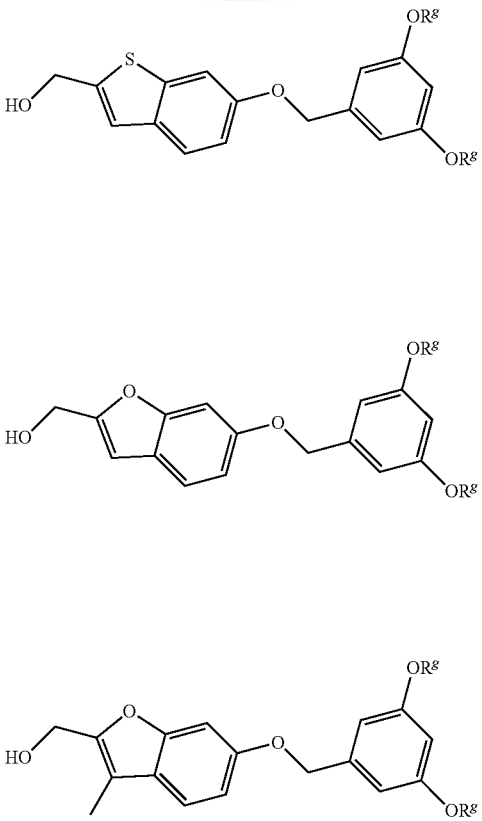

<<Method for Producing Aromatic Heterocyclic Compound Represented by Formula (1)>>

A method for producing the aromatic heterocyclic compound represented by Formula (1) according to the present disclosure is not particularly limited, and can be produced by referring to a known method.

Unless otherwise specified, a raw material compound used for producing the aromatic heterocyclic compound represented by Formula (1) may be a commercially available compound, or may be produced by a known method or a method according to the known method.

In addition, the produced aromatic heterocyclic compound represented by Formula (1) may be purified by a known purification method as necessary. For example, a method of isolating and purifying by recrystallization, column chromatography, or the like, a method of purifying by reprecipitation with a unit for changing the solution temperature, a unit for changing the solution composition, or the like, and the like can be performed.

The method for synthesizing the aromatic heterocyclic compound represented by Formula (1) according to the present disclosure is not particularly limited, but the aromatic heterocyclic compound represented by Formula (1) can be synthesized according to, for example, Scheme 1 or Scheme 2 below. In addition, it is also possible to synthesize by referring to the synthesis method described in WO2010/113939A.

Scheme 1

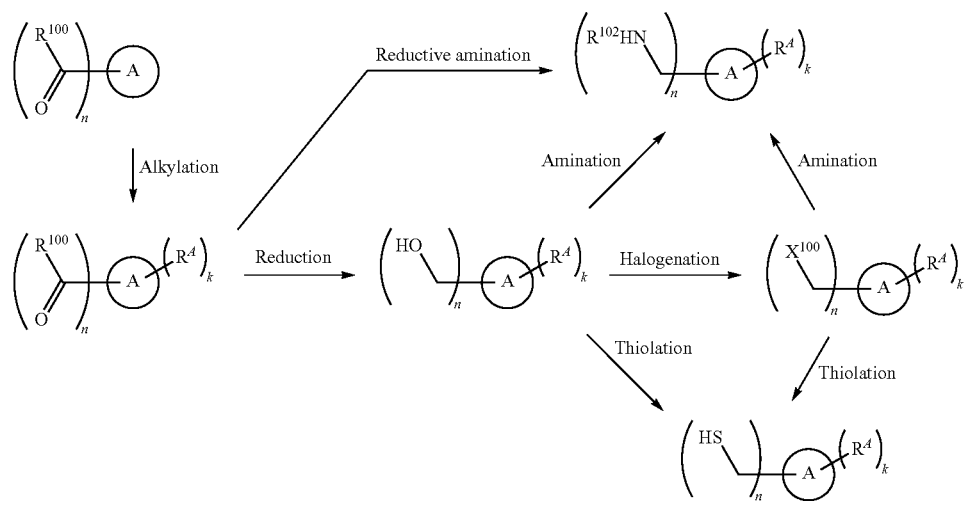

Scheme 2

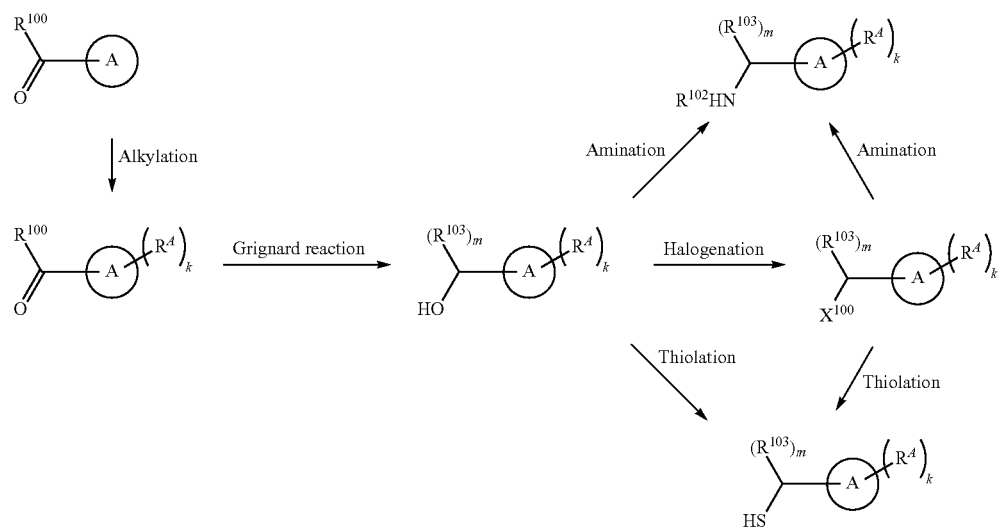

$R^{100}$ represents a hydrogen atom or $OR^{101}$, where $R^{101}$ represents an alkyl group. $X^{100}$ represents Cl, Br, or I. $R^{102}$ represents a hydrogen atom, an alkyl group, or an Fmoc group. $R^{103}$ represents an alkyl group, an aromatic hydrocarbon group which may have a substituent, or an aromatic heterocyclic group which may have a substituent. n represents 1 or 2, k represents an integer of 1 to 5, and m represents 1 or 2.

<<Method for Producing Peptide Compound>>

In the method for producing a peptide compound according to the embodiment of the present disclosure, it is preferable that the step of using the aromatic heterocyclic compound represented by Formula (1) is a C-terminal protecting step of protecting a carboxy group or an amide group of an amino acid compound or a peptide compound with the aromatic heterocyclic compound represented by Formula (1).

In addition, from the viewpoint of ease of synthesizing the peptide compound and yield, it is more preferable that the method for producing a peptide compound according to the embodiment of the present disclosure further includes, in addition to the above-described C-terminal protecting step of protecting a carboxy group or an amide group of an amino acid compound or a peptide compound with the aromatic heterocyclic compound represented by Formula (1), an N-terminal deprotecting step of deprotecting an N-terminal end of an N-terminal and C-terminal protected amino acid compound or an N-terminal and C-terminal protected peptide compound, which is obtained in the C-terminal protecting step, and a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound; it is still more preferable that the method for producing a peptide compound according to the embodiment of the present disclosure further includes, in addition to the above steps, a precipitating step of precipitating an N-terminal and C-terminal protected peptide compound obtained in the peptide chain extending step; and it is particularly preferable that the method for producing a peptide compound according to the embodiment of the present disclosure further includes, one or more times in the following order after the precipitating step, a step of deprotecting an N-terminal end of the obtained N-terminal and C-terminal protected peptide compound, a step of condensing the N-terminal end of the obtained C-terminal protected peptide compound with an N-terminal protected amino acid compound or an N-terminal protected peptide compound, and a step of precipitating the obtained N-terminal and C-terminal protected peptide compound.

In addition, it is preferable that the method for producing a peptide compound according to the embodiment of the present disclosure further includes a C-terminal deprotecting step of deprotecting a C-terminal protective group.

Furthermore, it is preferable that the method for producing a peptide compound according to the embodiment of the present disclosure further includes, before the above-described C-terminal protecting step, a dissolving step of dissolving the aromatic heterocyclic compound represented by Formula (1) in a solvent.

Hereinafter, each step will be described in detail.

<<Dissolving Step>>

It is preferable that the method for producing a peptide compound according to the embodiment of the present disclosure includes, before the above-described C-terminal protecting step, a dissolving step of dissolving the aromatic heterocyclic compound represented by Formula (1) in a solvent.

As the solvent, a general organic solvent can be used for the reaction, but since excellent reactivity can be expected as solubility in the above-described solvent is higher, it is preferable to select a solvent having a high solubility of the aromatic heterocyclic compound represented by Formula (1). Specific examples thereof include halogenated hydrocarbons such as chloroform and dichloromethane; and nonpolar organic solvents such as 1,4-dioxane, tetrahydrofuran, and cyclopentyl methyl ether. Two or more of these solvents may be mixed and used in an appropriate ratio. In addition, as long as the aromatic heterocyclic compound represented by Formula (1) can be dissolved, in the above-described halogenated hydrocarbons or nonpolar organic solvents, aromatic hydrocarbons such as benzene, toluene, and xylene; nitriles such as acetonitrile and propionitrile; ketones such as acetone and 2-butanone; amides such as N,N-dimethylformamide and N-methylpyrrolidone; and sulfoxides such as dimethyl sulfoxide may be mixed and used in an appropriate ratio.

In addition, a solvent described in Organic Process Research & Development, 2017, 21, 3, 365 to 369 may be used.

<C-Terminal Protecting Step>

The method for producing a peptide compound according to the embodiment of the present disclosure includes a C-terminal protecting step of protecting a carboxy group or an amide group of an amino acid compound or a peptide compound with the aromatic heterocyclic compound represented by Formula (1).

The amino acid compound or peptide compound used in the above-described C-terminal protecting step is not particularly limited, and a known compound can be used. However, an N-terminal protected amino acid compound or an N-terminal protected peptide compound is preferable, and an Fmoc-protected amino acid compound or an Fmoc-protected peptide compound is more preferable.

In addition, it is preferable that a hydroxy group, an amino group, a carbonyl group, an amide group, an imidazole group, an indole group, a guanidyl group, a mercapto group, or the like, which is a moiety other than the C-terminal end in the amino acid compound or peptide compound used in the above-described C-terminal protecting step, is protected by a known protective group such as a protective group described later.

The amount of the amino acid compound or peptide compound, which is used as a reaction substrate, to be used is preferably 1 molar equivalent to 10 molar equivalent, more preferably 1 molar equivalent to 5 molar equivalent, still more preferably 1 molar equivalent to 2 molar equivalent, and particularly preferably 1 molar equivalent to 1.5 molar equivalent with respect to 1 molar equivalent of the aromatic heterocyclic compound represented by Formula (1).

In a case where an aromatic heterocyclic compound represented by Formula (1), in which $Y^A$ in Formula (1) is —OH or —SH, is used, it is preferable to add a condensing agent in the presence of a condensation additive (condensation activating agent) in a solvent which does not affect the reaction, or to react in an acid catalyst.

In a case where an aromatic heterocyclic compound represented by Formula (1), in which $Y^A$ in Formula (1) is —NHR, is used, it is preferable to add a condensing agent in the presence of a condensation additive (condensation activating agent), or to react with a condensing agent and a base.

The amount of the condensation additive to be used is preferably 0.05 molar equivalent to 1.5 molar equivalent with respect to 1 molar equivalent of the aromatic heterocyclic compound represented by Formula (1).

As the condensing agent, a condensing agent generally used in peptide synthesis can be used without limitation in the present disclosure. Examples thereof include 4-(4,6-dimethoxy-1,3,5-triazin-2-yl)-4-methylmorpholinium chloride (DMTMM), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), O-(6-chlorobenzotriazol-1-yl)-1,1,3,3-tetramethyluronium hexafluorophosphate (HBTU(6-Cl)), O-(benzotriazol-1-yl)-1,1,3,3-tetramethyluronium tetrafluoroborate (TBTU), O-(6-chlorobenzotriazol-1-yl)-1,1,3,3-tetramethyluronium tetrafluoroborate (TCTU), (1-cyano-2-ethoxy-2-oxoethylidenaminooxy)dimethylamino-morpholino-carbenium hexafluorophosphate (COMU), dicyclohexylcarbodiimide (DCC), diisopropylcarbodiimide (DIC), 1-ethyl-3-(3-dimethylaminopropyl) carbodiimide (EDC), a hydrochloride salt (EDC/HCl) of 1-ethyl-3-(3-dimethylaminopropyl) carbodiimide, and (benzotriazol-1-yloxy)tripyrrolidinophosphonium hexafluorophosphate (PyBoP), but the condensing agent is not limited thereto.

Among these, DIC, EDC, EDC/HCl, DMTMM, HBTU, HATU, or COMU is preferable.

The amount of the condensing agent to be used is preferably 1 molar equivalent to 10 molar equivalent and more preferably 1 molar equivalent to 5 molar equivalent with respect to 1 molar equivalent of the aromatic heterocyclic compound represented by Formula (1).

As the acid catalyst used in the condensation reaction, an acid catalyst generally used in peptide synthesis can be used without limitation, and examples thereof include methanesulfonic acid, trifluoromethanesulfonic acid, and p-toluenesulfonic acid.

Among these, methanesulfonic acid or p-toluenesulfonic acid is preferable.

The amount of the acid catalyst to be used is preferably more than 0 molar equivalent and 4.0 molar equivalent or less, more preferably 0.05 molar equivalent to 1.5 molar equivalent, and still more preferably 0.1 molar equivalent to 0.3 molar equivalent with respect to 1 molar equivalent of the aromatic heterocyclic compound represented by Formula (1).

In the above-described C-terminal protecting step, it is preferable to add a condensation activating agent in order to promote the reaction and suppress side reactions such as racemization.

The condensation activating agent in the present disclosure is a reagent which, in a case of coexisting with the condensing agent, leads an amino acid to a corresponding active ester, symmetric acid anhydride, or the like to facilitate the formation of a peptide bond (amide bond).

As the condensation activating agent, a condensation activating agent generally used in peptide synthesis can be used without limitation, and examples thereof include 4-dimethylaminopyridine, N-methylimidazole, boronic acid derivative, 1-hydroxybenzotriazole (HOBt), ethyl 1-hydroxytriazole-4-carboxylate (HOCt), 1-hydroxy-7-azabenzotriazole (HOAt), 3-hydroxy-1,2,3-benzotriazin-4(3H)-one (HOOBt), N-hydroxysuccinimide (HOSu), N-hydroxyphthalimide (HOPht), N-hydroxy-5-norbornene-2,3-dicarboxyimide (HONb), pentafluorophenol, and ethyl(hydroxyimino)cyanoacetylate (Oxyma). Among these, 4-dimethylaminopyridine, HOBt, HOCt, HOAt, HOOBt, HOSu, HONb, or Oxyma is preferable.

The amount of the activating agent to be used is preferably more than 0 molar equivalent and 4.0 molar equivalent or less and more preferably 0.1 molar equivalent to 1.5 molar equivalent with respect to the amino acid compound or peptide compound.

As the base, a base generally used in peptide synthesis can be used without limitation, and examples thereof include a tertiary amine such as diisopropylethylamine.

As the solvent, the solvent exemplified in the above-described dissolving step can be preferably used.

The reaction temperature is not particularly limited, but is preferably −10° C. to 80° C. and more preferably 0° C. to 40° C. The reaction time is not particularly limited, but is preferably 1 hour to 30 hours.

To confirm the progress of the reaction, a method same as that of a general liquid phase organic synthesis reaction can be applied. That is, the reaction can be traced using thin-layer silica gel chromatography, high performance liquid chromatography, NMR, or the like.

In addition, the N-terminal and C-terminal protected amino acid compound or N-terminal and C-terminal protected peptide compound obtained by the above-described C-terminal protecting step may be purified.

For example, in order to isolate the product obtained after dissolving the obtained N-terminal and C-terminal protected amino acid compound or N-terminal and C-terminal protected peptide compound in a solvent and performing a desired organic synthesis reaction, it is preferable to perform a method of changing the solvent to a solvent in which the N-terminal and C-terminal protected amino acid compound or N-terminal and C-terminal protected peptide compound is dissolved (for example, change of solvent composition or change of solvent type) and reprecipitating the resultant.

Specifically, for example, the reaction is performed under conditions such that the N-terminal and C-terminal protected amino acid compound or N-terminal and C-terminal protected peptide compound is dissolved, and after the reaction, the solvent is distilled off and then replaced, or after the reaction, by adding a polar solvent to the reaction system without distilling off the solvent, aggregates are precipitated and impurities are eliminated. As the solvent for replacement, polar organic solvents such as methanol, acetonitrile, and water are used alone or in combination. That is, the reaction is performed under conditions such that the N-terminal and C-terminal protected amino acid compound or N-terminal and C-terminal protected peptide compound is dissolved, and in the solvent replacement after the reaction, for example, a halogenated solvent, THF, or the like is used for dissolution, and a polar organic solvent such as methanol, acetonitrile, and water is used for precipitation.

<N-Terminal Deprotecting Step>

It is preferable that the method for producing a peptide compound according to the embodiment of the present disclosure includes an N-terminal deprotecting step of deprotecting an N-terminal end of the N-terminal and C-terminal protected amino acid compound or N-terminal and C-terminal protected peptide compound, which is obtained in the C-terminal protecting step.

As the N-terminal protective group, a protective group for an amino group described later, which is generally used in technical fields such as peptide chemistry, can be used, but in the present disclosure, a tert-butoxycarbonyl group (hereinafter, also referred to as a Boc group), a benzyloxycarbonyl group (hereinafter, also referred to as a Cbz group or a Z group), or a 9-fluorenylmethoxycarbonyl group (hereinafter, also referred to as an Fmoc group) is suitably used.

The deprotection condition is appropriately selected depending on the type of the temporary protective group, but a group which can be deprotected under conditions different from the removal of the protective group derived from the aromatic heterocyclic compound represented by Formula (1) is preferable. For example, in a case of the Fmoc group, the deprotection is performed by treating with a base, and in a case of the Boc group, the deprotection is performed by treating with an acid. The reaction is performed in a solvent which does not affect the reaction.

Examples of the base include secondary amines such as dimethylamine and diethylamine, and non-nucleophilic organic bases such as 1,8-diazabicyclo[5.4.0]-7-undecene (DBU), 1,4-diazabicyclo[2.2.2]octane (DABCO), and 1,5-diazabicyclo[4.3.0]-5-nonene (DBN).

As the solvent, the solvent exemplified in the above-described dissolving step can be preferably used.

<Peptide Chain Extending Step>

It is preferable that the method for producing a peptide compound according to the embodiment of the present disclosure includes a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound.

The above-described peptide chain extending step is preferably performed under peptide synthesis conditions generally used in the field of peptide chemistry, in which the above-described condensing agent, condensation additive, and the like are used.

The N-terminal protected amino acid compound or N-terminal protected peptide compound is not particularly limited, and a desired compound can be used. However, an Fmoc-protected amino acid compound or an Fmoc-protected peptide compound can be suitably used.

In addition, it is preferable that a hydroxy group, an amino group, a carbonyl group, an amide group, an imidazole group, an indole group, a guanidyl group, a mercapto group, or the like, which is a moiety other than the C-terminal end in the N-terminal protected amino acid compound or N-terminal protected peptide compound, is protected by a known protective group such as a protective group described later.

<<Precipitating Step>>

It is preferable that the method for producing a peptide compound according to the embodiment of the present disclosure further includes a precipitating step of precipitating the N-terminal and C-terminal protected peptide compound obtained in the peptide chain extending step.

The above-described precipitating step can be performed in the same manner as the precipitation method in the purification which may be performed after the above-described C-terminal protecting step.

<<Chain Extension>>

It is preferable that the method for producing a peptide compound according to the embodiment of the present disclosure further includes, one or more times in the following order after the precipitating step, a step of deprotecting an N-terminal end of the obtained N-terminal and C-terminal protected peptide compound, a step of condensing the N-terminal end of the obtained C-terminal protected peptide compound with an N-terminal protected amino acid compound or an N-terminal protected peptide compound, and a step of precipitating the obtained N-terminal and C-terminal protected peptide compound.

By repeating the above-described three steps, the chain extension of the obtained peptide compound can be easily performed.

Each step in the above-described three steps can be performed in the same manner as each corresponding step described above.

<C-Terminal Deprotecting Step>

It is preferable that the method for producing a peptide compound according to the embodiment of the present disclosure further includes a C-terminal deprotecting step of deprotecting a C-terminal protective group.

In the above-described C-terminal deprotecting step, by removing the C-terminal protective group formed by the aromatic heterocyclic compound represented by Formula (1) in the C-terminal protected peptide compound having a desired number of amino acid residues, a peptide compound, which is the final target product, can be obtained.

Preferred examples of a method of removing the C-terminal protective group include a deprotecting method using an acidic compound.

Examples thereof include a method using an acid catalyst and a hydrogenating method using a metal catalyst. Examples of the acid catalyst include trifluoroacetic acid (TFA), hydrochloric acid, trifluoroethanol (TFE), hexafluoroisopropanol (HFIP), and acetic acid. TFA is preferable for peptides which do not decompose with strong acids, and TFE, HFIP, or acetic acid is preferable for peptides which decompose with strong acids. The concentration of the acid can be appropriately selected depending on the protective group and the deprotection condition, and is preferably 0.01% by mass to 100% by mass and more preferably 1% by mass to 100% by mass with respect to the total mass of the solvent used.

In addition, the concentration of TFA is preferably 70% by mass or less, more preferably 50% by mass or less, still more preferably 30% by mass or less, even more preferably 10% by mass or less, and particularly preferably 1% by mass or less. In the present disclosure, the C-terminal protective group can be deprotected even under weak acid conditions, and a side reaction of the obtained peptide can be suppressed.

The deprotection time is preferably 5 hours or less, more preferably 3 hours or less, and still more preferably 1 hour or less.

The peptide compound, which is the final target product obtained by the method for producing a peptide compound according to the embodiment of the present disclosure, can be isolated and purified according to a method commonly used in peptide chemistry. For example, the peptide compound, which is the final target product, can be isolated and purified by extraction and washing the reaction mixture, crystallization, chromatography, and the like.

The type of peptide produced by the method for producing a peptide compound according to the embodiment of the present disclosure is not particularly limited, but it is preferable that the number of amino acid residues of the peptide compound is, for example, approximately several tens or less. Same as existing or unknown synthetic or native peptides, the peptide obtained by the method for producing a peptide compound according to the embodiment of the present disclosure can be used in various fields such as pharmaceuticals, foods, cosmetics, electronic materials, biosensors, and the like.

In the method for producing a peptide compound according to the embodiment of the present disclosure, the precipitating step can be appropriately omitted as long as it does not affect the reaction in the next step.

In a case where the amino acid compound or peptide compound used in the method for producing a peptide compound according to the embodiment of the present disclosure has a hydroxy group, an amino group, a carboxy group, a carbonyl group, a guanidyl group, a mercapto group, or the like, a protective group generally used in peptide chemistry or the like may be introduced into these groups, and the target compound can be obtained by removing the protective group as necessary after the reaction.

Examples of a protective group of the hydroxy group include an alkyl group having 1 to 6 carbon atoms (for example, methyl, ethyl, propyl, isopropyl, butyl, and tert-butyl), a phenyl group, a trityl group, an aralkyl group having 7 to 10 carbon atoms (for example, benzyl), a formyl group, an acyl group having 1 to 6 carbon atoms (for example, acetyl and propionyl), a benzoyl group, an aralkyl-carbonyl group having 7 to 10 carbon atoms (for example, benzylcarbonyl), a 2-tetrahydropyranyl group, a 2-tetrahydrofuranyl group, a silyl group (for example, trimethylsilyl, triethylsilyl, dimethylphenylsilyl, tert-butyldimethylsilyl, and tert-butyldiethylsilyl), and an alkenyl group having 2 to 6 carbon atoms (for example, 1-propenyl). These groups may be substituted with one to three substituents selected from the group consisting of a halogen atom (for example, fluorine atom, chlorine atom, bromine atom, and iodine atom), an alkyl group having 1 to 6 carbon atoms (for example, methyl, ethyl, and propyl), an alkoxy group having 1 to 6 carbon atoms (for example, methoxy, ethoxy, and propoxy), and a nitro group.

Examples of a protective group of the amino group include a formyl group, an acyl group having 1 to 6 carbon atoms (for example, acetyl and propionyl), an alkoxycarbonyl group having 1 to 6 carbon atoms (for example, methoxycarbonyl, ethoxycarbonyl, and Boc group), a benzoyl group, an aralkyl-carbonyl group having 7 to 10 carbon atoms (for example, benzylcarbonyl), an aralkyloxycarbonyl group having 7 to 14 carbon atoms (for example, benzyloxycarbonyl and Fmoc group), a trityl group, a monomethoxytrityl group, a 1-(4,4-Dimethyl-2,6-dioxocyclohex-1-ylidene)-3-methylbutyl group, a phtaloyl group, an N,N-dimethylaminomethylene group, a silyl group (for example, trimethylsilyl, triethylsilyl, dimethylphenylsilyl, tert-butyldimethylsilyl, and tert-butyldiethylsilyl), and an alkenyl group having 2 to 6 carbon atoms (for example, 1-propenyl). These groups may be substituted with one to three substituents selected from the group consisting of a halogen atom (for example, fluorine atom, chlorine atom, bromine atom, and iodine atom), an alkoxy group having 1 to 6 carbon atoms (for example, methoxy, ethoxy, and propoxy), and a nitro group.

Examples of a protective group of the carboxy group include an alkyl group having 1 to 6 carbon atoms (for example, methyl, ethyl, propyl, isopropyl, butyl, and tert-butyl), an aralkyl group having 7 to 10 carbon atoms (for example, benzyl), a phenyl group, a trityl group, a silyl group (for example, trimethylsilyl, triethylsilyl, dimethylphenylsilyl, tert-butyldimethylsilyl, tert-butyldiethylsilyl, and tert-butyldiphenylsilyl), and an alkenyl group having 2 to 6 carbon atoms (for example, 1-allyl). These groups may be substituted with one to three substituents selected from the group consisting of a halogen atom (for example, fluorine atom, chlorine atom, bromine atom, and iodine atom), an alkoxy group having 1 to 6 carbon atoms (for example, methoxy, ethoxy, and propoxy), and a nitro group.

Examples of a protective group of the carbonyl group include cyclic acetals (for example, 1,3-dioxane) and acyclic acetals (for example, di(alkyl having 1 to 6 carbon atoms) acetal).

Examples of a protective group of the guanidyl group include a 2,2,4,6,7-pentamethyldihydrobenzofuran-5-sulfonyl group, a 2,3,4,5,6-pentamethylbenzenesulfonyl group, a tosyl group, and a nitro group.

Examples of a protective group of the mercapto group (sulfhydryl group) include a trityl group, a 4-methylbenzyl group, an acetylaminomethyl group, a t-butyl group, and a t-butylthio group.

In addition, the method of removing these protective groups may be performed according to a known method described in, for example, Protective Groups in Organic Synthesis, John Wiley and Sons (1980). For example, a method using acid, base, ultraviolet light, hydrazine, phenylhydrazine, sodium N-methyldithiocarbamate, tetrabutylammonium fluoride, palladium acetate, trialkylsilyl halide (for example, trimethylsilyl iodide and trimethylsilyl bromide), or the like, a reduction method, and the like are used.

In the method for producing a peptide compound according to the embodiment of the present disclosure, the aromatic heterocyclic compound represented by Formula (1) can be used not only for formation of a protective group, but also for denaturation of a peptide compound, adjustment of solubility in water or an organic solvent, improvement of crystallinity, multimerization, and the like.

Among these, the aromatic heterocyclic compound represented by Formula (1) is preferably used for formation of a protective group, and more preferably used for forming a C-terminal protective group in an amino acid compound or a peptide compound.

(Protective Group-Forming Reagent)

The protective group-forming reagent according to the embodiment of the present disclosure includes the above-described aromatic heterocyclic compound represented by Formula (1).

The protective group-forming reagent according to the embodiment of the present disclosure is preferably a protective group-forming reagent of a carboxy group or an amide group, and more preferably a C-terminal protective group-forming reagent of an amino acid compound or a peptide compound.

A preferred aspect of the aromatic heterocyclic compound represented by Formula (1) in the protective group-forming reagent according to the embodiment of the present disclosure is the same as the above-described preferred aspect of the aromatic heterocyclic compound represented by Formula (1) used in the method for producing a peptide compound.

The protective group-forming reagent according to the embodiment of the present disclosure may be a solid reagent or a liquid reagent.

The content of the aromatic heterocyclic compound represented by Formula (1) in the protective group-forming reagent according to the embodiment of the present disclosure is not particularly limited, but is preferably 0.1% by mass to 100% by mass, more preferably 1% by mass to 100% by mass, and still more preferably 3% by mass to 100% by mass with respect to the total mass of the protective group-forming reagent.

The protective group-forming reagent according to the embodiment of the present disclosure may include a component other than the aromatic heterocyclic compound represented by Formula (1).

As the other components, a known component can be included. Examples thereof include water, an organic solvent, an antioxidant, and a pH adjuster.

(Aromatic Heterocyclic Compound Represented by Formula (1a))

The compound according to the embodiment of the present disclosure is an aromatic heterocyclic compound represented by Formula (1a).

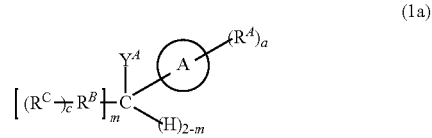

In Formula (1a), a ring A represents an aromatic heterocyclic ring, $Y^A$ represents —OH, —NHR, SH, or —$X^0$, where R represents a hydrogen atom, an alkyl group, an aromatic group-substituted alkyl group, a heteroaromatic group-substituted alkyl group, or an Fmoc group, and $X^0$ represents Cl, Br, or I, $R^A$'s each independently represent an aliphatic hydrocarbon group or an organic group having an aliphatic hydrocarbon group, where the number of carbon atoms in at least one aliphatic hydrocarbon group included in at least one of $R^A$, $R^B$, or $R^C$ is 12 or more, and the ring A may further have a substituent in addition to $R^A$, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, and a total number of carbon atoms in all aliphatic hydrocarbon groups included in $R^A$, $R^B$, and $R^C$ is 40 or more.

The aromatic heterocyclic compound represented by Formula (1a) according to the present disclosure and an aromatic heterocyclic compound represented by any of Formula (10a), Formula (20a), or Formula (30a) according to the present disclosure described later are novel compounds and can be suitably used for producing a peptide compound. Among these, the aromatic heterocyclic compound represented by Formula (1a) according to the present disclosure and an aromatic heterocyclic compound represented by any of Formula (10a), Formula (20a), or Formula (30a) described later can be suitably used as a protective group-forming reagent, more suitably used as a protective group-forming reagent of a carboxy group or an amide group, and particularly suitably used as a C-terminal protective group-forming reagent of an amino acid compound or a peptide compound.

The aromatic heterocyclic compound represented by Formula (1a) in the compound according to the embodiment of the present disclosure is the same as the aromatic heterocyclic compound represented by Formula (1) in the above-described method for producing a peptide compound according to the embodiment of the present disclosure, except that the total number of carbon atoms in all aliphatic hydrocarbon groups included in $R^A$, $R^B$, and $R^C$ is 40 or more. In addition, the same applies to preferred aspects other than the preferred aspect described later.

In addition, the aromatic heterocyclic compound represented by Formula (1a) can be synthesized in the same manner as in the aromatic heterocyclic compound represented by Formula (1).

The compound according to the embodiment of the present disclosure is an aromatic heterocyclic compound represented by any of Formula (10a), Formula (20a), or Formula (30a).

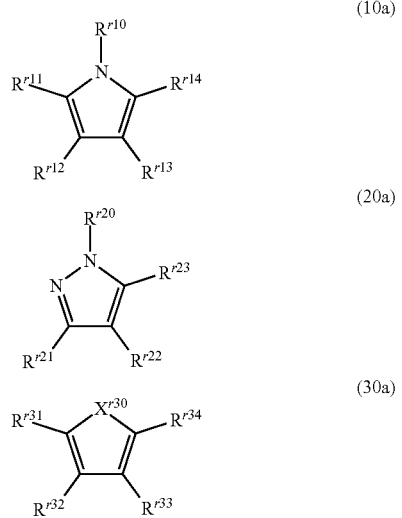

In Formula (10a), any one of $R^{r10}$, $R^{r11}$, $R^{r12}$, $R^{r13}$, or $R^{r14}$ is linked to a group which includes a carbon atom having $Y^A$ in Formula (1a), $R^{r10}$ represents a substituent or $R^A$, $R^{r11}$ to $R^{r14}$ each independently represent a hydrogen atom, a substituent, or $R^A$, and at least one of $R^{r10}$, $R^{r11}$, $R^{r12}$, $R^{r13}$, or $R^{r14}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and $R^{r11}$ and $R^{r12}$, or $R^{r13}$ and $R^{r14}$ may be each independently linked to each other to form a ring or may be each independently linked to each other through a substituent to form a ring.

In Formula (20a), any one of $R^{r20}$, $R^{r21}$, $R^{r22}$, or $R^{r23}$ is linked to a group which includes a carbon atom having $Y^A$ in Formula (1a), $R^{r20}$ represents a substituent or $R^A$, $R^{r21}$ to $R^{r23}$ each independently represent a hydrogen atom, a substituent, or $R^A$, and at least one of $R^{r20}$, $R^{r21}$, $R^{r22}$, or $R^{r23}$ is $R^A$, where $R^A$'s each independently represent an aliphatic hydrocarbon group or an organic group having an aliphatic hydrocarbon group, the number of carbon atoms in each aliphatic hydrocarbon group included in all $R^A$'s is 14 or more, and $R^{r22}$ and $R^{r23}$ may be linked to each other to form a ring or may be linked to each other through a substituent to form a ring.

In Formula (30a), any one of $R^{r31}$, $R^{r32}$, $R^{r33}$, or $R^{r34}$ is linked to a group which includes a carbon atom having $Y^A$ in Formula (1a), $X^{r30}$ represents an oxygen atom or a sulfur atom, $R^{r31}$ to $R^{r34}$ each independently represent a hydrogen atom, a substituent, or $R^A$, and at least one of $R^{r31}$, $R^{r32}$, $R^{r33}$, or $R^{r34}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and $R^{r31}$ and $R^{r32}$, or $R^{r33}$ and $R^{r34}$ may be each independently linked to each other to form a ring or may be each independently linked to each other through a substituent to form a ring.

The aromatic heterocyclic compound represented by any of Formula (10a), Formula (20a), or Formula (30a) according to the present disclosure is the same as the above-described aromatic heterocyclic compound represented by Formula (1), except that the number of carbon atoms in at least one aliphatic hydrocarbon group included in at least one $R^A$ is 14 or more. In addition, the same applies to preferred aspects other than the preferred aspect described later. In addition, it is preferable that the total number of carbon atoms in all aliphatic hydrocarbon groups included in $R^A$, $R^B$, and $R^C$ is 40 or more.

$R^A$ in the compound represented by any of Formula (10a), Formula (20a), or Formula (30a) has the same meaning as $R^A$ in the aromatic heterocyclic compound represented by Formula (1a), and the preferred aspects thereof are also the same.

From the viewpoint of deprotection rate, crystallization property, solubility in a solvent, and yield, the aromatic heterocyclic compound represented by Formula (1a) is preferably the compound represented by any of Formula (10a), Formula (20a), or Formula (30a), more preferably the compound represented by Formula (10a) or Formula (20a), and particularly preferably the compound represented by Formula (10a).

From the viewpoint of deprotection rate, crystallization property, solubility in a solvent, and yield, the compound represented by Formula (10a) is preferably a compound represented by Formula (11a), the compound represented by Formula (20) is preferably a compound represented by Formula (21a), and the compound represented by Formula (30a) is preferably a compound represented by Formula (31a).

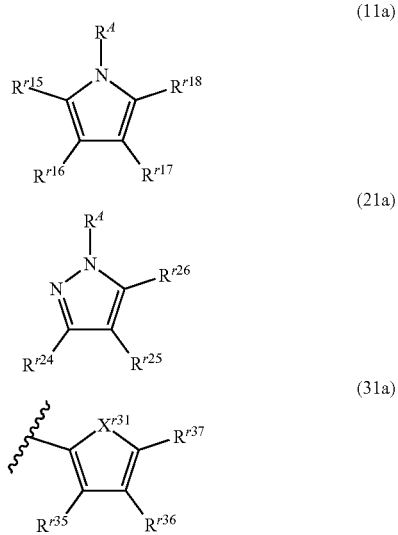

In Formula (11a), any one of $R^{r15}$, $R^{r16}$, $R^{r17}$, or $R^{r18}$ is linked to the group which includes the carbon atom having $Y^A$ in Formula (1a), $R^{r15}$ to $R^{r18}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r15}$ and $R^{r16}$, or $R^{r17}$ and $R^{r18}$ may be each independently linked to each other through a substituent to form a ring.

In Formula (21a), any one of $R^{r24}$, $R^{r25}$, or $R^{r26}$ is linked to the group which includes the carbon atom having $Y^A$ in Formula (1a), $R^{r24}$ to $R^{r26}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in at least one $R^A$ is 14 or more, and $R^{r25}$ and $R^{r26}$ may be linked to each other through a substituent to form a ring.

In Formula (31a), a wavy line portion represents a position linked to the group which includes the carbon atom having $Y^A$ in Formula (1a), $X^{r31}$ represents an oxygen atom or a sulfur atom, $R^{r35}$ to $R^{r37}$ each independently represent a hydrogen atom, a substituent, or $R^A$, $R^A$'s each independently represent an aliphatic hydrocarbon group or an organic group having an aliphatic hydrocarbon group, the number of carbon atoms in at least one aliphatic hydrocarbon group in at least one $R^A$ is 14 or more, and at least one of $R^{r35}$, $R^{r36}$, or $R^{r37}$ is $R^A$ and may be linked to $R^{r36}$ through a substituent to form a ring.

The compound represented by any of Formula (11a), Formula (21a), or Formula (31a) is the same as the compound represented by any of Formula (10), Formula (20), or Formula (30) in the above-described method for producing a peptide compound according to the embodiment of the present disclosure, except that the number of carbon atoms in at least one aliphatic hydrocarbon group included in at least one $R^A$ is 14 or more. In addition, the same applies to preferred aspects other than the preferred aspect described later.

From the viewpoint of deprotection rate, crystallization property, solubility in a solvent, and yield, the aromatic heterocyclic compound represented by Formula (1a) is preferably the compound represented by Formula (11a) or Formula (31a), and more preferably the compound represented by Formula (11a).

In Formula (1a), Formulae (10a) to (30a), and Formulae (11a) to (31a), from the viewpoint of deprotection rate, crystallization property, solubility in a solvent, and yield, the total number of carbon atoms in all aliphatic hydrocarbon groups included in $R^A$, $R^B$, and $R^C$ is preferably 40 to 200, more preferably 40 to 100, and still more preferably 40 to 80.

$R^A$ in the compound represented by any of Formula (11a), Formula (21a), or Formula (31a) has the same meaning as $R^A$ in the aromatic heterocyclic compound represented by Formula (1a), and the preferred aspects thereof are also the same.

EXAMPLES

Hereinafter, the embodiments of the present invention will be more specifically described with reference to Examples. The materials, amounts to be used, proportions, treatment contents, treatment procedures, and the like shown in Examples can be appropriately modified as long as the modifications do not depart from the spirit of the embodiments of the present invention. Therefore, the scope of the embodiments of the present invention is not limited to the following specific examples. In addition, "parts" and "%" are on a mass basis unless otherwise specified.

Unless otherwise specified, purification by column chromatography was performed using an automatic purification device ISOLERA (manufactured by Biotage Ltd.) or a medium pressure liquid chromatograph YFLC-Wprep 2XY.N (manufactured by YAMAZEN).

Unless otherwise specified, SNAPKP-SI1 Cartridge (manufactured by Biotage Ltd.) or a high flash column W001, W002, W003, W004, or W005 (manufactured by YAMAZEN) was used as a carrier in silica gel column chromatography.

The mixing ratio in an eluent used for column chromatography is the volume ratio. For example, "gradient elution of hexane:ethyl acetate=50:50 to 0:100" means that an eluent of 50% hexane and 50% ethyl acetate is finally changed to an eluent of 0% hexane and 100% ethyl acetate.

In addition, "gradient elution of hexane:ethyl acetate=50:50 to 0:100 and gradient elution of methanol:ethyl acetate=0:100 to 20:80" means that an eluent of 50% hexane and 50% ethyl acetate is changed to an eluent of 0% hexane and 100% ethyl acetate, the eluent of 0% hexane and 100% ethyl acetate is switched to an eluent of 0% methanol and 100% ethyl acetate, and then the eluent of 0% methanol and 100% ethyl acetate is finally changed to an eluent of 20% methanol and 80% ethyl acetate.

MS spectrum was measured using ACQUITY SQD LC/MS System (manufactured by Waters Corporation; ionization method; electrospray ionization (ESI) method).

NMR spectrum was measured using Bruker AV300 (manufactured by Bruker, 300 MHz) or Bruker AV400 (manufactured by Bruker, 400 MHz), using tetramethylsilane as an internal reference, and all δ values were shown in ppm.

<Protective Group-Forming Reagent: Synthesis of Compound (1-1)>

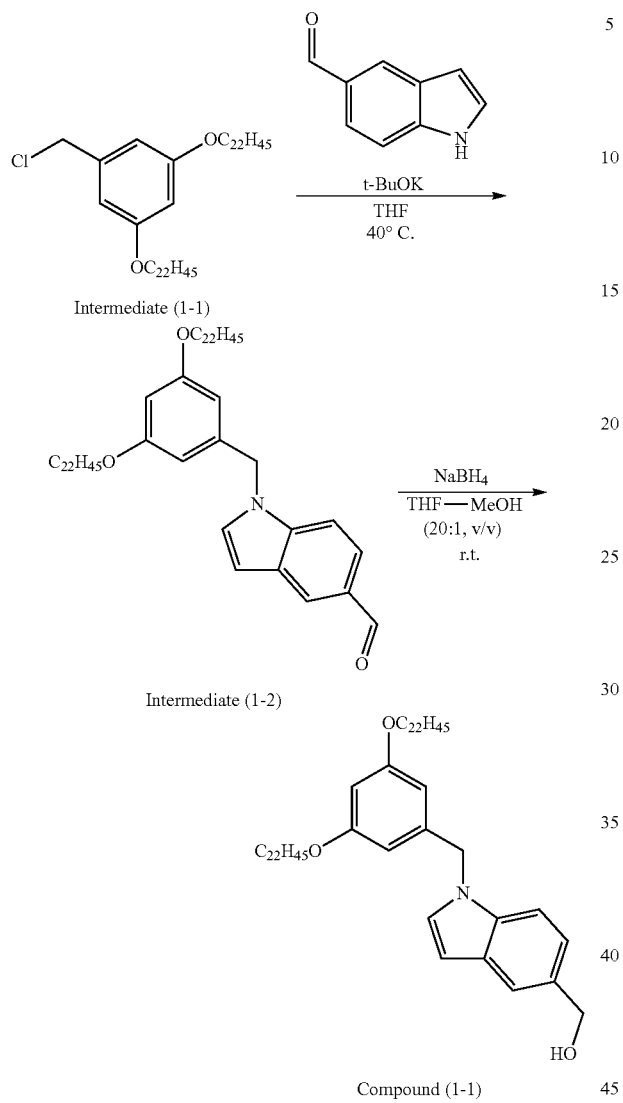

Compound (1-1)

The above-described intermediate (1-1) was synthesized according to the method described in EP2518041B.

The intermediate (1-1) (8.00 g, 10.3 mmol), indole-5-carboxaldehyde (2.99 g, 20.6 mmol), potassium tert-butoxide (2.20 g, 19.6 mmol), and tetrahydrofuran (THF, 100 mL) were mixed, and the mixture was stirred at 40° C. for 3 hours under a nitrogen atmosphere. The reaction solution was cooled to room temperature and extracted with cyclopentyl methyl ether and water, and the organic layer was concentrated under reduced pressure. The obtained crude product was dissolved in dichloromethane, methanol was added to the solution to precipitate solid, and the solid was filtered and dried to obtain an intermediate (1-2) (8.70 g) (yield: 95%).

Under a nitrogen atmosphere, the intermediate (1-2) (5.00 g, 5.65 mmol), sodium borohydride (0.43 g, 11.3 mmol), and tetrahydrofuran/methanol (20/1 (vol %/vol %), 63 mL) were mixed, and the mixture was stirred for at room temperature 2 hours. The reaction solution was cooled to 0° C., water (10 mL) was slowly added dropwise thereto to terminate (quench) the reaction. The mixture was extracted with dichloromethane, and the obtained organic layer was washed with water and saturated saline in this order, and concentrated under reduced pressure. The obtained crude product was dissolved in dichloromethane, methanol was added to the solution to precipitate solid, and the solid was filtered and dried to obtain a compound (1-1) (4.62 g) (yield: 92%).

r.t stands for room temperature, t-BuOK stands for potassium tert-butoxide, THF stands for tetrahydrofuran, and MeOH stands for methanol.

$^1$H NMR (CDCl$_3$: 400 MHz): δ: 0.82 to 1.76 (86H, m), 3.83 (4H, t), 4.76 (2H, d), 5.22 (2H, s), 6.24 (2H, d), 6.33 (1H, t), 6.53 (1H, t), 7.14 (1H, d), 7.20 (1H, dd), 7.29 (1H, d), 7.63 (1H, d)

<Synthesis of Protective Group-Forming Reagents (Compounds (1-2) to (1-6))>

Compounds (1-2) to (1-6) shown below were obtained by synthesizing in the same manner as in the compound (1-1).

Compound (1-2)

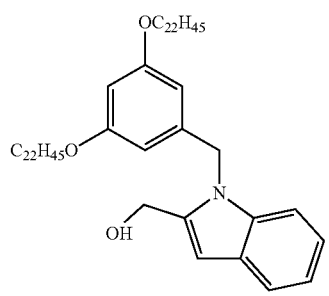

Compound (1-3)

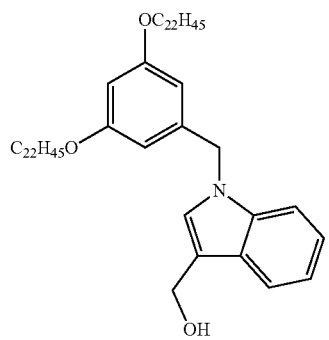

Compound (1-4)

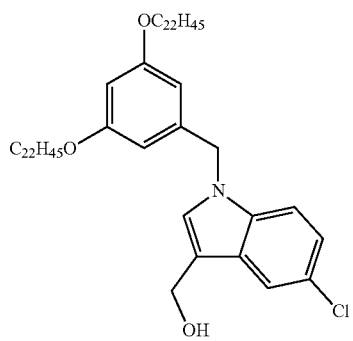

-continued

Compound (1-5)

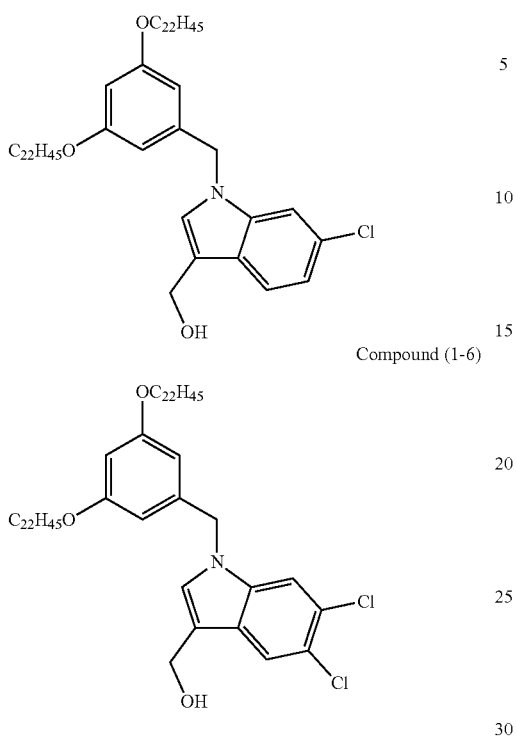

Compound (1-6)

The ¹H NMR results of the compound (1-2) are shown below.

¹H NMR (CDCl₃: 400 MHz): δ: 0.88 (6H, t), 1.20 to 1.74 (80H, m), 3.81 (4H, t), 4.74 (2H, d), 5.39 (2H, s), 6.14 (2H, d), 6.30 (1H, t), 6.53 (1H, s), 7.10 (1H, t), 7.16 (1H, t), 7.25 to 7.30 (1H, d), 7.61 (1H, d)

The ¹H NMR results of the compound (1-3) are shown below.

¹H NMR (CDCl₃: 400 MHz): δ: 0.88 (6H, t), 1.20 to 1.74 (80H, m), 3.84 (4H, t), 4.88 (2H, d), 5.18 (2H, s), 6.28 (2H, d), 6.35 (1H, t), 6.53 (1H, s), 7.13 to 7.28 (3H, m), 7.31 (1H, d), 7.75 (1H, d)

The ¹H NMR results of the compound (1-4) are shown below.

¹H NMR (CDCl₃: 400 MHz): δ: 0.88 (6H, t), 1.19 to 1.47 (76H, m), 1.66 to 1.76 (4H, m), 3.84 (4H, t), 4.83 (2H, d), 5.15 (2H, s), 6.23 (2H, d), 6.35 (1H, t), 7.12 to 7.16 (2H, m), 7.17 to 7.21 (1H, m), 7.69 to 7.72 (1H, m)

The ¹H NMR results of the compound (1-5) are shown below.

¹H NMR (CDCl₃: 400 MHz): δ: 0.88 (6H, t), 1.18 to 1.47 (76H, m), 1.66 to 1.77 (4H, m), 3.86 (4H, t), 4.84 (2H, d), 5.13 (2H, s), 6.24 (2H, d), 6.36 (1H, t), 7.08 to 7.13 (2H, m), 7.28 (1H, d), 7.64 (1H, d)

The ¹H NMR results of the compound (1-6) are shown below.

¹H NMR (CDCl₃: 400 MHz): δ: 0.88 (6H, t), 1.18 to 1.45 (76H, m), 1.48 (1H, t), 1.67 to 1.77 (4H, m), 3.86 (4H, t), 4.82 (2H, d), 5.12 (2H, s), 6.21 (2H, d), 6.36 (1H, t), 7.12 (1H, s), 7.37 (1H, s), 7.81 (1H, s)

<Synthesis of Protective Group-Forming Reagent (Compound (1-N-1))>

A compound (1-N-1) was synthesized according to the following scheme.

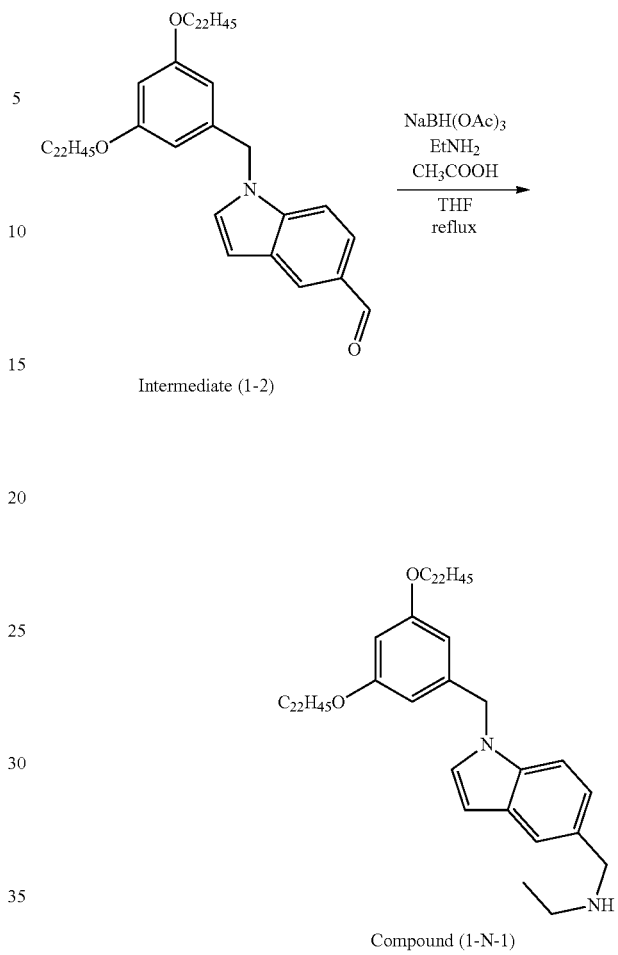

Intermediate (1-2)

Compound (1-N-1)

The intermediate (1-2) synthesized above (2.00 g, 2.26 mmol), sodium triacetoxyborohydride (0.96 g, 4.52 mmol), ethylamine tetrahydrofuran solution (2M) (3.39 mL, 6.78 mmol), acetic acid (0.34 mL, 6.78 mmol), and tetrahydrofuran (25 mL) were mixed, and the mixture was stirred at 90° C. for 7 hours under a nitrogen atmosphere. The reaction solution was cooled to 0° C., water (10 mL) was slowly added dropwise thereto to quench. The mixture was extracted with dichloromethane, and the obtained organic layer was washed with a saturated sodium hydrogen carbonate aqueous solution, and concentrated under reduced pressure. The obtained crude product was dissolved in dichloromethane, methanol was added to the solution to precipitate solid, and the solid was filtered and dried to obtain the compound (1-N-1) (1.90 g, yield: 94%).

NaBH(OAc)₃ stands for sodium triacetoxyborohydride, and EtNH₂ stands for ethylamine.

¹H NMR (CDCl₃, 400 MHz): δ: 0.88 (6H, t), 1.15 (3H, t), 1.20 to 1.76 (80H, m), 2.72 (2H, q), 3.83 (4H, t), 3.89 (2H, s), 5.19 (2H, s), 6.24 (2H, d), 6.32 (1H, t), 6.49 (1H, dd), 7.11 (1H, d), 7.15 (1H, dd), 7.25 (2H, d), 7.57 (1H, d)

<Synthesis of Protective Group-Forming Reagents (Compounds (1-N-2) to (1-N-4))>

Compounds (1-N-2) to (1-N-4) shown below were obtained by synthesizing in the same manner as in the compound (1-N-1).

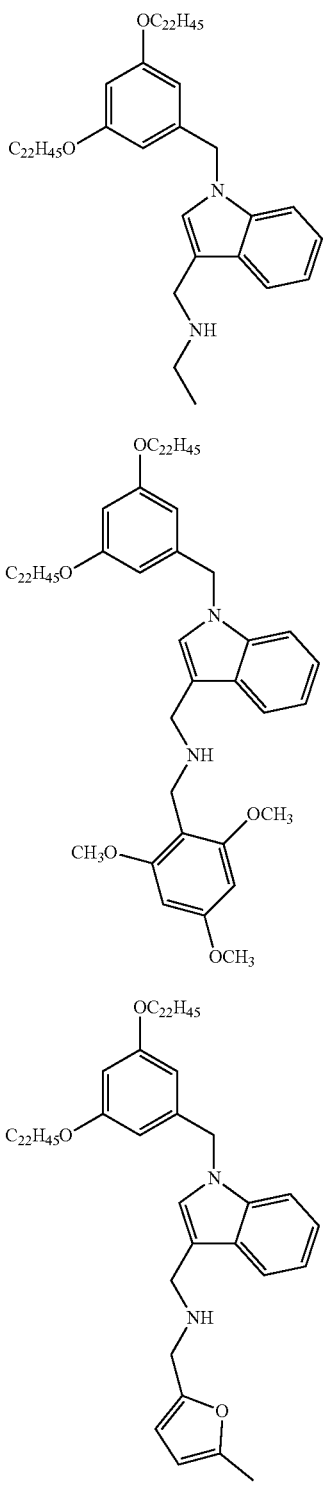

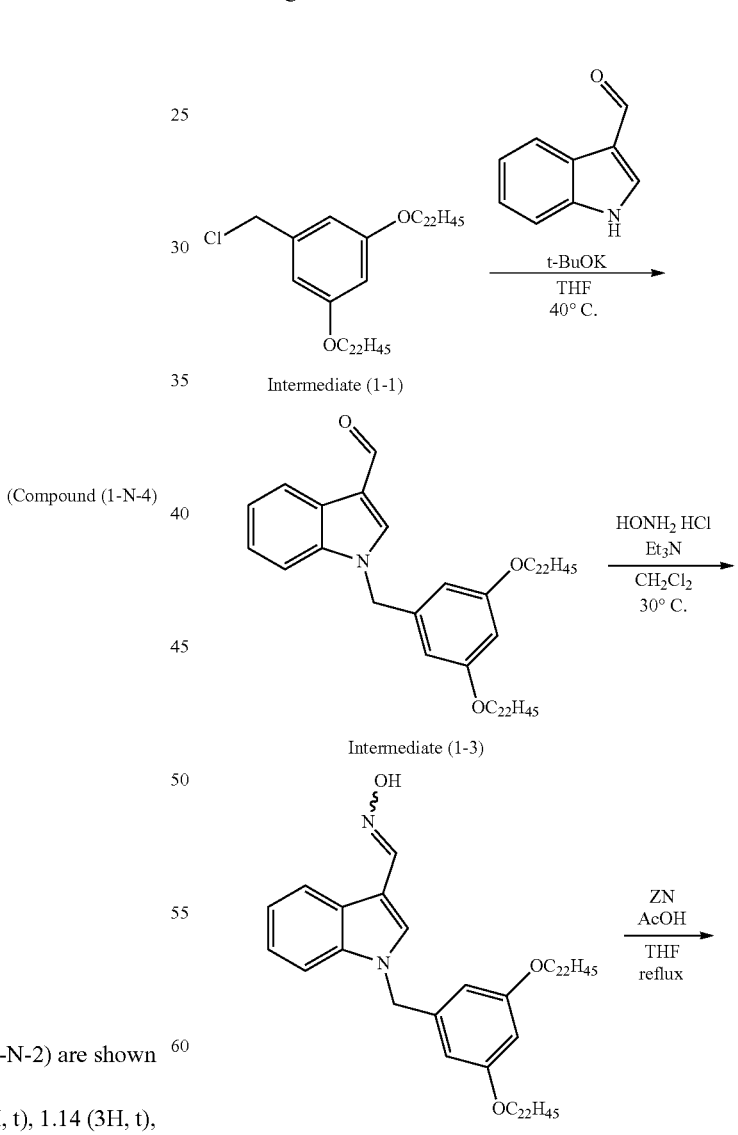

The $^1$H NMR results of the compound (1-N-2) are shown below.

$^1$H NMR (CDCl$_3$: 400 MHz): δ: 0.88 (6H, t), 1.14 (3H, t), 1.18 to 1.44 (76H, m), 1.66 to 1.74 (4H, m), 2.75 (2H, q), 3.83 (4H, t), 3.99 (2H, s), 5.17 (2H, s), 6.26 (2H, d), 6.33 (11H, t), 7.07 (1H, s), 7.11 (1H, t), 7.17 (1H, t), 7.25 to 7.29 (1H, m), 7.65 (1H, d)

The $^1$H NMR results of the compound (1-N-3) are shown below.

$^1$H NMR (CDCl$_3$: 400 MHz): δ: 0.88 (6H, t), 1.22 to 1.43 (76H, m), 1.64 to 1.72 (4H, m), 3.74 (6H, s), 3.82 (4H, d), 3.82 (3H, s), 3.95 (4H, d), 5.16 (2H, s), 6.13 (2H, s), 6.26 (2H, d), 6.31 (11H, t), 7.07 (1H, td), 7.15 (1H, td), 7.15 (11H, s), 7.24 to 7.28 (1H, m), 7.50 (1H, d)

The $^1$H NMR results of the compound (1-N-4) are shown below.

$^1$H NMR (CDCl$_3$: 400 MHz): δ: 0.88 (6H, t), 1.21 to 1.44 (76H, m), 1.65 to 1.74 (4H, m), 2.28 (3H, s), 3.78 (2H, s), 3.83 (4H, t), 3.99 (2H, s), 5.17 (2H, s), 5.87 to 5.90 (1H, m), 6.05 (1H, d), 6.26 (2H, d), 6.33 (1H, t), 7.07 (1H, s), 7.10 (1H, td), 7.18 (1H, td), 7.24 to 7.29 (1H, m), 7.63 (1H, d)

<Synthesis of Protective Group-Forming Reagent (Compound (1-N-5))>

A compound (1-N-5) was synthesized according to the following scheme.

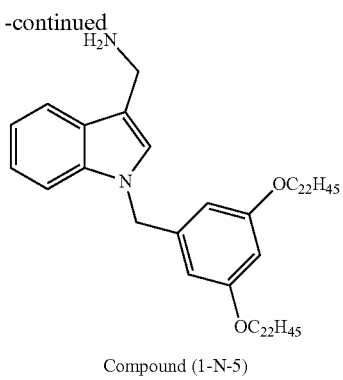

Compound (1-N-5)

A mixture of the intermediate (1-1) (10.0 g, 12.9 mmol), indole-3-carbaldehyde (7.48 g, 51.6 mmol), and tetrahydrofuran (129 mL) was added to potassium tert-butoxide (5.79 g, 51.6 mmol), and the mixture was stirred at 60° C. for 2.5 hours. Cyclopentyl methyl ether (250 mL) and water (250 mL) were added to the reaction solution, and after separation, methanol (1 L) was added to the organic layer, and then the resulting precipitate was collected by filtration and dried to obtain an intermediate (1-3) (11.1 g, yield: 96.9%).

The intermediate (1-3) (20.0 g, 22.6 mmol) was dissolved in methylene chloride (302 mL) at 30° C., hydroxylamine hydrochloride (9.43 g, 136 mmol) and triethylamine (31.5 mL, 226 mmol) were added thereto, and the mixture was stirred at 30° C. for 2 hours. The reaction solution was cooled to room temperature, methanol (2 L) was added thereto, and the resulting precipitate was collected by filtration and dried to obtain an intermediate (1-4) (19.6 g, yield: 96.6%).

After mixing the intermediate (1-4) (2.00 g, 2.22 mmol), tetrahydrofuran (37 mL), and acetic acid (10 mL) at room temperature, zinc dust (1.75 g, 26.7 mmol) was added thereto. After refluxing for 1 hour, zinc dust was removed with Celite, and the obtained filtrate was concentrated. Methanol (750 mL) was added to the obtained crude product, and the resulting precipitate was collected by filtration and dried. The obtained solid was purified by column chromatography (NH silica gel, hexane:ethyl acetate=4:1 to 1:9) to obtain the compound (1-N-5) (1.01 g, yield: 51.3%).

$^1$H NMR (CDCl$_3$, 400 MHz): δ: 0.88 (6H, t), 1.20 to 1.44 (76H, m), 1.66 to 1.75 (4H, m), 3.84 (4H, t), 4.06 (2H, d), 5.17 (2H, s), 6.27 (2H, d), 6.33 (1H, t), 7.04 (1H, s), 7.12 (1H, dt), 7.19 (1H, dt), 7.29 (1H, d), 7.65 (1H, d)

<Synthesis of Protective Group-Forming Reagent (Compound (1-N-2-1))>

A compound (1-N-2-1) was synthesized according to the following scheme.

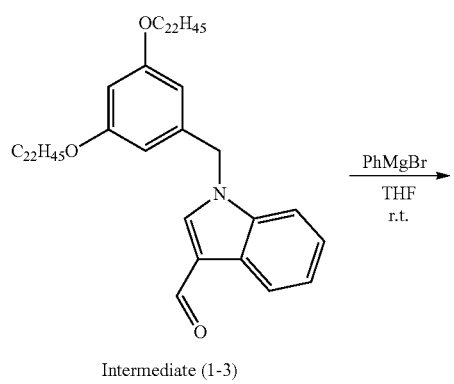

Intermediate (1-3)

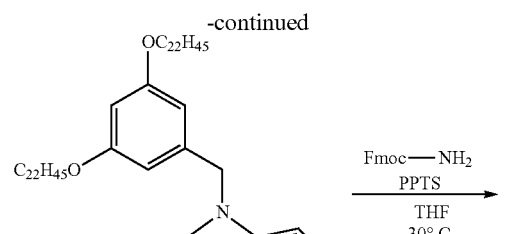

Intermediate (1-4)

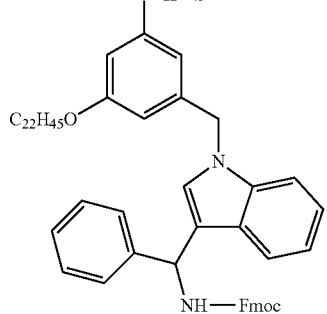

Intermediate (1-5)

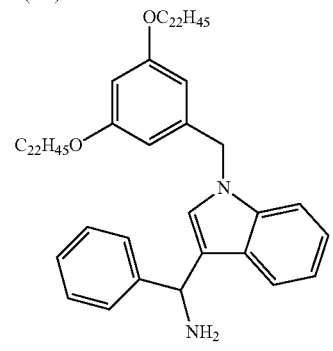

Compound (1-N-2-1)

Under a nitrogen atmosphere, the intermediate (1-3) (1.00 g, 1.13 mmol) was dissolved in tetrahydrofuran (5.7 mL), phenylmagnesium bromide (1.0 mM tetrahydrofuran solution, 1.70 mL, 1.70 mmol) was added thereto, and the mixture was stirred at room temperature for 30 minutes. 2-Me-THF (8 mL) and a saturated ammonium chloride aqueous solution (8 mL) were added to the reaction solution, and the organic layer was washed with a saturated ammonium chloride aqueous solution and saturated saline. The organic layer was dried over anhydrous magnesium sulfate and concentrated under reduced pressure. Methanol was added to the obtained crude product to precipitate solid, and the solid was filtered and dried to obtain an intermediate (1-4) (1.04 g, yield: 96%).

The intermediate (1-4) (200 mg, 0.21 mmol) and 9-fluorenylmethyl carbamic acid (199 mg, 0.83 mmol) were dissolved in tetrahydrofuran (2.0 mL), pyridinium p-toluenesulfonate (5.2 mg, 21 mol) was added thereto, and the mixture was stirred at 30° C. for 5 hours. Methanol was added to the reaction solution to precipitate solid, and the solid was washed with methanol and hexane, filtered, and dried under to obtain an intermediate (1-5) (286 mg, including 9-fluorenylmethyl carbamate).

The intermediate (1-5) (286 mg, including 9-fluorenylmethyl carbamate) was dissolved in tetrahydrofuran (2.9 mL), DBU (0.14 mL, 0.96 mmol) was added thereto, and the mixture was stirred at room temperature for 20 minutes. Methanol was added to the reaction solution to precipitate solid, and the solid was washed with methanol and hexane, filtered, and dried under to obtain the compound (1-N-2-1) (105 mg, 2-step yield: 53%).

The $^1$H NMR results of the compound (1-N-2-1) are shown below.

$^1$H NMR (CDCl$_3$, 400 MHz): δ: 0.88 (6H, t), 1.20 to 1.46 (76H, m), 1.66 to 1.75 (4H, m), 1.86 (2H, br), 3.83 (4H, t), 5.17 (2H, s), 5.49 (1H, br), 6.24 (2H, d), 6.32 (1H, t), 7.01 (1H, t), 7.04 (1H, s), 7.13 (1H, t), 7.20 to 7.34 (4H, m), 7.44 to 7.48 (3H, m)

<Synthesis of Protective Group-Forming Reagents (Compounds (1-N-2-2) and (1-N-2-3))>

Compounds (1-N-2-2) and (1-N-2-3) shown below were obtained by synthesizing in the same manner as in the compound (1-N-2-1).

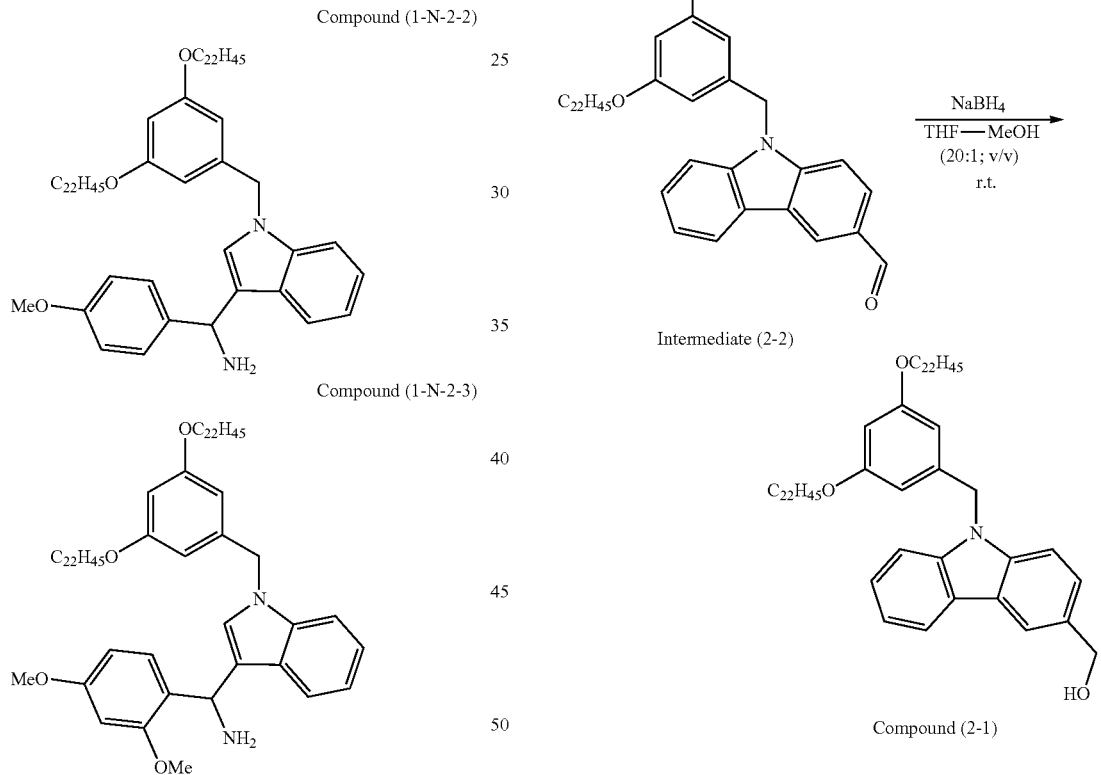

The $^1$H NMR results of the compound (1-N-2-2) are shown below.

$^1$H NMR (CDCl$_3$, 400 MHz): δ: 0.88 (6H, t), 1.22 to 1.45 (76H, m), 1.66 to 1.75 (4H, m), 3.79 (3H, s), 3.83 (4H, t), 5.17 (2H, s), 5.45 (1H, s), 6.25 (2H, d), 6.33 (1H, t), 6.83 to 6.86 (2H, m), 7.00 (1H, t), 7.04 (1H, s), 7.13 (1H, t), 7.22 to 7.28 (1H, m), 7.35 to 7.39 (2H, m), 7.43 (1H, d)

The $^1$H NMR results of the compound (1-N-2-3) are shown below.

$^1$H NMR (CDCl$_3$, 400 MHz): δ: 0.88 (6H, t), 1.23 to 1.45 (76H, m), 1.66 to 1.75 (4H, m), 3.77 (3H, s), 3.83 (4H, t), 3.85 (3H, s), 5.19 (2H, s), 5.74 (1H, br), 6.26 (2H, d), 6.32 (1H, t), 6.34 (1H, dd), 6.48 (1H, d), 6.99 (1H, t), 7.06 to 7.15 (3H, m), 7.23 to 7.27 (1H, m), 7.41 (1H, d)

<Synthesis of Protective Group-Forming Reagent (Compound (2-1))>

A compound (2-1) was synthesized according to the following scheme.

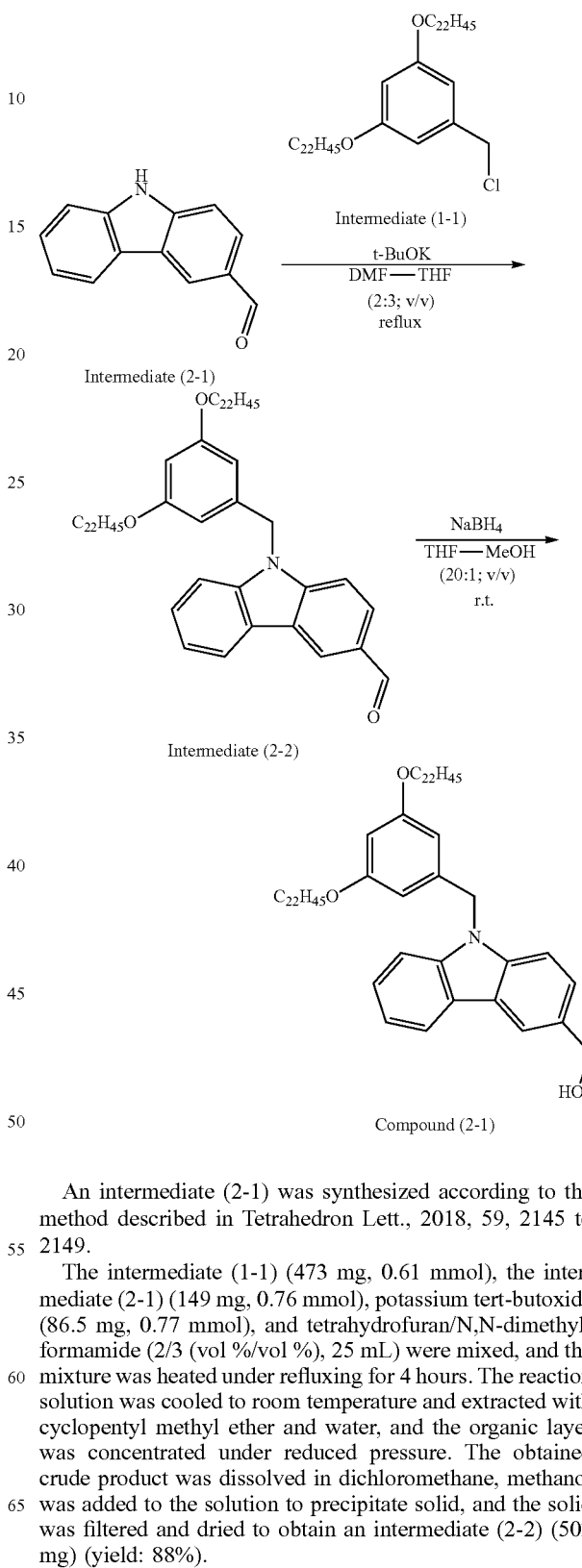

An intermediate (2-1) was synthesized according to the method described in Tetrahedron Lett., 2018, 59, 2145 to 2149.

The intermediate (1-1) (473 mg, 0.61 mmol), the intermediate (2-1) (149 mg, 0.76 mmol), potassium tert-butoxide (86.5 mg, 0.77 mmol), and tetrahydrofuran/N,N-dimethylformamide (2/3 (vol %/vol %), 25 mL) were mixed, and the mixture was heated under refluxing for 4 hours. The reaction solution was cooled to room temperature and extracted with cyclopentyl methyl ether and water, and the organic layer was concentrated under reduced pressure. The obtained crude product was dissolved in dichloromethane, methanol was added to the solution to precipitate solid, and the solid was filtered and dried to obtain an intermediate (2-2) (503 mg) (yield: 88%).

Under a nitrogen atmosphere, the intermediate (2-2) (149 mg, 0.16 mmol), sodium borohydride (12.1 mg, 0.32 mmol), and tetrahydrofuran/methanol (20/1 (vol %/vol %), 2 mL) were mixed, and the mixture was stirred for at room temperature 2 hours. The reaction solution was cooled to 0° C., water (10 mL) was slowly added dropwise thereto to quench. The mixture was extracted with dichloromethane, and the obtained organic layer was washed with water and saturated saline, and concentrated under reduced pressure. The obtained crude product was dissolved in dichloromethane, methanol was added to the solution to precipitate solid, and the solid was filtered and dried to obtain a compound (2-1) (115 mg) (yield: 77%).

DMF stands for N,N-dimethylformamide.

$^1$H NMR (CDCl$_3$: 400 MHz): δ: 0.84 to 1.72 (86H, m), 3.80 (4H, t), 4.86 (2H, d), 5.42 (2H, s), 6.27 (2H, d), 6.31 (1H, t), 7.22 to 7.29 (2H, m), 7.33 to 7.39 (2H, m), 7.41 to 7.47 (2H, m), 8.10 to 8.14 (2H, m)

<Synthesis of Protective Group-Forming Reagent (Compound (3-1))>

A compound (3-1) was synthesized according to the following scheme.

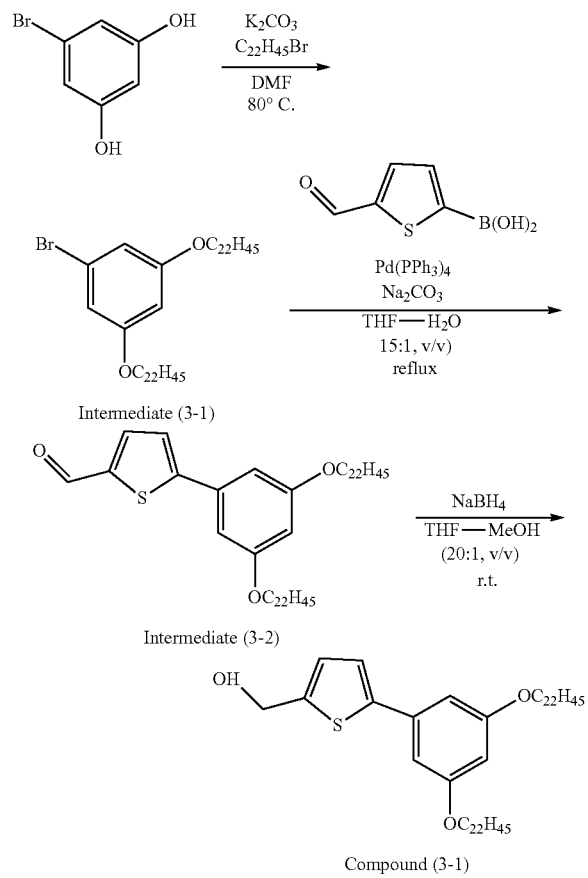

5-bromoresorcinol (1.89 g, 10.0 mmol), 1-bromodocosane (7.78 g, 20.0 mmol), potassium carbonate (8.98 g, 65.0 mmol), and N,N-dimethylformamide (300 mL) were mixed, and the mixture was stirred at 80° C. for 5 hours under a nitrogen atmosphere. The reaction solution was cooled to room temperature and extracted with chloroform and water, and the organic layer was concentrated under reduced pressure. The obtained crude product was dissolved in chloroform, methanol was added to the solution to precipitate solid, and the solid was filtered and dried to obtain an intermediate (3-1) (5.20 g, yield: 65%).

Under a nitrogen atmosphere, the intermediate (3-1) (1.61 g, 2.00 mmol), 5-formyl-2-thiophenboronic acid (0.94 g, 6.00 mmol), sodium carbonate (0.76 g, 7.2 mmol), and tetrahydrofuran/water (15/1 (vol %/vol %), 64 mL) were mixed, and the mixture was degassed under reduced pressure while stirring at room temperature. Tetrakis(triphenylphosphine) palladium(0) (0.23 g, 0.20 mmol) was added thereto, and the mixture was heated under refluxing for 14 hours. The reaction solution was cooled to room temperature and filtered through Celite, and the filtrate was concentrated under reduced pressure. The obtained crude product was purified by subjecting the obtained crude product to silica gel chromatography (eluent: hexane/ethyl acetate=95:5 to hexane/ethyl acetate=50:50). The obtained solid was recrystallized with methanol, filtered, and dried to obtain an intermediate (3-2) (0.93 g, yield: 55%).

Under a nitrogen atmosphere, the intermediate (3-2) (586 mg, 0.70 mmol), sodium borohydride (53.0 mg, 1.40 mmol), and tetrahydrofuran/methanol (20/1 (vol %/vol %), 7.4 mL) were mixed, and the mixture was stirred for at room temperature 2 hours. The reaction solution was cooled to 0° C., water (10 mL) was slowly added dropwise thereto to quench. The mixture was extracted with dichloromethane, and the obtained organic layer was washed with water and saturated saline, and concentrated under reduced pressure. The obtained crude product was dissolved in dichloromethane, methanol was added to the solution to precipitate solid, and the solid was filtered and dried to obtain a compound (3-1) (528 mg, yield: 90%).

$^1$H NMR (CDCl$_3$: 400 MHz): δ: 0.82 to 1.84 (86H, m), 3.96 (4H, t), 4.82 (2H, s), 6.39 (1H, t), 6.71 (2H, d), 6.96 (1H, d), 7.14 (1H, d)

<Synthesis of Protective Group-Forming Reagent (Compound (4-1))>

A compound (4-1) was synthesized according to the following scheme.

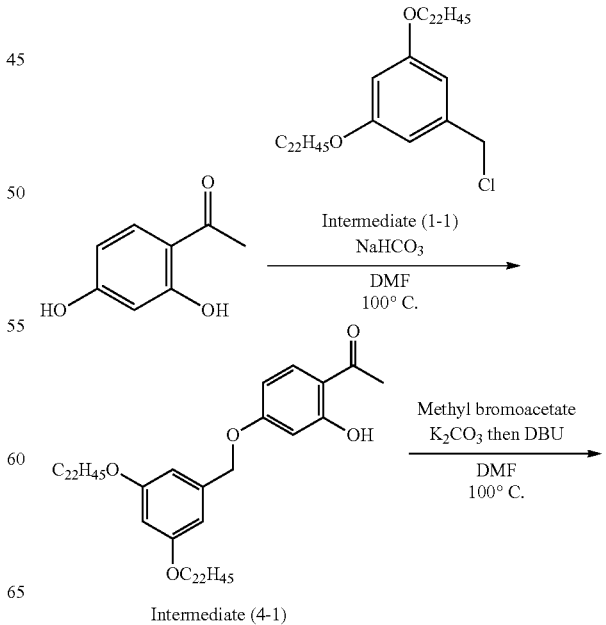

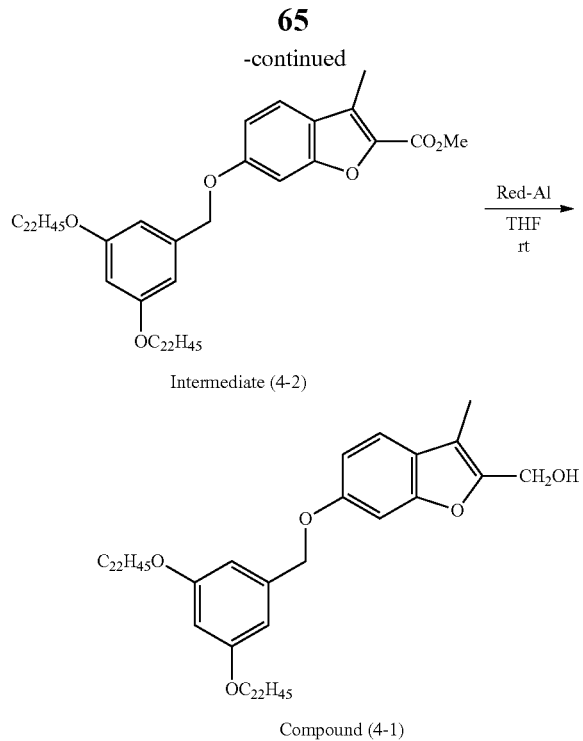

Intermediate (4-2)

Compound (4-1)

2,4-dihydroxyacetophenone (3.92 g, 25.8 mmol), sodium bicarbonate (3.92 g, 25.8 mmol), the intermediate (1-1) (3.92 g, 12.9 mmol), and dimethylformamide (100 mL) were mixed, and the mixture was stirred at 100° C. for 6 hours. The reaction solution was heated to room temperature, 2-methyltetrahydrofuran, tetrahydrofuran, and 100 mL of distilled water were added thereto, and after separation, the upper layer was added to methanol. The resulting solid was filtered and dried to obtain an intermediate (4-1) (11.0 g) (yield: 95%).

The intermediate (4-1) (8.75 g, 9.25 mmol), potassium carbonate (2.28 g, 16.5 mmol), methyl bromoacetate (1.56 mL, 16.5 mmol), and dimethylformamide (100 mL) were mixed, and the mixture was stirred at an outside temperature of 100° C. for 30 minutes. Diazabicycloundecene (4.96 ml, 33.0 mmol) was added to the resulting reaction solution, and the mixture was further stirred at an outside temperature of 100° C. for 4 hours. After cooling the reaction solution, tetrahydrofuran (200 mL) and a saturated ammonium chloride aqueous solution (100 mL) was added thereto for separation, the organic layer was added to methanol (300 mL), and the resulting solid was filtered and dried to obtain a mixture (8.75 g) including an intermediate (4-2) as a main component. This intermediate (4-2) (8.00 g, 8.46 mmol) was dissolved in tetrahydrofuran (80 mL), the mixture was stirred at 45° C. under a nitrogen stream, and then a toluene solution (3.6 M (=3.6 mol/L)) of bis(2-methoxyethoxy) aluminum sodium (5.9 mL, 21.2 mmol) was added dropwise thereto. The reaction solution was stirred at 45° C. for 30 minutes, acetone (8 mL) was added dropwise thereto, a saturated aqueous solution (80 mL) of potassium sodium tartrate was gently added dropwise thereto, the mixture was separated, methanol was added to the obtained organic layer to precipitate solid, and the solid was filtered and dried to obtain a crude product of the compound (4-1). This crude product was purified by silica gel column chromatography (eluent: hexane/ethyl acetate=89:11 to hexane/ethyl acetate=69:31) to obtain the compound (4-1) (2.43 g, yield: 31%).

$^1$H NMR (CDCl$_3$, 400 MHz): δ: 0.88 (6H, t), 1.19 to 1.82 (80H, m), 2.12 (3H, s), 3.94 (4H, t), 4.69 (2H, d), 5.12 (2H, s), 6.38 (1H, t), 6.57 (2H, d), 6.92 (1H, dd), 7.00 (1H, s), 7.33 (1H, d)

<Synthesis of Protected Amino Acid Compound (N-Terminal and C-Terminal Protected Amino Acid (1-1))>

An N-terminal and C-terminal protected amino acid (1-1) was synthesized according to the following scheme.

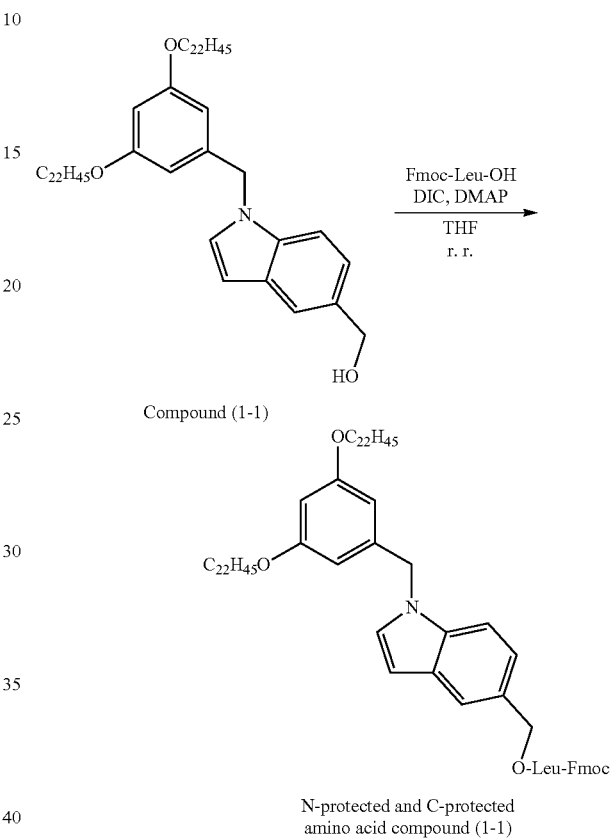

Compound (1-1)

N-protected and C-protected amino acid compound (1-1)

The compound (1-1) (886 mg, 1.00 mmol), N-[(9H-fluoren-9-ylmethoxy)carbonyl]-L-leucine (530 mg, 1.50 mmol), and tetrahydrofuran (10 mL) were mixed at room temperature, and 4-dimethylaminopyridine (24.4 mg, 0.20 mmol) and diisopropylcarbodiimide (232 L, 1.50 mmol) were added thereto. After stirring the reaction solution at room temperature for 1 hour under a nitrogen atmosphere, methanol (50 mL) was added thereto to precipitate solid, and the solid was filtered and dried under reduced pressure to obtain an N-protected and C-protected amino acid (1-1) (1160 mg, yield: 97%).

Fmoc represents a 9-fluorenylmethoxycarbonyl group, and Leu represents a leucine residue.

<Synthesis of Protected Amino Acid Compounds (N-Terminal and C-Terminal Protected Amino Acids (1-2) to (1-6), (2-1), (3-1), and (4-1), and N-Terminal and C-Terminal Protected Amino Acid Comparative Example Compounds (1) and (2))>

Same as the method for synthesizing the N-protected and C-protected amino acid (1-1), N-protected and C-protected amino acids (1-2) to (1-6), (2-1), (3-1), and (4-1), and N-terminal and C-terminal protected amino acid comparative example compounds (1) and (2) were synthesized by condensing with N-[(9H-fluoren-9-ylmethoxy)carbonyl]-L-leucine, except that the compound (1-2), the compound (1-3), the compound (1-4), the compound (1-5), the compound (1-6), the compound (2-1), the compound (3-1), the compound (4-1), a comparative example compound (1) described later, or a comparative example compound (2) described later was used instead of the compound (1-1).

<Synthesis of Protected Amino Acid Compound (N-Terminal and C-Terminal Protected Amino Acid (1-N-1))>

An N-terminal and C-terminal protected amino acid (1-N-1) was synthesized according to the following scheme.

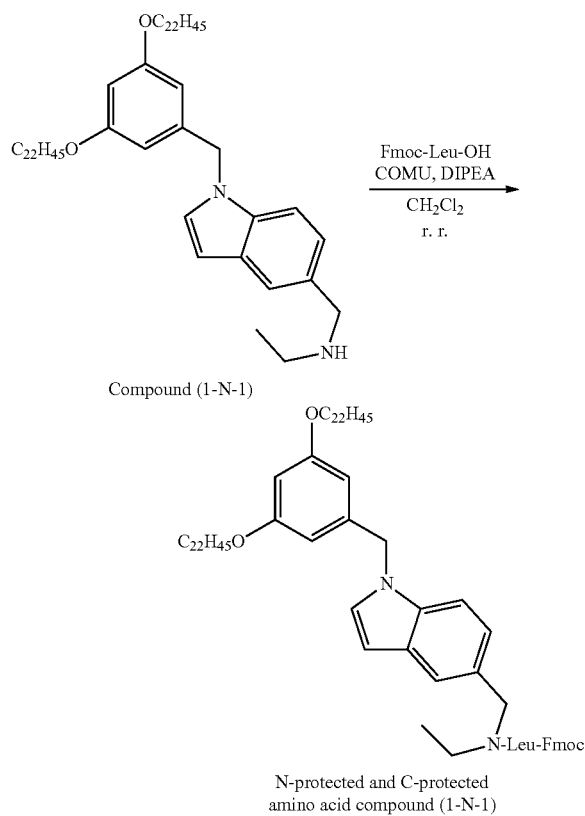

Compound (1-N-1)

N-protected and C-protected amino acid compound (1-N-1)

The compound (1-N-1) (94.4 mg, 0.10 mmol), N-[(9H-fluoren-9-ylmethoxy)carbonyl]-L-leucine (53.0 mg, 0.15 mmol), and dichloromethane (1 mL) were mixed, and diisopropylethylamine (DIPEA, 2.2 molar equivalent) and (1-cyano-2-ethoxy-2-oxoethylidenaminooxy)dimethyl-amino-morpholino-carbenium hexafluorophosphate (COMU, 1.5 molar equivalent) were added thereto. After stirring the reaction solution at room temperature for 1 hour under a nitrogen atmosphere, methanol (5 mL) was added thereto to precipitate solid, and the solid was filtered and dried to obtain an N-terminal and C-terminal protected amino acid (1-N-1) (116 mg, yield: 93%).

<Synthesis of Protected Amino Acid Compounds (N-Terminal and C-Terminal Protected Amino Acids (1-N-2), (1-N-3), (1-N-5), (1-N-2-1), (1-N-2-2), and (1-N-2-3) and N-Terminal and C-Terminal Protected Amino Acid Comparative Example Compounds (3) and (4))>

Same as the method for synthesizing the N-protected and C-protected amino acid (1-N-1), N-protected and C-protected amino acids (1-N-2), (1-N-3), (1-N-5), (1-N-2-1), (1-N-2-2), and (1-N-2-3), and N-terminal and C-terminal protected amino acid comparative example compounds (3) and (4) were synthesized by condensing with N-[(9H-fluoren-9-ylmethoxy)carbonyl]-L-leucine, except that the compound (1-N-2), the compound (1-N-3), the compound (1-N-5), the compound (1-N-2-1), the compound (1-N-2-2), the compound (1-N-2-3), a comparative example compound (3), or a comparative example compound (4) described later was used instead of the compound (1-N-1).

Examples 1 to 9 and Comparative Examples 1 and 2

(Evaluation 1)
<Deprotection Rate>

With regard to the compounds of Examples and Comparative Examples synthesized above, which are shown in Table 1, the deprotection ratio (deprotection ratio of C-terminal end) of the protected carboxylic acid moiety was determined as follows.

100 mg of Fmoc-Leu-OTag (N-terminal and C-terminal protected amino acids (1-1) to (1-5), (2-1), and (3-1), and N-terminal and C-terminal protected amino acids using the compounds (1) and (2) of Comparative Examples) and Fmoc-Gly-OH (internal standard) in an equimolar amount of Fmoc-Leu-OTag were mixed, and then dichloromethane/trifluoroethanol/trifluoroacetic acid (100/10/1: vol %) was added thereto so that the substrate concentration was 0.026 M based on Fmoc-Leu-OTag, and the mixture was stirred at 30° C. for 60 minutes.

20 μL of the reaction solution was dissolved in 400 L of methanol (MeOH), and using Ultra Performance LC (ultra-performance liquid chromatography, manufactured by Waters Corporation, model number: ACQUITY), the deprotection ratio (%) was determined by quantifying the ratio of Fmoc-Leu-OH and Fmoc-Gly-OH produced by deprotecting Fmoc-Leu-OTag, and evaluated based on the following standard.

The columns and measurement conditions used for the ultra-performance liquid chromatography are shown below.

Column: manufactured by Waters Corporation, model number: BEH C18 1.7 μm, 2.1 mm×30 mm Flow rate: 0.5 mL/min Solvent: solution A: 0.1% formic acid-water, solution B: 0.1% formic acid-acetonitrile Gradient cycle: 0.00 min (solution A/solution B=95/5), 2.00 min (solution A/solution B=5/95), 3.00 min (solution A/solution B=95/5)

Detection wavelength: 254 nm

Regarding the evaluation of the deprotection rate, a case of "B" or higher was regarded as acceptable. The results are shown in Table 1.

It can be said that, as the deprotection ratio is higher, the deprotection rate is higher and the deprotection rate is excellent.

—Evaluation Standard—

"A": deprotection ratio was 80% or more.

"B": deprotection ratio was 50% or more and less than 80%.

"C": deprotection ratio was 20% or more and less than 50%.

"D": deprotection ratio was less than 20%.

TABLE 1

|  | Type of protective group | Deprotection rate |
|---|---|---|
| Example 1 | Compound (1-1) | B |
| Example 2 | Compound (1-2) | B |
| Example 3 | Compound (1-3) | A |
| Example 4 | Compound (1-4) | A |

TABLE 1-continued

| | Type of protective group | Deprotection rate |
|---|---|---|
| Example 5 | Compound (1-5) | A |
| Example 6 | Compound (2-1) | B |
| Example 7 | Compound (3-1) | A |
| Example 8 | Compound (4-1) | A |
| Example 9 | Compound (1-6) | A |
| Comparative example 1 | Comparative compound (1) | D |
| Comparative example 2 | Comparative compound (2) | D |

Details of the compounds in Table 1 are as follows.

Comparative compound (1): 3,4,5-tris-(n-octadecyloxy) benzyl alcohol (synthesized according to the method described in paragraphs 0015 and 0016 of JP2000-44493A)

Comparative compound (2): 3,5-bis(docosyloxy)benzyl alcohol (synthesized according to the method described in paragraph 0104 of JP2009-185063A)

As shown in Table 1, the aromatic heterocyclic compound represented by Formula (1), which is used in Examples 1 to 9, is superior in deprotection rate as compared with the compounds used in Comparative Examples 1 and 2, thereby being excellent in yield of peptide compound.

Examples 10 to 15 and Comparative Examples 3 and 4

(Evaluation 2)
<Deprotection Rate>

With regard to the N-terminal and C-terminal protected amino acid compounds synthesized above, which are shown in Table 2, the deprotection ratio (deprotection ratio of C-terminal end) of the protected carboxamide moiety was determined as follows.

100 mg of Fmoc-Leu-NR-Tag (N-terminal and C-terminal protected amino acids of the compounds of Examples and N-terminal and C-terminal protected amino acids of the compounds of Comparative Examples) and Fmoc-Gly-OH (internal standard) in an equimolar amount of Fmoc-Leu-NR-Tag were mixed, and then chloroform/triisopropylsilane/3,6-dioxa-1,8-octanedithiol/water/trifluoroacetic acid (42.5/2.5/2.5/2.5/50: vol %) was added thereto so that the substrate concentration was 0.025 M based on Fmoc-Leu-OTag, and the mixture was stirred at 30° C. for 60 minutes.

5 μL of the reaction solution was dissolved in 400 μL of methanol (MeOH), and using Ultra Performance LC (ultra-performance liquid chromatography, manufactured by Waters Corporation, model number: ACQUITY), the deprotection ratio (%) was determined by quantifying the ratio of Fmoc-Leu-NH$_2$ and Fmoc-Gly-OH produced by deprotecting Fmoc-Leu-NR-Tag, and evaluated based on the following standard.

The columns and measurement conditions used for the ultra-performance liquid chromatography are shown below.

Column: manufactured by Waters Corporation, model number: BEH C18 1.7 μm, 2.1 mm×30 mm Flow rate: 0.5 mL/min Solvent: solution A: 0.1% formic acid-water, solution B: 0.1% formic acid-acetonitrile Gradient cycle: 0.00 min (solution A/solution B=95/5), 2.00 min (solution A/solution B=5/95), 3.00 min (solution A/solution B=95/5)

Detection wavelength: 254 nm

Regarding the evaluation of the deprotection rate, a case of "B" or higher was regarded as acceptable. The results are shown in Table 2.

It can be said that, as the deprotection ratio is higher, the deprotection rate is higher and the deprotection rate is excellent.

—Evaluation Standard—
"A": deprotection ratio was 90% or more.
"B": deprotection ratio was 80% or more and less than 90%.
"C": deprotection ratio was 50% or more and less than 80%.
"D": deprotection ratio was less than 50%.

TABLE 2

| | Type of protective group | Deprotection rate |
|---|---|---|
| Example 10 | Compound (1-N-2) | A |
| Example 11 | Compound (1-N-3) | A |
| Example 12 | Compound (1-N-5) | A |
| Example 13 | Compound (1-N-2-1) | A |
| Example 14 | Compound (1-N-2-2) | A |
| Example 15 | Compound (1-N-2-3) | A |
| Comparative example 3 | Comparative compound (3) | D |
| Comparative example 4 | Comparative compound (4) | C |

Details of the compounds in Table 2 are as follows.

Comparative compound (3) was synthesized according to the method described in paragraphs 0094 to 0097 of JP2009-185063A.

Comparative compound (3)

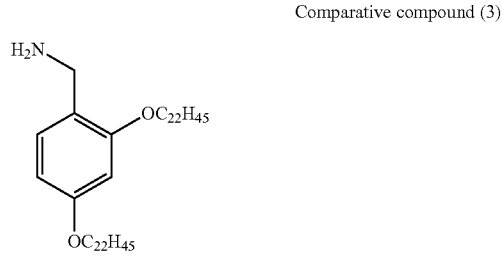

Comparative compound (4) was synthesized according to the method described in paragraphs 0147 to 0155 of WO2010/113939A.

Comparative compound (4)

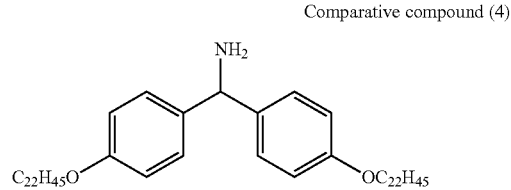

As shown in Table 2, the aromatic heterocyclic compound represented by Formula (1), which is used in Examples 10 to 15, is superior in deprotection rate as compared with the compounds used in Comparative Examples 3 and 4, thereby being excellent in yield of peptide compound.

(Evaluation 3)

After synthesizing, according to the following method, an N-terminal and C-terminal protected peptide compound (7-residue peptide compound) using the compound represented by Formula (1) according to the present disclosure, the C-terminal protective group was deprotected and the deprotection rate was evaluated.

Details of each abbreviation other than the above are shown below.

Gly: glycine residue
Asn(Trt): triphenylmethyl (Trt)-protected asparagine residue
Trt: trityl group
Asp(tBu): tBu-protected aspartic acid residue
tBu: t-butyl group
Phe: phenylalanine residue
Glu(tBu): tBu-protected glutamic acid residue <Synthesis of N-Terminal and C-Terminal Protected Peptide (7-Residue Peptide: Fmoc-Gly-Gly-Asn(Trt)-Gly-Asp(tBu)-Phe-Glu(tBu)-O-Protective Group (SEQ ID NO: 1))>

Synthesis Example 1: Synthesis of Fmoc-Glu(tBu)-O-5-IndoTAG (1)

1-(3,5-bis(docosyloxy)benzyloxy)-1H-indol-5-ylmethanol (corresponding to the compound (1-1); also referred to as "5-IndoTAG (1)") (1.00 g, 1.13 mmol) and Fmoc-Glu(tBu)-OH (1.5 molar equivalent) were dissolved in dichloromethane (23 mL), and 4-dimethylaminopyridine (0.2 molar equivalent) and diisopropylcarbodiimide (1.5 molar equivalent) were added thereto and stirred. After the condensation reaction was completed, acetonitrile (MeCN, 100 mL) was added thereto and stirred, and then the precipitate was filtered, washed with acetonitrile, and dried under reduced pressure to obtain Fmoc-Glu(tBu)-O-5-IndoTAG (1) (1.46 g, yield: 100%).

The Fmoc-Glu(tBu)-O-5-IndoTAG (1) is a peptide compound in which an N-terminal end is protected by an Fmoc group and a C-terminal end is protected by the aromatic heterocyclic compound represented by Formula (1) according to the present disclosure.

Synthesis Example 2: Synthesis of Fmoc-Phe-Glu(tBu)-O-5-IndoTAG (1)

Fmoc-Glu(tBu)-O-5-IndoTAG (1) (1.34 g, 1.04 mmol) was dissolved in chloroform (2.6 mL), and diazabicycloundecene (DBU, 2.0 molar equivalent) was added thereto and stirred. After the deprotection reaction was completed, a chloroform solution including methanesulfonic acid (2.1 molar equivalent) and N-methylmorpholine (2.1 molar equivalent) was added thereto, and Fmoc-Phe-OH (1.2 molar equivalent) and (1-cyano-2-ethoxy-2-oxoethylideaminooxy)dimethylamino-morpholino-carbenium hexafluorophosphate (COMU, 1.2 molar equivalent) were added thereto and stirred. After the condensation reaction was completed, MeCN (50 mL) was added thereto and stirred, and then the precipitate was filtered, washed with acetonitrile, and dried under reduced pressure to obtain Fmoc-Phe-Glu(tBu)-O-5-IndoTAG (1) (1.49 g, yield: 100%).

Synthesis Example 3: Synthesis of Fmoc-Asp(tBu)-Phe-Glu(tBu)-O-5-IndoTAG (1)

Fmoc-Phe-Glu(tBu)-O-5-IndoTAG (1) (1.49 g, 1.03 mmol) was dissolved in chloroform (5.0 mL), and DBU (2.0 molar equivalent) was added thereto and stirred. After the deprotection reaction was completed, a chloroform solution including methanesulfonic acid (2.1 molar equivalent) and N-methylmorpholine (2.1 molar equivalent) was added thereto, and Fmoc-Asp(tBu)-OH (1.2 molar equivalent) and COMU (1.2 molar equivalent) were added thereto and stirred. After the condensation reaction was completed, MeCN (50 mL) was added thereto and stirred, and then the precipitate was filtered, washed with acetonitrile, and dried under reduced pressure to obtain Fmoc-Asp(tBu)-Phe-Glu(tBu)-O-5-IndoTAG (1) (1.46 g, yield: 87.6%).

Synthesis Example 4: Synthesis of Fmoc-Gly-Asp(tBu)-Phe-Glu(tBu)-O-5-IndoTAG (1) (SEQ ID NO: 2)

Fmoc-Asp(tBu)-Phe-Glu(tBu)-O-5-IndoTAG (1) (1.31 g, 0.812 mmol) was dissolved in chloroform (4.0 mL), and DBU (2.0 molar equivalent) was added thereto and stirred. After the deprotection reaction was completed, a chloroform solution including methanesulfonic acid (2.1 molar equivalent) and N-methylmorpholine (2.1 molar equivalent) was added thereto, and Fmoc-Gly-OH (1.2 molar equivalent) and COMU (1.2 molar equivalent) were added thereto and stirred. After the condensation reaction was completed, MeOH (50 mL) was added thereto and stirred, and then the precipitate was filtered, washed with acetonitrile, and dried under reduced pressure to obtain Fmoc-Gly-Asp(tBu)-Phe-Glu(tBu)-O-5-IndoTAG (1) (SEQ ID NO: 2) (1.36 g, yield: 100%).

Synthesis Example 5: Synthesis of Fmoc-Asn(Trt)-Gly-Asp(tBu)-Phe-Glu(tBu)-O-5-IndoTAG (1) (SEQ ID NO: 3)

Fmoc-Gly-Asp(tBu)-Phe-Glu(tBu)-O-5-IndoTAG (1) (SEQ ID NO: 2) (1.36 g, 0.815 mmol) was dissolved in chloroform (3.8 mL), and DBU (2.0 molar equivalent) was added thereto and stirred. After the deprotection reaction was completed, a chloroform solution including methanesulfonic acid (2.1 molar equivalent) and N-methylmorpholine (2.1 molar equivalent) was added thereto, and Fmoc-Asn(Trt)-OH (1.2 molar equivalent) and COMU (1.2 molar equivalent) were added thereto and stirred. After the condensation reaction was completed, MeCN (50 mL) was added thereto and stirred, and then the precipitate was filtered, washed with acetonitrile, and dried under reduced pressure to obtain Fmoc-Asn(Trt)-Gly-Asp(tBu)-Phe-Glu(tBu)-O-5-IndoTAG (1) (SEQ ID NO: 3) (1.35 g, yield: 81.8%).

Synthesis Example 6: Synthesis of Fmoc-Gly-Gly-Asn(Trt)-Gly-Asp(tBu)-Phe-Glu(tBu)-O-5-IndoTAG (1) (SEQ ID NO: 4)

Fmoc-Asn(Trt)-Gly-Asp(tBu)-Phe-Glu(tBu)-O-5-IndoTAG (1) (SEQ ID NO: 3) (1.00 g, 0.494 mmol) was dissolved in chloroform (6.0 mL), and DBU (2.0 molar equivalent) was added thereto and stirred. After the deprotection reaction was completed, a chloroform solution including methanesulfonic acid (2.1 molar equivalent) and N-methylmorpholine (2.1 molar equivalent) was added thereto, and Fmoc-Gly-Gly-OH (1.2 molar equivalent) and COMU (1.2 molar equivalent) were added thereto and stirred. After the condensation reaction was completed, MeCN (50 mL) was added thereto and stirred, and then the precipitate was filtered, washed with acetonitrile, and dried under reduced pressure to obtain Fmoc-Gly-Gly-Asn(Trt)-Gly-Asp(tBu)-Phe-Glu(tBu)-O-5-IndoTAG (1) (SEQ ID NO: 4) (1.02 g, yield: 96.6%).

<Deprotection of C-Terminal Protective Group>

Synthesis Example 7: Synthesis of Fmoc-Gly-Gly-Asn(Trt)-Gly-Asp(tBu)-Phe-Glu(tBu)-OH (SEQ ID NO: 5)

A mixed solvent (9.0 mL, volume ratio: 100:10:2) of cooled dichloromethane, 2,2,2-trifluoroethanol, and trifluoroacetic acid was added to Fmoc-Gly-Gly-Asn(Trt)-Gly-Asp(tBu)-Phe-Glu(tBu)-O-5-IndoTAG (1) (SEQ ID NO: 4) (500 mg, 0.234 mmol), and the mixture was stirred at room temperature for 2 hours. The reaction solution was filtered, diisopropyl ether (80 mL) was added to the filtrate, and the resulting precipitate was centrifuged to be recovered. Thereafter, the recovered precipitate was suspended again in diisopropyl ether (80 mL), centrifuged twice, and then dried under reduced pressure, thereby obtaining Fmoc-Gly-Gly-Asn(Trt)-Gly-Asp(tBu)-Phe-Glu(tBu)-OH (X) (SEQ ID NO: 5) (297 mg, yield: 100%), in which only C-terminal protective group (5-IndoTAG (1)) was deprotected.

Electrospray ionization mass spectrometry (ESI-MS) (+)=1,271.5

Synthesis Example 8: Synthesis of Fmoc-Gly-Gly-Asn(Trt)-Gly-Asp(tBu)-Phe-Glu(tBu)-OH (SEQ ID NO: 5)

Fmoc-Gly-Gly-Asn(Trt)-Gly-Asp(tBu)-Phe-Glu(tBu)-O-BfTAG (2) (SEQ ID NO: 6) was synthesized in the same manner as in Synthesis Examples 1 to 6, except that the compound (4-1) (hereinafter, also referred to as "BfTAG (2)") was used in Synthesis Example 1 instead of the compound (1-1) (total yield: 81%). Same as Synthesis Example 7, only C-terminal protective group (BfTAG (2)) was selectively deprotected, thereby obtaining Fmoc-Gly-Gly-Asn(Trt)-Gly-Asp(tBu)-Phe-Glu(tBu)-OH (SEQ ID NO: 5).

In the 7-residue peptide in which the above-described C-terminal protective groups were deprotected, the Trt group of the Asn protective group, the tBu group of the Asp protective group, and the tBu group of the Glu protective group remained, and only C-terminal protective group was deprotected. As described above, according to the method for producing a peptide compound according to the embodiment of the present disclosure, it is possible to selectively deprotect only the C-terminal protective group while leaving a protective group of an amino acid side chain, so that the method for producing a peptide compound according to the embodiment of the present disclosure is excellent in deprotection rate. In addition, the method for producing a peptide compound according to the embodiment of the present disclosure is also excellent in yield of the obtained peptide compound.

<Synthesis of 9-Residue Peptide: Pyr-his-Trp-Ser-Tyr-dLeu-Leu-Arg-Pro-NHEt>

Details of each abbreviation other than the above are shown below.

Pyr(Boc): Boc-protected pyroglutamic acid residue
His(Boc): Boc-protected histamine residue
Trp(Boc): Boc-protected tryptophan residue
Boc: t-butoxycarbonyl group
Ser(tBu): tBu-protected serine residue
tBu: t-butyl group
Tyr(tBu): tBu-protected tyrosine residue
dLeu: D-leucine residue
Arg(pbf): pbf-protected arginine residue
pbf: 2,2,4,6,7-pentamethyldihydrobenzofuran-5-sulfonyl group
Pro: proline residue
Et: ethyl group Synthesis Example 9: Synthesis of Fmoc-Pro-NEtTAG (3)

N-(1-(3,5-bis(docosanoyloxybenzyloxy))-1H-indol-3-yl-methyl)ethaneamine (corresponding to the above-described compound (1-N-2); also referred to as "NEtTAG (3)") (2.00 g, 2.19 mmol) and Fmoc-Pro-OH (1.5 molar equivalent) were dissolved in tetrahydrofuran (11 mL), and diisopropylethylamine (2.2 molar equivalent) and (1-cyano-2-ethoxy-2-oxoethylidenaminooxy)dimethylamino-morpholino-carbenium hexafluorophosphate (COMU, 1.5 molar equivalent) were added thereto and stirred. After the condensation reaction was completed, acetonitrile (60 mL) was added thereto and stirred, and then the precipitate was filtered, washed with acetonitrile, and dried under reduced pressure to obtain Fmoc-Pro-NEtTAG (3) (2.62 g, yield: 96.9%).

Synthesis Example 10: Synthesis of Fmoc-Arg(Pbf)-Pro-NEtTAG (3)

Fmoc-Pro-NEtTAG (3) (2.60 g, 2.11 mmol) was dissolved in tetrahydrofuran (11 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Arg(pbf)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (55 mL) was added thereto and stirred, and then the precipitate was filtered, washed with acetonitrile, and dried under reduced pressure to obtain Fmoc-Arg(pbf)-Pro-NEtTAG (3) (3.43 g, yield: 99.1%).

Synthesis Example 11: Synthesis of Fmoc-Leu-Arg(Pbf)-Pro-NEtTAG (3)

Fmoc-Arg(pbf)-Pro-NEtTAG (3) (3.41 g, 2.08 mmol) was dissolved in tetrahydrofuran (10 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Leu-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (55 mL) was added thereto and stirred, and then the precipitate was filtered, washed with acetonitrile, and dried under reduced pressure to obtain Fmoc-Leu-Arg(pbf)-Pro-NEtTAG (3) (3.45 g, yield: 94.6%).

Synthesis Example 12: Synthesis of Fmoc-dLeu-Leu-Arg(Pbf)-Pro-NEtTAG (3)

Fmoc-Leu-Arg(pbf)-Pro-NEtTAG (3) (3.42 g, 1.95 mmol) was dissolved in tetrahydrofuran (9.7 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-dLeu-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (50 mL) was added thereto and stirred, and then the precipitate was filtered, washed with acetonitrile, and dried under reduced pressure to obtain Fmoc-dLeu-Leu-Arg(pbf)-Pro-NEtTAG (3) (3.45 g, yield: 94.8%).

Synthesis Example 13: Synthesis of Fmoc-Tyr(tBu)-dLeu-Leu-Arg(pbf)-Pro-NEtTAG (3)

Fmoc-dLeu-Leu-Arg(pbf)-Pro-NEtTAG (3) (3.48 g, 1.86 mmol) was dissolved in tetrahydrofuran (9.3 mL), and DBU (2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Tyr(tBu)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (95 mL) was added thereto and stirred, and then the precipitate was filtered, washed with acetonitrile, and dried under reduced pressure to obtain Fmoc-Tyr(tBu)-dLeu-Leu-Arg(pbf)-Pro-NEtTAG (3) (3.74 g, yield: 96.2%).

Synthesis Example 14: Synthesis of Fmoc-Ser(tBu)-Tyr(tBu)-dLeu-Leu-Arg(pbf)-Pro-NEtTAG (3)

Fmoc-Tyr(tBu)-dLeu-Leu-Arg(pbf)-Pro-NEtTAG (3) (3.67 g, 1.76 mmol) was dissolved in tetrahydrofuran (8.8 mL), and DBU (2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Ser(tBu)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (90 mL) was added thereto and stirred, and then the precipitate was filtered, washed with acetonitrile, and dried under reduced pressure to obtain Fmoc-Ser(tBu)-Tyr(tBu)-dLeu-Leu-Arg(pbf)-Pro-NEtTAG (3) (3.72 g, yield: 94.9%).

Synthesis Example 15: Synthesis of Fmoc-Trp(Boc)-Ser(tBu)-Tyr(tBu)-dLeu-Leu-Arg(pbf)-Pro-NEtTAG (3)

Fmoc-Ser(tBu)-Tyr(tBu)-dLeu-Leu-Arg(pbf)-Pro-NEtTAG (3) (3.67 g, 1.65 mmol) was dissolved in tetrahydrofuran (8.2 mL), and DBU (2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Trp(Boc)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (80 mL) was added thereto and stirred, and then the precipitate was filtered, washed with acetonitrile, and dried under reduced pressure to obtain Fmoc-Trp(Boc)-Ser(tBu)-Tyr(tBu)-dLeu-Leu-Arg(pbf)-Pro-NEtTAG (3) (3.79 g, yield: 91.5%).

Synthesis Example 16: Synthesis of Fmoc-His(Boc)-Trp(Boc)-Ser(tBu)-Tyr(tBu)-dLeu-Leu-Arg(pbf)-Pro-NEtTAG (3)

Fmoc-Trp(Boc)-Ser(tBu)-Tyr(tBu)-dLeu-Leu-Arg(pbf)-Pro-NEtTAG (3) (3.78 g, 1.50 mmol) was dissolved in tetrahydrofuran (7.5 mL), and DBU (2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-His(Boc)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (75 mL) was added thereto and stirred, and then the precipitate was filtered, washed with acetonitrile, and dried under reduced pressure to obtain Fmoc-His(Boc)-Trp(Boc)-Ser(tBu)-Tyr(tBu)-dLeu-Leu-Arg(pbf)-Pro-NEtTAG (3) (3.45 g, yield: 83.4%).

Synthesis Example 17: Synthesis of Pyr(Boc)-His(Boc)-Trp(Boc)-Ser(tBu)-Tyr(tBu)-dLeu-Leu-Arg(pbf)-Pro-NEtTAG (3)

Fmoc-His(Boc)-Trp(Boc)-Ser(tBu)-Tyr(tBu)-dLeu-Leu-Arg(pbf)-Pro-NEtTAG (3) (1.96 g, 0.71 mmol) was dissolved in tetrahydrofuran (4.7 mL), and DBU (2.0 molar equivalent) was added thereto and stirred. After the deprotection reaction was completed, N-methylmorpholine (2.05 molar equivalent) and methanesulfonic acid (2.0 molar equivalent) were added thereto, and Fmoc-Pyr(Boc)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, 2-Me-THF (10 mL) and a saturated sodium hydrogen carbonate aqueous solution (10 mL) were added thereto for separation, and the organic layer was washed with a saturated sodium hydrogen carbonate aqueous solution and saturated saline. After drying the organic layer over anhydrous magnesium sulfate, the solvent was distilled off under reduced pressure, and the obtained solid was washed with hexane to obtain Pyr(Boc)-His(Boc)-Trp(Boc)-Ser(tBu)-Tyr(tBu)-dLeu-Leu-Arg(pbf)-Pro-NEtTAG (3) (1.94 g, yield: 99.4%).

Synthesis Example 18: Synthesis of Pyr-His-Trp-Ser-Tyr-dLeu-Leu-Arg-Pro-NHEt

A mixed solution of trifluoroacetic acid (TFA, 26.6 mL), triisopropylsilane (TIPS, 0.72 mL), 3,6-dioxa-1,8-octanedithiol (DODT, 0.72 mL), and water (0.72 mL) was added to Pyr(Boc)-His(Boc)-Trp(Boc)-Ser(tBu)-Tyr(tBu)-dLeu-Leu-Arg(pbf)-Pro-NEtTAG (3) (1.90 g, 0.87 mmol), and the mixture was stirred for 90 minutes. After the deprotection reaction was completed, methyl-t-butyl ether (MTBE, 60 mL) was added thereto and stirred, and the supernatant was removed by centrifugation. The addition of MTBE, centrifugation, and removal of the supernatant were repeated 3 times to obtain Pyr-His-Trp-Ser-Tyr-dLeu-Leu-Arg-Pro-NHEt (0.812 g, yield: 93.4%).

Electrospray ionization mass spectrometry (ESI-MS) (+)=1,209.8

<Synthesis of 5-Residue Peptide: Fmoc-McNle-MeNle-Arg(Pbf)-Cys(Trt)-Gly-NH$_2$ (SEQ ID NO: 7)>

Details of each abbreviation other than the above are shown below.

MeNle: N-methylnorleucine residue
Cys(Trt): Trt-protected cysteine residue
Gly: glycine residue

Synthesis Example 19: Synthesis of Fmoc-Gly-NH-DMPIndoTAG (4)

Fmoc-Gly-NH-DMPIndoTAG (4) was synthesized in the same manner as in Synthesis Example 9, except that, in Synthesis Example 9, the compound (1-N-2-3) (hereinafter, also referred to as "DMPIndoTAG (4)") was used instead of the compound (1-N-2) and Fmoc-Gly-OH was used instead of Fmoc-Pro-OH.

Synthesis Example 20: Synthesis of Fmoc-MeNle-MeNle-Arg(Pbf)-Cys(Trt)-Gly-NH$_2$-DMPIndoTAG (4) (SEQ ID NO: 8)

Using Fmoc-Gly-NH-DMPIndoTAG (4) obtained in Synthesis Example 19, the removal of the Fmoc group and the condensation reaction of amino acids were repeated in the same manner as in Synthesis Example 10 to synthesize Fmoc-MeNle-MeNle-Arg(Pbf)-Cys(Trt)-Gly-NH$_2$-DMPIndoTAG (4) (SEQ ID NO: 8) (total yield: 75%).

Since the DMPIndoTAG (4) which was the C-terminal protective group of Fmoc-MeNle-MeNle-Arg(Pbf)-Cys(Trt)-Gly-NH$_2$-DMPIndoTAG (4) (SEQ ID NO: 8) obtained in Synthesis Example 20 can be deprotected with a low concentration of TFA, it can be said that DMPIndoTAG (4) is suitable for the synthesis of peptide which is unstable to acid.

The aromatic heterocyclic compound represented by Formula (1), which is used in Synthesis Examples 19 and 20, is excellent in deprotection rate and yield of the obtained peptide compound.

The disclosure of Japanese Patent Application No. 2019-035775 filed on Feb. 28, 2019 and the disclosure of Japanese Patent Application No. 2019-122489 filed on Jun. 28, 2019 are incorporated in the present specification by reference.

All documents, patent applications, and technical standards described in the present specification are incorporated herein by reference to the same extent as in a case of being specifically and individually noted that individual documents, patent applications, and technical standards are incorporated by reference.

What is claimed is:

1. A method for producing a peptide compound, comprising:
a step of using an aromatic heterocyclic compound represented by Formula (1),

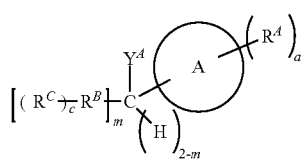

(1)

in Formula (1),
a ring A represents an aromatic heterocyclic ring,
$Y^A$ represents —OH, —NHR, SH, or —$X^0$, where R represents a hydrogen atom, an alkyl group, an aromatic group-substituted alkyl group, a heteroaromatic group-substituted alkyl group, or a 9-fluorenyl-methoxycarbonyl group, and $X^0$ represents Cl, Br, or I, $R^A$'s each independently represent an aliphatic hydrocarbon group or an organic group having an aliphatic hydrocarbon group, and the ring A may further have a substituent in addition to $R^A$, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, and the number of carbon atoms in at least one aliphatic hydrocarbon group of $R^A$, $R^B$, or $R^C$ is 12 or more.

2. The method for producing a peptide compound according to claim 1,
wherein the step of using the aromatic heterocyclic compound represented by Formula (1) is a C-terminal protecting step of protecting a carboxy group or an amide group of an amino acid compound or a peptide compound with the aromatic heterocyclic compound represented by Formula (1).

3. The method for producing a peptide compound according to claim 2,
wherein the amino acid compound or the peptide compound in the C-terminal protecting step is an N-terminal protected amino acid compound or an N-terminal protected peptide compound.

4. The method for producing a peptide compound according to claim 3, further comprising:
an N-terminal deprotecting step of deprotecting an N-terminal end of an N-terminal and C-terminal protected amino acid compound or an N-terminal and C-terminal protected peptide compound, which is obtained in the C-terminal protecting step; and
a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound.

5. The method for producing a peptide compound according to claim 4, further comprising:
a precipitating step of precipitating an N-terminal and C-terminal protected peptide compound obtained in the peptide chain extending step.

6. The method for producing a peptide compound according to claim 5, further comprising, one or more times in the following order after the precipitating step:
a step of deprotecting an N-terminal end of the obtained N-terminal and C-terminal protected peptide compound;
a step of condensing the N-terminal end of the obtained C-terminal protected peptide compound with an N-terminal protected amino acid compound or an N-terminal protected peptide compound; and
a step of precipitating the obtained N-terminal and C-terminal protected peptide compound.

7. The method for producing a peptide compound according to claim 1, further comprising:
a C-terminal deprotecting step of deprotecting a C-terminal protective group.

8. The method for producing a peptide compound according to claim 1,
wherein the ring A is a pyrrole ring, an indole ring, a carbazole ring, a pyrazole ring, an indazole ring, a furan ring, a thiophene ring, a benzofuran ring, or a benzothiophene ring.

9. The method for producing a peptide compound according to claim 1,
wherein the ring A is represented by any of Formula (10), Formula (20), or Formula (30),

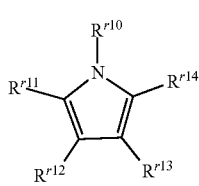

(10)

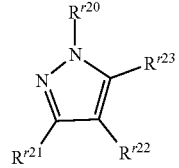

(20)

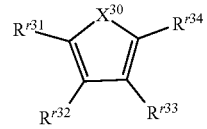

(30)

in Formula (10), any one of $R^{r10}$, $R^{r11}$, $R^{r12}$, $R^{r13}$, or $R^{r14}$ is linked to a group which includes the carbon atom having $Y^A$ in Formula (1), $R^{10}$ represents a substituent or $R^A$, $R^{r11}$ to $R^{r14}$ each independently represent a hydrogen atom, a substituent, or $R^A$, and at least one of $R^{r10}$, $R^{r11}$, $R^{r12}$, $R^{r13}$, or $R^{r14}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r11}$ and $R^{r12}$, or $R^{r13}$ and $R^{r14}$ may be each independently linked to each other to form a ring, in Formula (20), any one of $R^{r20}$, $R^{r21}$, $R^{r22}$, or $R^{r23}$ is linked to a group which includes the carbon atom having $Y^A$ in Formula (1), $R^{20}$ represents a substituent or $R^A$, $R^{r21}$ to $R^{r23}$ each independently represent a hydrogen atom, a substituent, or $R^A$, and at least one of $R^{r20}$, $R^{r21}$, $R^{r22}$, or $R^{r23}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r22}$ and $R^{r23}$ may be linked to each other to form a ring, and in Formula (30), any one of $R^{r31}$, $R^{r32}$, $R^{r33}$, or $R^{r34}$ is linked to a group which includes the carbon atom having $Y^A$ in Formula (1), $X^{30}$ represents an oxygen atom or a sulfur atom, $R^{r31}$ to $R^{r34}$ each independently represent a hydrogen atom, a substituent, or $R^A$, and at least one of $R^{r31}$, $R^{r32}$, $R^{r33}$, or $R^{r34}$ is $R^A$, where $R^A$'s each independently represent an aliphatic hydrocarbon group or an organic group having an aliphatic hydrocarbon group, the number of carbon atoms in at least one aliphatic hydrocarbon group in at least one $R^A$ is 12 or more, and $R^{r31}$ and $R^{r32}$, or $R^{r33}$ and $R^{r34}$ may be each independently linked to each other to form a ring.

10. The method for producing a peptide compound according to claim 1,
wherein the number of carbon atoms in at least one aliphatic hydrocarbon group in at least one $R^A$ is 14 or more.

11. The method for producing a peptide compound according to claim 9,
wherein the ring A represented by Formula (10) is represented by Formula (11),
a compound represented by Formula (20) is represented by Formula (21), and
a compound represented by Formula (30) is represented by Formula (31),

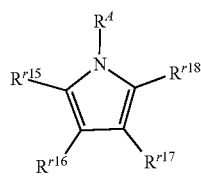
(11)

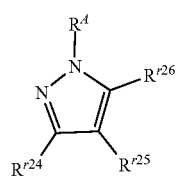
(21)

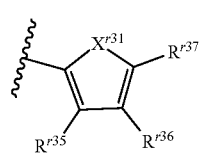
(31)

in Formula (11), any one of $R^{r15}$, $R^{r16}$, $R^{r17}$, or $R^{r18}$ is linked to the group which includes the carbon atom having $Y^A$ in Formula (1), $R^{r15}$ to $R^{r18}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in $R^A$ is 14 or more, and $R^{r15}$ and $R^{r16}$, or $R^{r17}$ and $R^{r18}$ may be each independently linked to each other to form a ring, in Formula (21), any one of $R^{r24}$, $R^{r25}$, or $R^{r26}$ is linked to the group which includes the carbon atom having $Y^A$ in Formula (1), $R^{r24}$ to $R^{r26}$ each independently represent a hydrogen atom or a substituent, $R^A$ is an aliphatic hydrocarbon group or an organic group having an aliphatic hydrocarbon group, the number of carbon atoms in at least one aliphatic hydrocarbon group in $R^A$ is 14 or more, and $R^{r25}$ and $R^{r26}$ may be linked to each other to form a ring, and in Formula (31), the wavy line portion represents a position linked to the group which includes the carbon atom having $Y^A$ in Formula (1), $X^{r31}$ represents an oxygen atom or a sulfur atom, $R^{r35}$ to $R^{r37}$ each independently represent a hydrogen atom, a substituent, or $R^A$, $R^A$'s each independently represent an aliphatic hydrocarbon group or an organic group having an aliphatic hydrocarbon group, the number of carbon atoms in at least one aliphatic hydrocarbon group in $R^A$ is 14 or more, at least one of $R^{r35}$, $R^{r36}$, or $R^{r37}$ is $R^A$, and $R^{r36}$ and $R^{r37}$ may be linked to each other to form a ring.

12. The method for producing a peptide compound according to claim 1, wherein a total number of carbon atoms in all aliphatic hydrocarbon groups included in all $R^A$'s is 40 or more.

13. The method for producing a peptide compound according to claim 1, wherein $R^A$ is a group represented by Formula (f1) or a group represented by Formula (a1),

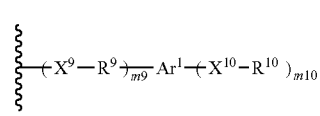
(f1)

in Formula (f1), the wavy line portion represents a bonding position to an aromatic heterocyclic ring, m9 represents an integer of 0 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms, and

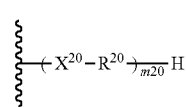
(a1)

in Formula (a1), the wavy line portion represents a bonding position to an aromatic heterocyclic ring, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

14. The method for producing a peptide compound according to claim 13, wherein the group represented by Formula (f1) is a group represented by Formula (f2),

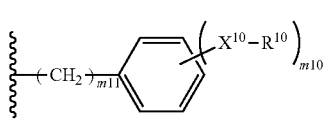
(f2)

in Formula (f2), the wavy line portion represents a bonding position to an aromatic heterocyclic ring, m10 represents an integer of 1 to 3, m11 represents an integer of 0 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

15. An aromatic heterocyclic compound represented by Formula (1a),

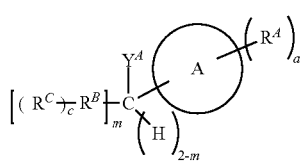

(1a)

in Formula (1a), a ring A represents an aromatic heterocyclic ring, $Y^A$ represents —OH, —NHR, SH, or —$X^0$, where R represents a hydrogen atom, an alkyl group, an aromatic group-substituted alkyl group, a heteroaromatic group-substituted alkyl group, or a 9-fluorenylmethoxycarbonyl group, and $X^0$ represents Cl, Br, or I, $R^A$'s each independently represent a group represented by Formula (f1):

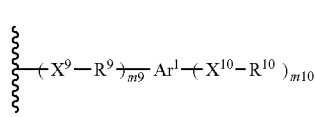

(f1)

in Formula (f1), the wavy line portion represents a bonding position to an aromatic heterocyclic ring, m9 represents an integer of 0 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms, and the ring A may further have a substituent in addition to $R^A$, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, the number of carbon atoms in at least one aliphatic hydrocarbon group included in at least one of $R^A$, $R^B$, or $R^C$ is 12 or more, and a total number of carbon atoms in all aliphatic hydrocarbon groups included in all $R^A$, $R^B$, and $R^C$ is 40 or more, wherein the ring A is represented by any of Formula (11a), Formula (21a), or Formula (31a),

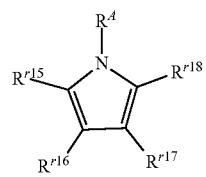

(11a)

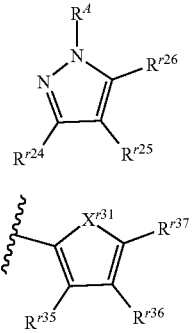

(21a)

(31a)

in Formula (11a), any one of $R^{r15}$, $R^{r16}$, $R^{r17}$, or $R^{r18}$ is linked to the group which includes the carbon atom having $Y^A$ in Formula (1a), $R^{r15}$ to $R^{r18}$ each independently represent a hydrogen atom or a substituent, $R^A$ is a group represented by Formula (f1), the number of carbon atoms in at least one aliphatic hydrocarbon group in $R^A$ is 14 or more, and $R^{r15}$ and $R^{r16}$, or $R^{r17}$ and $R^{r18}$ may be each independently linked to each other to form a ring, in Formula (21a), any one of $R^{r24}$, $R^{r25}$, or $R^{r26}$ is linked to the group which includes the carbon atom having $Y^A$ in Formula (1a), $R^{r24}$ to $R^{r26}$ each independently represent a hydrogen atom or a substituent, $R^A$ is a group represented by Formula (f1), the number of carbon atoms in at least one aliphatic hydrocarbon group in $R^A$ is 14 or more, and $R^{r25}$ and $R^{r26}$ may be linked to each other to form a ring, and in Formula (31a), the wavy line portion represents a position linked to the group which includes the carbon atom having $Y^A$ in Formula (1a), $X^{r31}$ represents an oxygen atom or a sulfur atom, $R^{r35}$ to $R^{r37}$ each independently represent a hydrogen atom, a substituent, or $R^A$, $R^A$'s each independently represent a group represented by Formula (f1), the number of carbon atoms in at least one aliphatic hydrocarbon group in $R^A$ is 14 or more, and at least one of $R^{r35}$, $R^{r36}$, or $R^{r37}$ is $R^A$ and may be linked to $R^{r36}$ to form a ring.

16. The aromatic heterocyclic compound according to claim 15, wherein a total number of carbon atoms in all aliphatic hydrocarbon groups included in all $R^A$, $R^B$, and $R^C$ is 40 to 80.

17. An aromatic heterocyclic compound represented by Formula (1a),

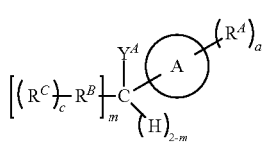

(1a)

wherein, in Formula (1a), a ring A represents an aromatic heterocyclic ring, $Y^A$ represents —OH, —NHR, SH, or —$X^0$, where R represents a hydrogen atom, an alkyl group, an aromatic group-substituted alkyl group, a heteroaromatic group-substituted alkyl group, or a 9-fluorenylmethoxycarbonyl group, and $X^0$ represents Cl, Br, or I, $R^A$'s each independently represent a group represented by Formula (f2),

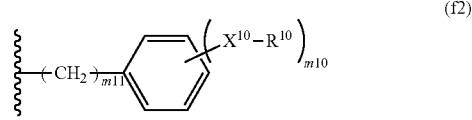

(f2)

in Formula (f2), the wavy line portion represents a bonding position to an aromatic heterocyclic ring, m10 represents an integer of 1 to 3, m11 represents an integer of 0 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms, $R^B$'s each independently represent a monovalent aliphatic hydrocarbon, a (1+c)-valent aromatic group, or a (1+c)-valent heteroaromatic group, $R^C$'s each independently represent an aliphatic hydrocarbon group or an organic group having an aliphatic hydrocarbon group, m represents an integer of 0 to 2, a represents an integer of 0 to 5, and c represents an integer of 0 to 5, in a case where both a and c are 0, $R^B$ is a monovalent aliphatic hydrocarbon group, the number of carbon atoms in at least one aliphatic hydrocarbon group included in at least one of $R^A$, $R^B$, or $R^C$ is 12 or more, and a total number of carbon atoms in all aliphatic hydrocarbon groups included in all $R^A$, $R^B$, and $R^C$ is 40 or more.

18. The aromatic heterocyclic compound according to claim 15, wherein the ring A is an indole ring, a carbazole ring, a pyrazole ring, an indazole ring, a furan ring, a benzofuran ring, or a benzothiophene ring.

* * * * *